United States Patent
Dubois et al.

(10) Patent No.: US 8,298,254 B2
(45) Date of Patent: Oct. 30, 2012

(54) DEVICES AND METHODS FOR CUTTING AND EVACUATING TISSUE

(75) Inventors: Brian R. Dubois, Redwood City, CA (US); James T. Nielsen, San Francisco, CA (US); Alexander Gordon, Menlo Park, CA (US)

(73) Assignee: Laurimed, LLC, Redwood City, CA (US)

( * ) Notice: Subject to any disclaimer, the term of this patent is extended or adjusted under 35 U.S.C. 154(b) by 22 days.

(21) Appl. No.: 13/174,416

(22) Filed: Jun. 30, 2011

(65) Prior Publication Data
US 2012/0004595 A1 Jan. 5, 2012

Related U.S. Application Data

(60) Provisional application No. 61/360,429, filed on Jun. 30, 2010, provisional application No. 61/377,883, filed on Aug. 27, 2010.

(51) Int. Cl.
*A61B 17/32* (2006.01)

(52) U.S. Cl. ...................................... 606/171

(58) Field of Classification Search .......... 606/167, 606/169, 170, 171; 173/14, 18, 19, 104, 173/109, 178; 600/564, 565, 566, 568, 570, 600/571; 83/17, 18, 19, 20, 21, 100, 919
See application file for complete search history.

(56) References Cited

U.S. PATENT DOCUMENTS

| | | |
|---|---|---|
| 1,527,291 A | 2/1925 | Zorraquin |
| 1,733,502 A | 10/1929 | Linsley |
| 2,395,455 A | 7/1959 | Clowes |
| 3,081,770 A | 3/1963 | Hunter |
| 3,469,580 A | 9/1969 | Huddy |
| 3,561,429 A * | 2/1971 | Jewett et al. ................. 600/565 |
| 3,682,162 A | 8/1972 | Colyer |
| 3,709,211 A | 1/1973 | Hawkins |
| 3,782,381 A | 1/1974 | Winnie |
| 3,815,604 A | 6/1974 | O'Malley et al. |
| 3,884,238 A | 5/1975 | O'Malley et al. |
| 3,941,127 A | 3/1976 | Froning |
| 3,943,932 A | 3/1976 | Woo |
| 4,013,080 A | 3/1977 | Froning |
| 4,068,659 A | 1/1978 | Moorehead |
| 4,192,319 A | 3/1980 | Hargens et al. |

(Continued)

FOREIGN PATENT DOCUMENTS

RU 2029533 2/1995

(Continued)

OTHER PUBLICATIONS

Sice et al. "Epidural analgesia after spinal surgery via intervertebral foramen," *British Journal of Anaesthesia*, 94(3), pp. 378-380, Dec. 24, 2004.

*Primary Examiner* — Ryan Severson
*Assistant Examiner* — Jonathan W Miles
(74) *Attorney, Agent, or Firm* — Levine Bagade Han LLP

(57) ABSTRACT

Various medical devices and methods for cutting and/or evacuating tissue are provided. The devices and methods may utilize a reciprocating mechanism or motor powered by suction from a vacuum source. The medical devices and methods may be used on tissue in various regions of a patient's body and for treating various conditions, e.g., for performing a polypectomy or discectomy.

46 Claims, 28 Drawing Sheets

U.S. PATENT DOCUMENTS

| | | |
|---|---|---|
| 4,314,560 A | 2/1982 | Helfgott et al. |
| RE30,966 E | 6/1982 | Hargens et al. |
| 4,349,023 A | 9/1982 | Gross |
| 4,368,730 A | 1/1983 | Sharrock |
| 4,511,356 A | 4/1985 | Froning et al. |
| 4,580,573 A | 4/1986 | Quinn |
| 4,588,399 A | 5/1986 | Nebergall et al. |
| 4,609,370 A | 9/1986 | Morrison |
| 4,662,869 A | 5/1987 | Wright |
| 4,678,459 A | 7/1987 | Onik et al. |
| 4,721,506 A | 1/1988 | Teves |
| 4,737,146 A | 4/1988 | Amaki et al. |
| 4,775,637 A | 10/1988 | Sutherland et al. |
| 4,808,157 A | 2/1989 | Coombs |
| 4,842,585 A | 6/1989 | Witt |
| 4,846,799 A | 7/1989 | Tanaka et al. |
| 4,886,067 A | 12/1989 | Palermo |
| 4,917,668 A | 4/1990 | Haindl |
| 4,917,670 A | 4/1990 | Hurley et al. |
| RE33,258 E | 7/1990 | Onik et al. |
| 4,940,458 A | 7/1990 | Cohn |
| 4,958,901 A | 9/1990 | Coombs |
| 4,973,305 A | 11/1990 | Goltzer |
| 4,973,312 A | 11/1990 | Andrew |
| 4,994,036 A | 2/1991 | Biscoping et al. |
| 5,004,456 A | 4/1991 | Botterbusch et al. |
| 5,007,902 A | 4/1991 | Witt |
| 5,024,655 A | 6/1991 | Freeman et al. |
| 5,026,350 A | 6/1991 | Tanaka et al. |
| 5,060,658 A * | 10/1991 | Dejter et al. ................. 600/566 |
| 5,078,679 A | 1/1992 | Reese |
| 5,085,631 A | 2/1992 | Leighton |
| 5,098,388 A | 3/1992 | Kulkashi et al. |
| 5,100,379 A | 3/1992 | Wendell |
| 5,100,390 A | 3/1992 | Lubeck et al. |
| 5,106,376 A | 4/1992 | Mononen et al. |
| 5,119,832 A | 6/1992 | Xavier |
| 5,129,889 A | 7/1992 | Hahn et al. |
| 5,135,525 A | 8/1992 | Biscoping et al. |
| 5,160,323 A | 11/1992 | Andrew |
| 5,163,901 A | 11/1992 | Eldor |
| 5,205,828 A | 4/1993 | Kedem |
| 5,207,647 A | 5/1993 | Phelps |
| 5,209,734 A | 5/1993 | Hurley et al. |
| 5,213,578 A | 5/1993 | Heiliger et al. |
| 5,232,442 A | 8/1993 | Johnson et al. |
| 5,234,406 A | 8/1993 | Drasner et al. |
| 5,257,972 A | 11/1993 | Gurmarnik |
| 5,263,936 A | 11/1993 | Yurino |
| 5,269,769 A | 12/1993 | Dhara et al. |
| 5,292,310 A | 3/1994 | Yoon |
| 5,304,141 A | 4/1994 | Johnson et al. |
| 5,306,239 A | 4/1994 | Gurmarnik et al. |
| 5,312,374 A | 5/1994 | Gurmarnik |
| 5,312,375 A | 5/1994 | Gurmarnik |
| 5,320,610 A | 6/1994 | Yoon |
| 5,328,479 A | 7/1994 | Gurmarnik |
| 5,335,671 A | 8/1994 | Clement |
| 5,368,573 A | 11/1994 | Andrew |
| 5,376,082 A | 12/1994 | Phelps |
| 5,385,561 A | 1/1995 | Cerny |
| 5,392,790 A | 2/1995 | Kanner et al. |
| 5,405,334 A | 4/1995 | Roth et al. |
| 5,417,208 A | 5/1995 | Winkler |
| 5,423,760 A | 6/1995 | Yoon |
| 5,423,770 A | 6/1995 | Yoon |
| 5,425,717 A | 6/1995 | Mohiuddin |
| 5,449,351 A | 9/1995 | Zohmann |
| 5,470,318 A | 11/1995 | Griffith, III et al. |
| 5,480,389 A | 1/1996 | McWha et al. |
| 5,490,845 A | 2/1996 | Racz |
| 5,512,045 A | 4/1996 | Gurchumelidze |
| 5,512,052 A | 4/1996 | Jesch |
| 5,520,652 A | 5/1996 | Peterson |
| 5,542,918 A | 8/1996 | Atkinson |
| 5,569,178 A | 10/1996 | Henley |
| 5,573,519 A | 11/1996 | Zohmann |
| 5,584,820 A | 12/1996 | Gurmarnik |
| 5,591,132 A | 1/1997 | Carrie |
| 5,611,778 A | 3/1997 | Brinon |
| 5,628,734 A | 5/1997 | Hatfalvi |
| 5,630,802 A | 5/1997 | Moellmann et al. |
| 5,637,096 A | 6/1997 | Yoon |
| 5,669,394 A * | 9/1997 | Bergey et al. ................. 600/563 |
| 5,669,876 A | 9/1997 | Schechter et al. |
| 5,669,882 A | 9/1997 | Pyles |
| 5,672,158 A | 9/1997 | Okada et al. |
| 5,685,852 A | 11/1997 | Turkel et al. |
| 5,725,504 A | 3/1998 | Collins |
| 5,730,754 A | 3/1998 | Obenchain |
| 5,752,969 A | 5/1998 | Cunci et al. |
| 5,779,666 A | 7/1998 | Teirstein |
| 5,779,680 A | 7/1998 | Yoon |
| 5,820,588 A | 10/1998 | Howard, III |
| 5,830,188 A | 11/1998 | Abouleish |
| 5,833,662 A | 11/1998 | Stevens |
| 5,836,914 A | 11/1998 | Houghton |
| 5,836,916 A | 11/1998 | Corn |
| 5,846,226 A | 12/1998 | Urmey |
| 5,853,391 A | 12/1998 | Bell |
| 5,857,996 A | 1/1999 | Snoke |
| 5,871,470 A | 2/1999 | McWha |
| 5,885,217 A | 3/1999 | Gisselberg et al. |
| 5,899,891 A | 5/1999 | Racz |
| 5,941,853 A | 8/1999 | Collins |
| 5,957,881 A | 9/1999 | Peters et al. |
| 5,976,110 A | 11/1999 | Greengrass et al. |
| 6,004,293 A | 12/1999 | Bell |
| 6,068,642 A | 5/2000 | Johnson et al. |
| 6,095,149 A | 8/2000 | Sharkey et al. |
| 6,113,569 A | 9/2000 | Becker |
| 6,179,828 B1 | 1/2001 | Mottola et al. |
| 6,190,370 B1 | 2/2001 | Tsui |
| 6,193,704 B1 | 2/2001 | Winters |
| 6,221,048 B1 | 4/2001 | Phelps |
| 6,224,630 B1 | 5/2001 | Bao et al. |
| 6,245,044 B1 | 6/2001 | Daw et al. |
| 6,273,873 B1 | 8/2001 | Fleischer |
| 6,296,624 B1 | 10/2001 | Gerber et al. |
| 6,298,256 B1 | 10/2001 | Meyer |
| 6,363,273 B1 | 3/2002 | Mastrorio et al. |
| 6,371,943 B1 | 4/2002 | Racz et al. |
| 6,558,353 B2 | 5/2003 | Zohmann |
| 6,572,593 B1 | 6/2003 | Daum |
| 6,592,559 B1 | 7/2003 | Pakter et al. |
| 6,610,066 B2 | 8/2003 | Dinger et al. |
| 6,620,180 B1 | 9/2003 | Bays et al. |
| 6,638,238 B1 | 10/2003 | Weber et al. |
| 6,641,563 B1 | 11/2003 | Vitullo et al. |
| 6,709,418 B1 | 3/2004 | Aboul Hosn et al. |
| 6,712,773 B1 * | 3/2004 | Viola ................. 600/564 |
| 6,764,491 B2 | 7/2004 | Frey et al. |
| 6,872,199 B2 * | 3/2005 | Cucin ................. 604/542 |
| 6,899,712 B2 | 5/2005 | Moutafis et al. |
| 6,923,813 B2 | 8/2005 | Phillips et al. |
| 6,925,333 B2 | 8/2005 | Krebs |
| 6,979,317 B2 | 12/2005 | Galt et al. |
| 7,022,109 B1 | 4/2006 | Ditto |
| 7,120,487 B2 | 10/2006 | Nelson |
| 7,181,289 B2 | 2/2007 | Pflueger et al. |
| 7,234,468 B2 | 6/2007 | Johnson et al. |
| 7,244,263 B2 | 7/2007 | Robison et al. |
| 7,318,831 B2 | 1/2008 | Alvarez et al. |
| 7,400,930 B2 | 7/2008 | Sharkey et al. |
| 7,465,278 B2 | 12/2008 | Cicenas et al. |
| 7,632,294 B2 | 12/2009 | Milbodker et al. |
| 7,647,123 B2 | 1/2010 | Sharkey et al. |
| 7,727,186 B2 | 6/2010 | Makower et al. |
| 7,740,631 B2 | 6/2010 | Bleich et al. |
| 7,806,834 B2 | 10/2010 | Beckman et al. |
| 7,819,819 B2 | 10/2010 | Quick et al. |
| 7,828,748 B2 | 11/2010 | Hibner |
| 7,854,706 B2 | 12/2010 | Hibner |
| 7,909,822 B2 | 3/2011 | Guerra |
| 7,918,804 B2 | 4/2011 | Monson et al. |
| 7,955,057 B2 * | 6/2011 | Kuehner et al. ................. 417/360 |
| 8,016,846 B2 | 9/2011 | McFarlin et al. |

| | | |
|---|---|---|
| 8,088,119 B2 | 1/2012 | Saal et al. |
| 2002/0183758 A1 | 12/2002 | Middleton et al. |
| 2003/0176778 A1 | 9/2003 | Messing et al. |
| 2003/0212395 A1 | 11/2003 | Woloszko et al. |
| 2004/0034339 A1 | 2/2004 | Stoller et al. |
| 2004/0049217 A1 | 3/2004 | Ross et al. |
| 2004/0064127 A1 | 4/2004 | Lerner |
| 2004/0092992 A1 | 5/2004 | Adams et al. |
| 2004/0098006 A1 | 5/2004 | Nakanishi |
| 2004/0102760 A1 | 5/2004 | Hsue et al. |
| 2004/0127963 A1 | 7/2004 | Uchida et al. |
| 2004/0210231 A1 | 10/2004 | Boucher et al. |
| 2004/0267282 A1 | 12/2004 | Shkarubo et al. |
| 2005/0004563 A1 | 1/2005 | Racz et al. |
| 2005/0010205 A1 | 1/2005 | Hovda et al. |
| 2005/0090801 A1 | 4/2005 | Racz et al. |
| 2005/0197661 A1 | 9/2005 | Carrison et al. |
| 2005/0203527 A1 | 9/2005 | Carrison et al. |
| 2005/0234425 A1 | 10/2005 | Miller et al. |
| 2005/0261692 A1 | 11/2005 | Carrison et al. |
| 2006/0004369 A1 | 1/2006 | Patel et al. |
| 2006/0064101 A1 | 3/2006 | Arramon |
| 2006/0110017 A1 | 5/2006 | Tsai et al. |
| 2006/0111728 A1 | 5/2006 | Abdou |
| 2006/0129062 A1 | 6/2006 | Nicoson et al. |
| 2006/0229550 A1 | 10/2006 | Staid et al. |
| 2006/0239982 A1 | 10/2006 | Simpson |
| 2006/0258951 A1 | 11/2006 | Bleich et al. |
| 2006/0264994 A1 | 11/2006 | Schomer et al. |
| 2006/0271196 A1 | 11/2006 | Saal et al. |
| 2006/0271197 A1 | 11/2006 | Saal et al. |
| 2006/0284994 A1 | 12/2006 | Kim |
| 2007/0055259 A1 | 3/2007 | Norton et al. |
| 2007/0149895 A1 * | 6/2007 | McCullough et al. ........ 600/566 |
| 2007/0162062 A1 | 7/2007 | Norton et al. |
| 2008/0183175 A1 | 7/2008 | Saal et al. |
| 2008/0183192 A1 | 7/2008 | Saal et al. |
| 2008/0188826 A1 | 8/2008 | Saal |
| 2008/0188827 A1 | 8/2008 | Saal |
| 2008/0221586 A1 | 9/2008 | Garcia-Bengochea et al. |
| 2008/0221589 A1 | 9/2008 | Balling et al. |
| 2008/0221605 A1 | 9/2008 | Saal et al. |
| 2008/0255563 A1 | 10/2008 | Farr et al. |
| 2008/0294166 A1 | 11/2008 | Goldin et al. |
| 2008/0294167 A1 | 11/2008 | Schumacher et al. |
| 2009/0048678 A1 | 2/2009 | Saal et al. |
| 2009/0076486 A1 | 3/2009 | Cucin |
| 2009/0216234 A1 | 8/2009 | Farr et al. |
| 2009/0259126 A1 | 10/2009 | Saal et al. |
| 2010/0152611 A1 | 6/2010 | Parihar et al. |
| 2011/0054349 A1 | 3/2011 | Hibner |
| 2011/0098596 A1 | 4/2011 | Ozturk et al. |
| 2011/0306879 A1 | 12/2011 | Saal et al. |

FOREIGN PATENT DOCUMENTS

| | | |
|---|---|---|
| WO | WO 2008/094436 | 8/2008 |
| WO | WO 2008/094444 | 8/2008 |
| WO | WO 2008/094439 | 9/2008 |
| WO | WO 2008/095177 | 10/2008 |
| WO | WO 2009/052194 | 4/2009 |
| WO | WO 2009/124192 | 10/2009 |
| WO | WO 2012/003383 | 1/2012 |

* cited by examiner

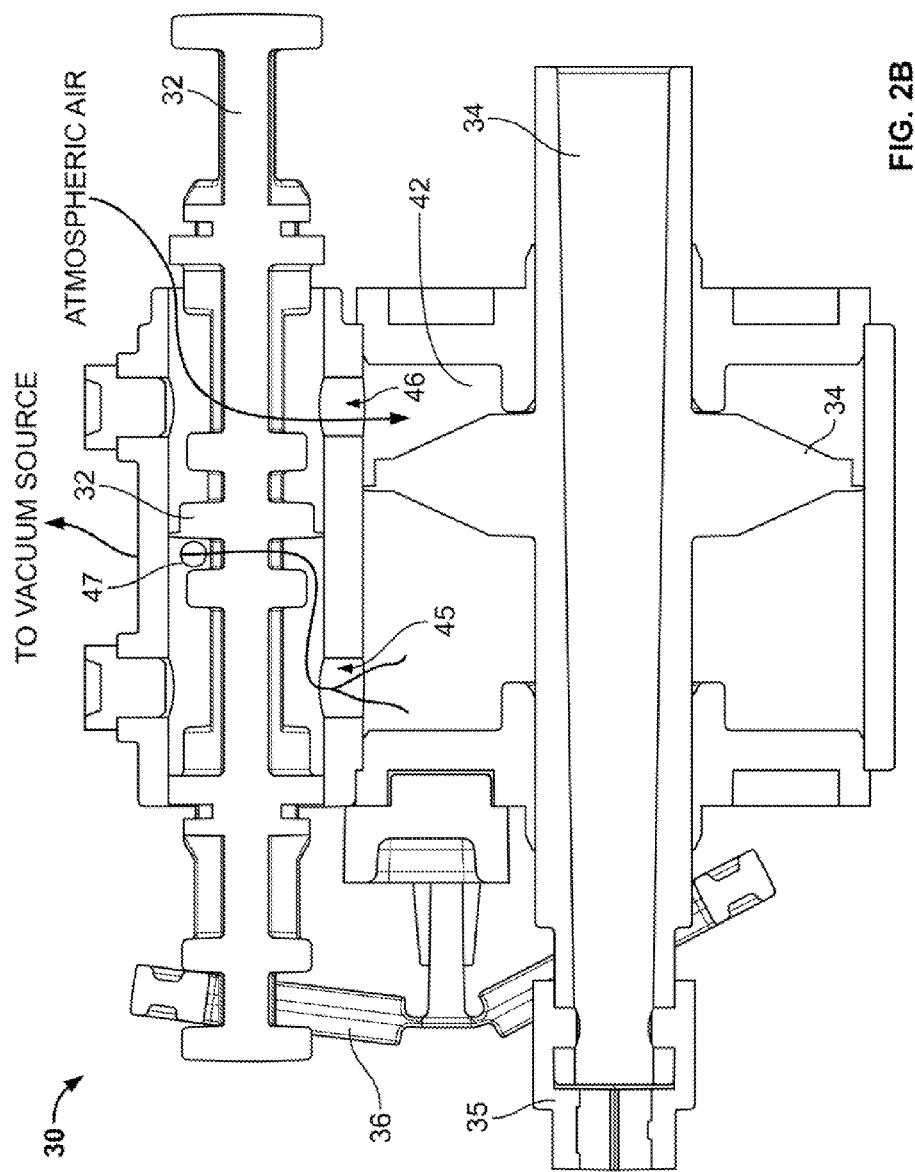

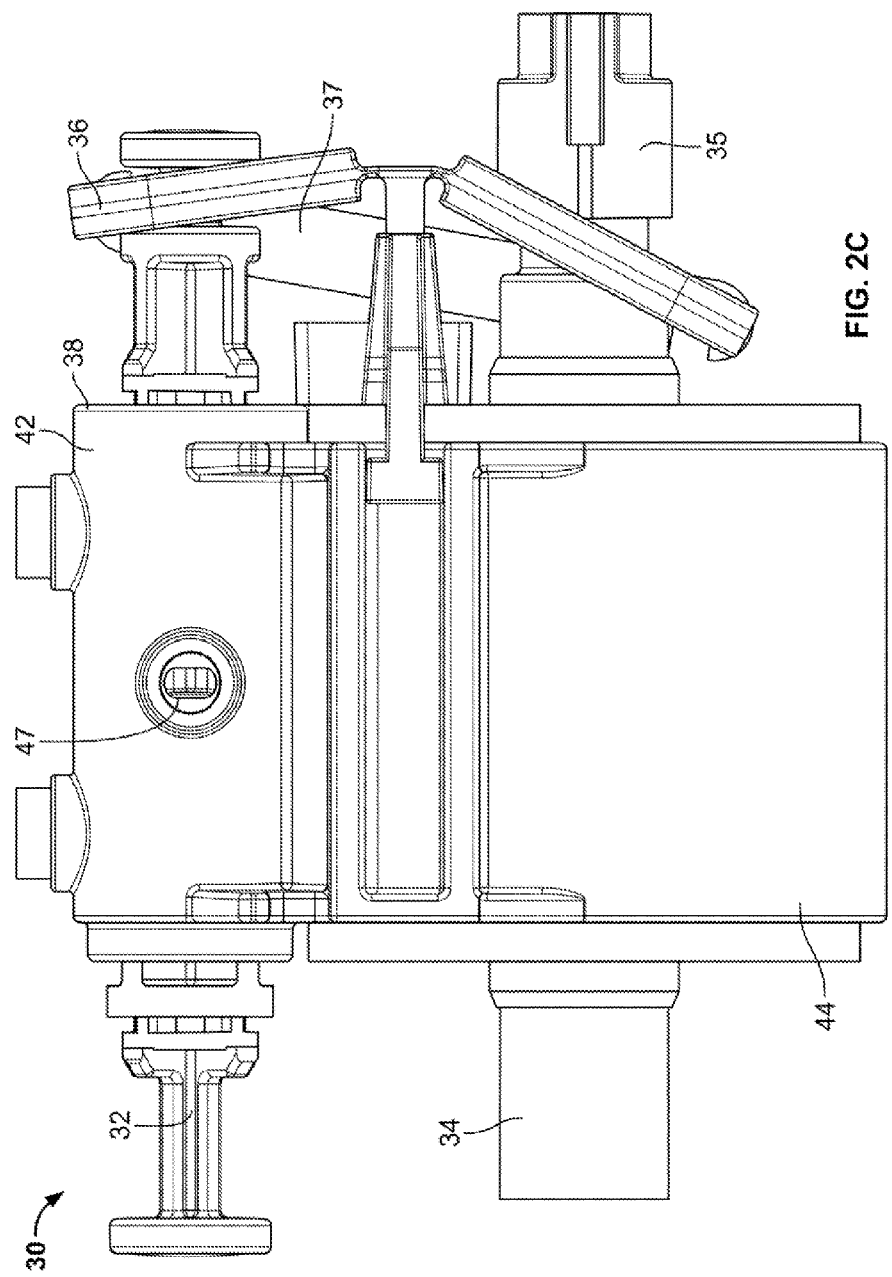

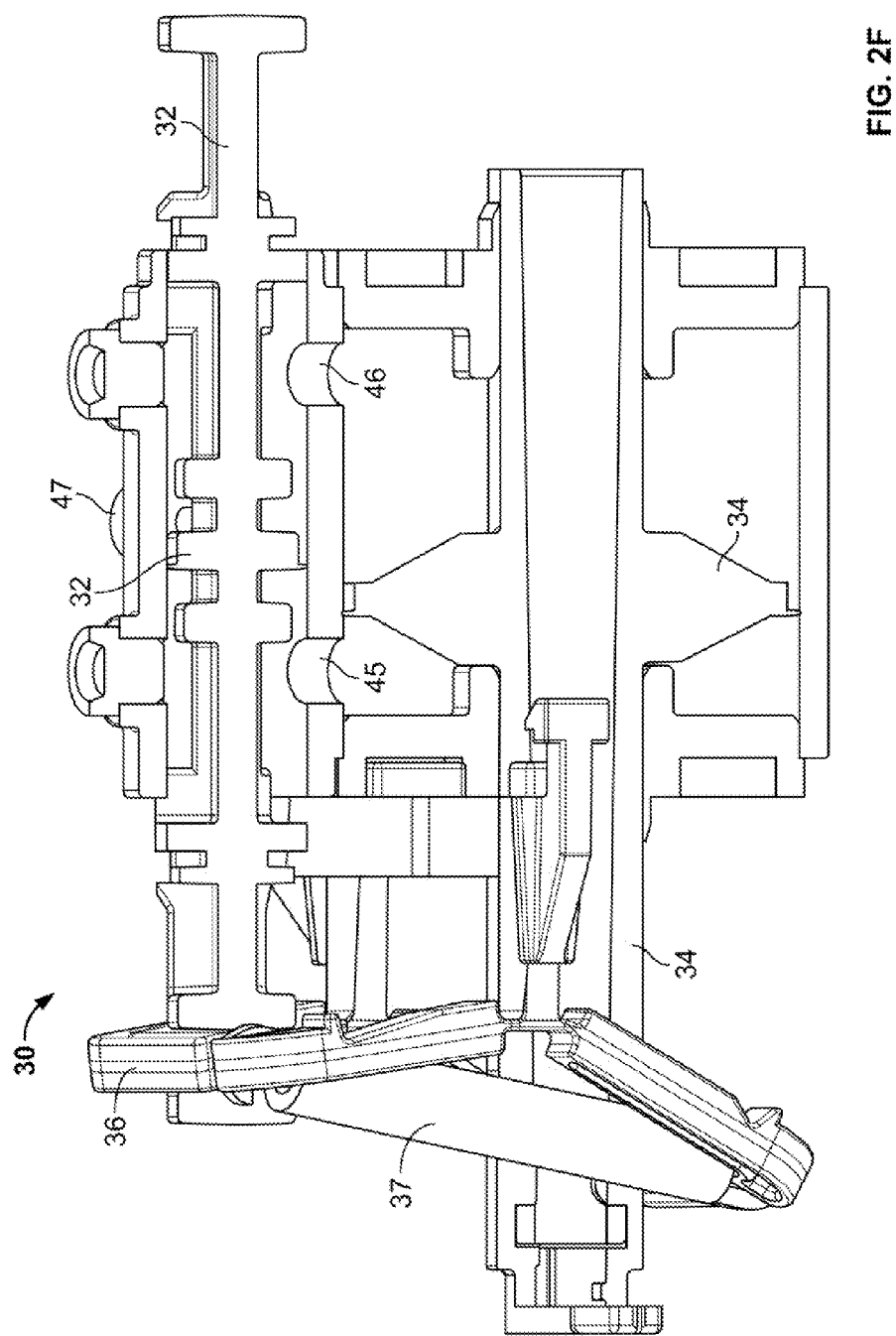

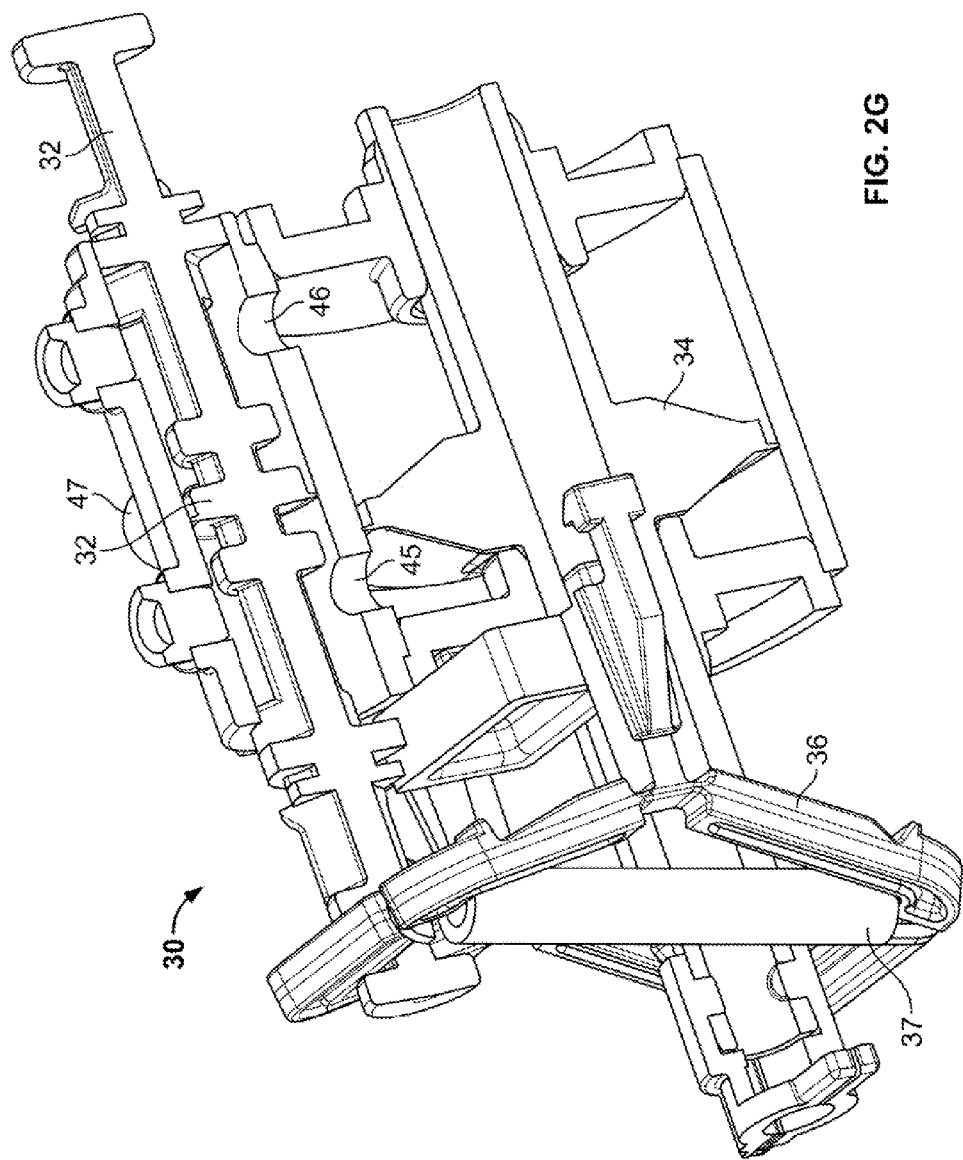

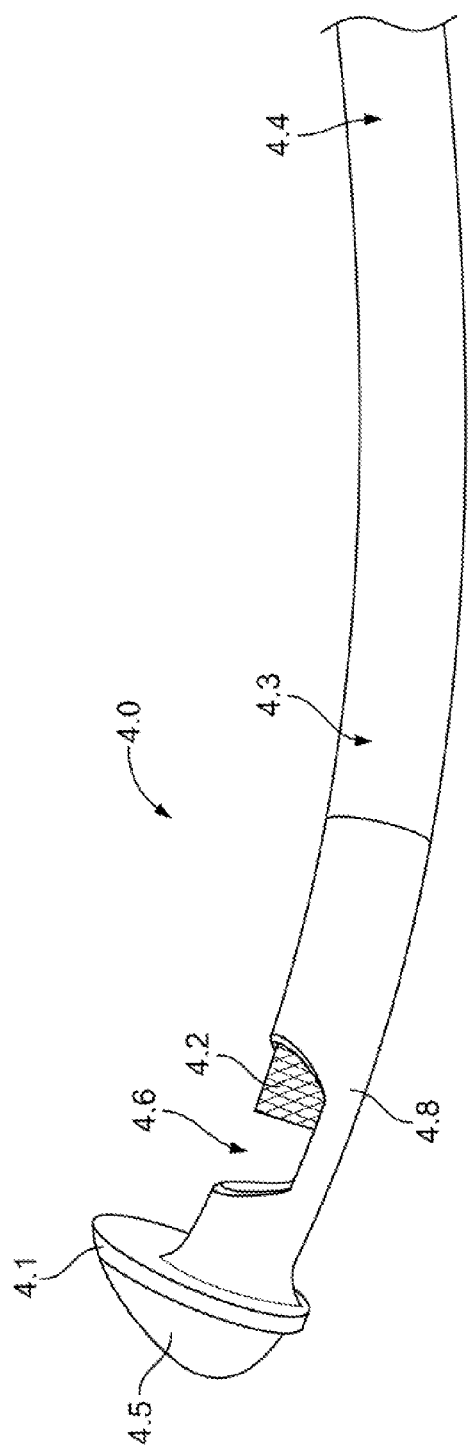

advancing a cutting device next to a target tissue in the subject, the cutting device having a an elongate shaft and a cutter positioned within the elongate shaft

powering the cutting device using suction created by a vacuum source such that the cutting device produces a reciprocating motion which causes the cutter to reciprocate

cutting tissue with the reciprocating cutter

evacuating the cut tissue using the suction created by the vacuum source

Fig. 8

DEVICES AND METHODS FOR CUTTING AND EVACUATING TISSUE

CROSS-REFERENCE TO RELATED APPLICATIONS

The present application claims benefit of priority to U.S. Provisional Patent Application Ser. No. 61/360,429 filed Jun. 30, 2010 and U.S. Provisional Patent Application Ser. No. 61/377,883 filed Aug. 27, 2010 both of which are incorporated by reference herein in their entirety for all purposes.

FIELD OF THE INVENTION

The present devices and methods relate generally to medical devices and methods for cutting and/or evacuating tissue from various regions of a patient's body.

BACKGROUND

Many common medical devices perform the function of resecting tissue. Suction, supplied by an external vacuum source is often used to evacuate tissue from the operative site.

Medical devices which cut and evacuate tissue are used in a variety of procedures, including ear, nose, and throat surgery, gynecological surgery, spinal surgery, ophthalmic surgery, and many other applications. Depending on the procedure, the evacuated tissue may be collected for pathological analysis.

When applied to ear, nose, and throat surgery, tissue resecting devices are commonly referred to as microdebriders.

Tissue incision may be performed by either a rotating cutter (unidirectional or oscillating) or a reciprocating cutter. In the case of a rotating cutter, an electric motor is commonly used as the source of motion. In the case of a reciprocating cutter, motion may be produced by manual actuation, through a control such as a button or trigger, or powered actuation using pulsed or valved compressed air. Each of these power sources has distinct disadvantages when used to power a resecting medical device.

For example, when an electric motor is used to provide rotational motion of a cutter, the additional weight of the electric motor may cause operator fatigue. Wires from an external power supply are inconvenient to make the connections and it is inconvenient to have the wires attached to the device during use.

An electric motor increases the total cost of a device because of the relatively high cost of the motor itself and the cost of a power supply (in the case of an externally powered motor) or the cost of a recharging unit (when rechargeable batteries are used). The addition of electric motors makes sterilization of the device more difficult, e.g., because of the added mass to the device from the motors. Additionally, the presence of batteries reduces the sterilization options available to the manufacturer, due to the heat generated by certain sterilization techniques. The presence of batteries adds potentially toxic chemicals that present additional challenges related to toxicity, sterilization, and device disposal.

Medical devices that include electric motors are often made to be re-usable which requires a system for reprocessing the device. When using a manually actuated cutting device, the operator may experience fatigue from repeated actuations. Additionally, manual actuations can be performed only as quickly as the operator can actuate the cutter via mechanical input through a control and the time required to perform an adequate number of actuations may be excessive.

Electrically-powered microdebriders typically require an expensive capital investment in a power console that is separate from the handpiece. The capital cost of the power console, handpiece, and disposable blades makes procedures such as a nasal polypectomy and other procedures cost prohibitive in a doctor's clinic setting.

Existing microdebriders are typically built with a handle of the device in line with the shaft of the device, as a result, the handle and the operator's hand may interfere with an endoscope and/or the camera.

Existing microdebriders expose a cutting blade to the end of the device. This may be disadvantageous when the operator loses sight of the end of the device and accidentally cuts or damages structures that come into contact with it.

As a result of these limitations, it is impractical for Ear, Nose, and Throat physicians to remove nasal and sinus polyps or other tissue in an office or other setting using the current technology. Therefore, patients are left with the undesirable options of a course of steroid treatments to reduce the size of the polyps (with associated steroid side effects), removal of the polyps in an ambulatory surgery center (cost prohibitive and therefore rarely performed as a stand-alone procedure), or leaving the polyps untreated and dealing with the associated breathing obstruction.

BRIEF SUMMARY

Various medical devices and methods for cutting and/or evacuating tissue from various regions of a patient's body are provided herein Various cutting device driven by various power sources are described herein. In certain variations, a vacuum powered tissue cutting device is provided. The device may include an elongate shaft having a proximal end, a distal end and a lumen defined therein. The distal end may include an opening for receiving tissue. A cutter may be positioned within the elongate shaft, wherein the cutter is configured to be actuated to cut tissue. A chamber may be coupled to the proximal end of the elongate shaft. For example, the chamber may be coupled to the elongate shaft such that the elongate shaft remains fixed relative to the chamber. The chamber may have a mechanism positioned therein, wherein the mechanism can be powered by suction created by a vacuum source such that the mechanism produces an actuating motion which causes the cutter to actuate, e.g., to reciprocate. In certain variations, a cutter positioned within the elongate shaft may be reciprocated past the opening in the elongate shaft to cut tissue in the opening.

In certain variations, a method of cutting and/or removing tissue from a subject may include advancing a cutting device next to, near or to a target tissue in the subject. The cutting device may have an elongate shaft and a cutter positioned within the elongate shaft. The cutting device may be powered using suction created by a vacuum source such that the cutting device produces an actuating motion, which causes the cutter to actuate, e.g., reciprocate, to cut tissue. The cut tissue may be evacuated using the suction created by the vacuum source or may be otherwise removed. In certain variations, the method of cutting and/or removing tissue may be utilized to perform a polypectomy or a discectomy.

In certain variations, an apparatus for cutting or scraping tissue in a subject may be provided. The apparatus may include an end effector, wherein the end effector includes a scraping edge positioned on a distal end of the end effector. One or more scraping wings may be positioned at an angle relative to the scraping edge such that the scraping edge and scraping wings may be used to provide scraping motions in different directions.

In certain variations, devices, systems and methods for excising, cutting and/or evacuating tissue are provided. A variation of a device may include a cutter and a double action vacuum powered mechanism or motor in which vacuum is used to actively reciprocate a piston connected to the cutter. The vacuum powered motor may include a vacuum port connected to a vacuum source, a shuttle piston, a drive piston coupled to the shuttle piston, and a chamber for receiving the drive piston, the chamber having proximal and distal sides. The drive piston may be set into reciprocating motion through the creation of differential pressure on either side of the piston by alternating evacuation, through the vacuum port, within the two sides of the piston chamber. The motion of the drive piston may effect translation of the shuttle piston, causing the shuttle piston to alternate between positions of opening and closing the vacuum port to the proximal and distal sides of the piston chamber to alternate evacuation of each side of the chamber. The actuating motion, e.g., reciprocating motion, of the drive piston may be used to reciprocate or rotate the cutter.

In certain variations, a cutting or scraping component may be positioned or located at or near a distal end of a rigid or flexible end effector which may be utilized to excise, scrape or cut tissue. The end effector may be curved or straight. The end effector may include a shaft, a reciprocating cutter and/or a scraping edge positioned on the shaft or on the reciprocating cutter.

In certain variations, a cutter may be positioned at or near the distal end of a malleable shaft that may be shaped by the operator to a curvature suitable to access the desired anatomical location.

BRIEF DESCRIPTION OF THE SEVERAL VIEWS OF THE DRAWINGS

FIG. 2B illustrates a cross sectional view of the vacuum powered mechanism of FIG. 2A.

FIG. 2C illustrates an opposite side view of the vacuum powered mechanism of FIG. 2A.

FIGS. 2F-2G illustrate side and prospective cross sectional views of the vacuum powered mechanism of FIG. 2A in a first position.

FIG. 6 illustrates a side view of a variation of an end effector.

FIG. 8 illustrates a flow chart of a variation of a method for cutting and removing tissue using a vacuum powered cutting device.

DETAILED DESCRIPTION

Figure 1A:
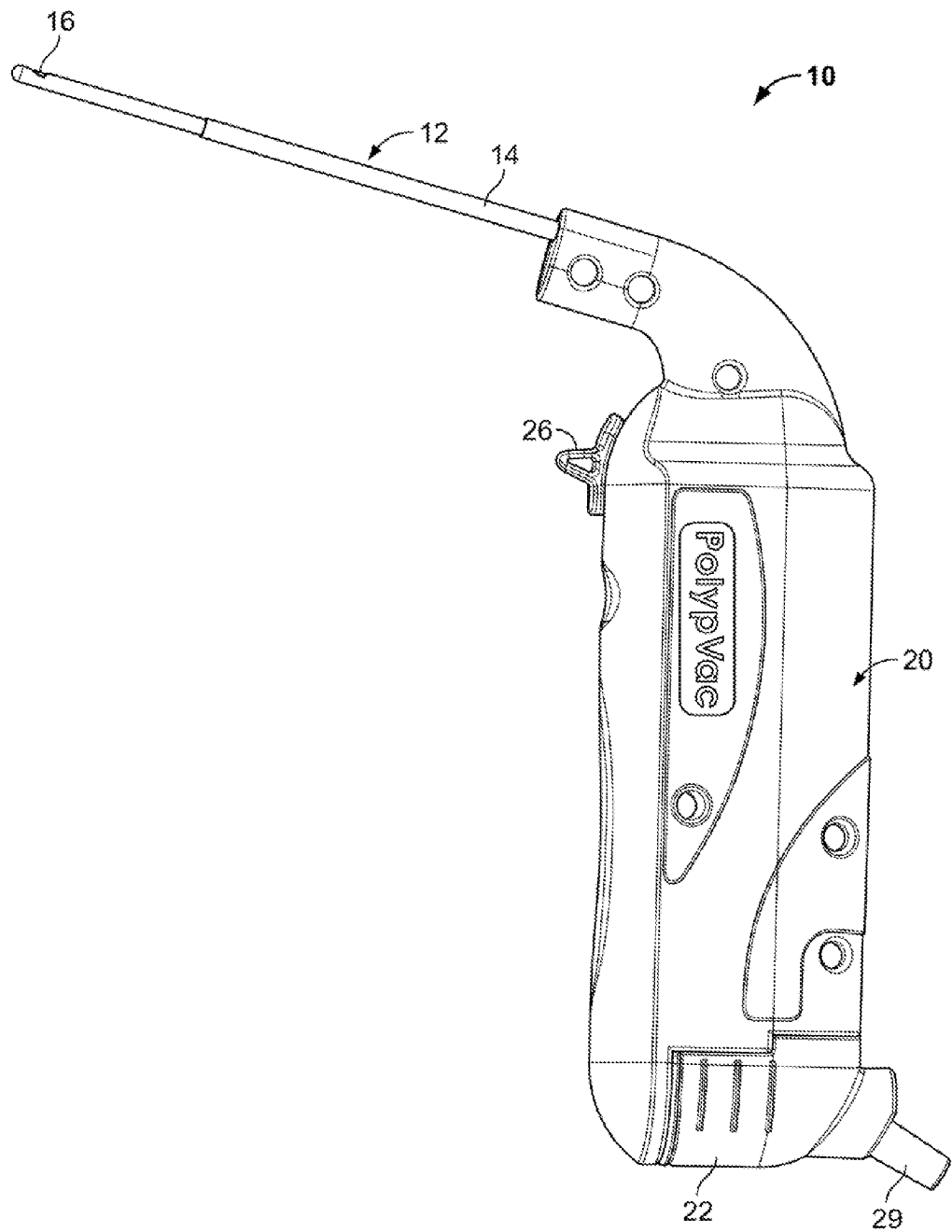
FIG. 1A illustrates a side view of a variation of a cutting device.
Figure 1B:
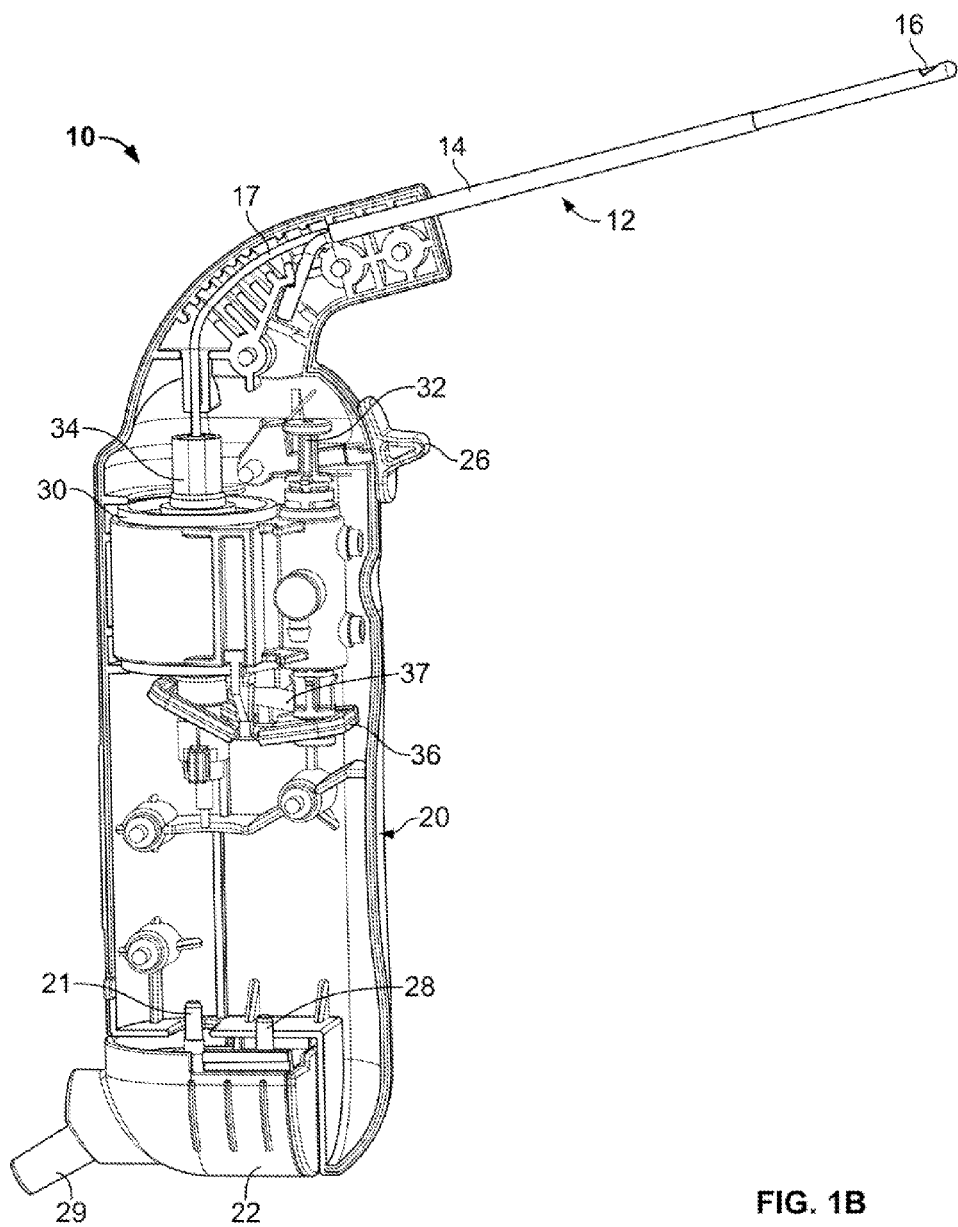
FIG. 1B illustrates a side view of the cutting device of FIG. 1A with the right hand portion of the chamber hidden.
Figure 1C:
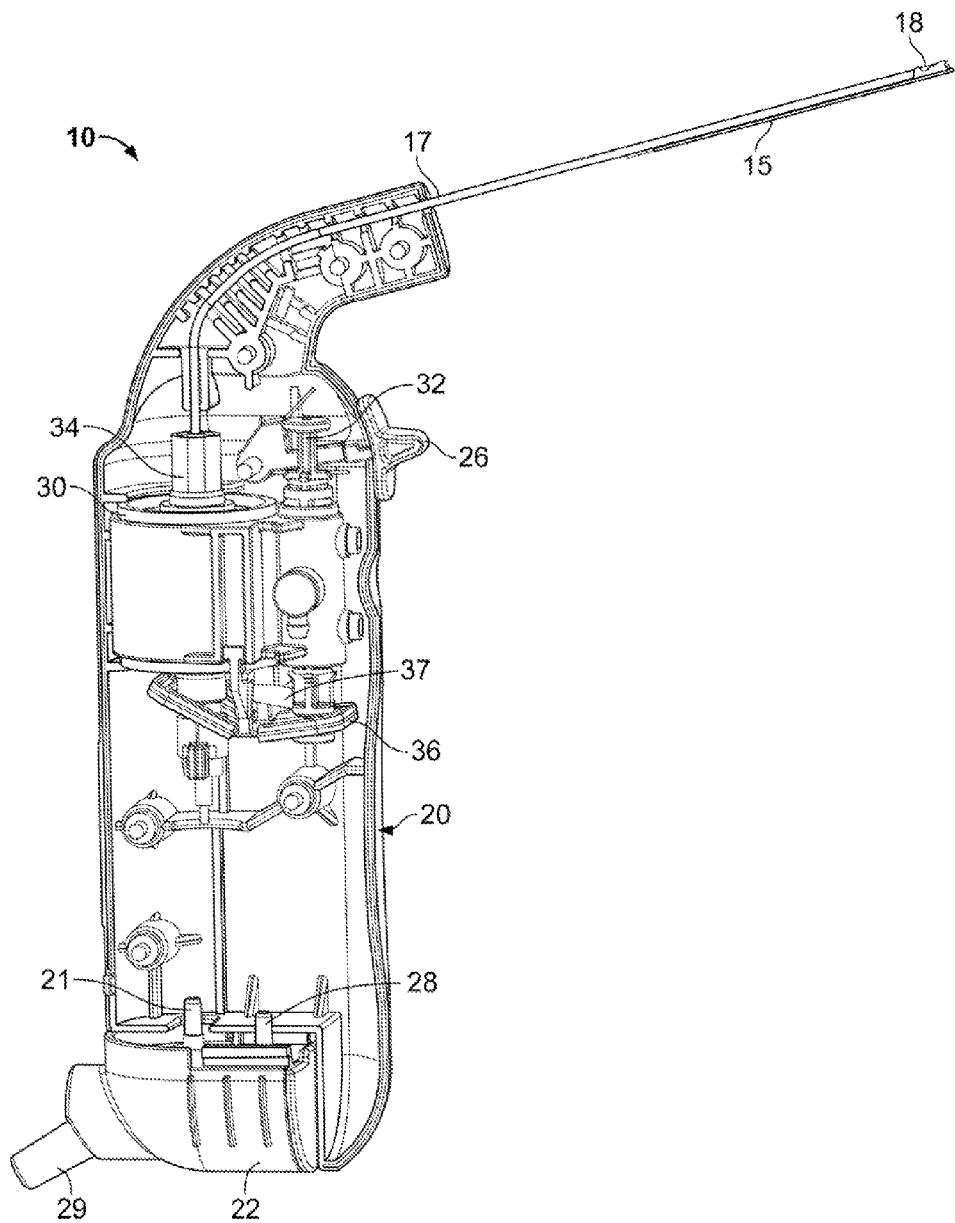
FIG. 1C illustrates a side view of the cutting device of FIG. 1B with the rigid sleeve and elongate shaft hidden to show the evacuation shaft.
Figure 1D:
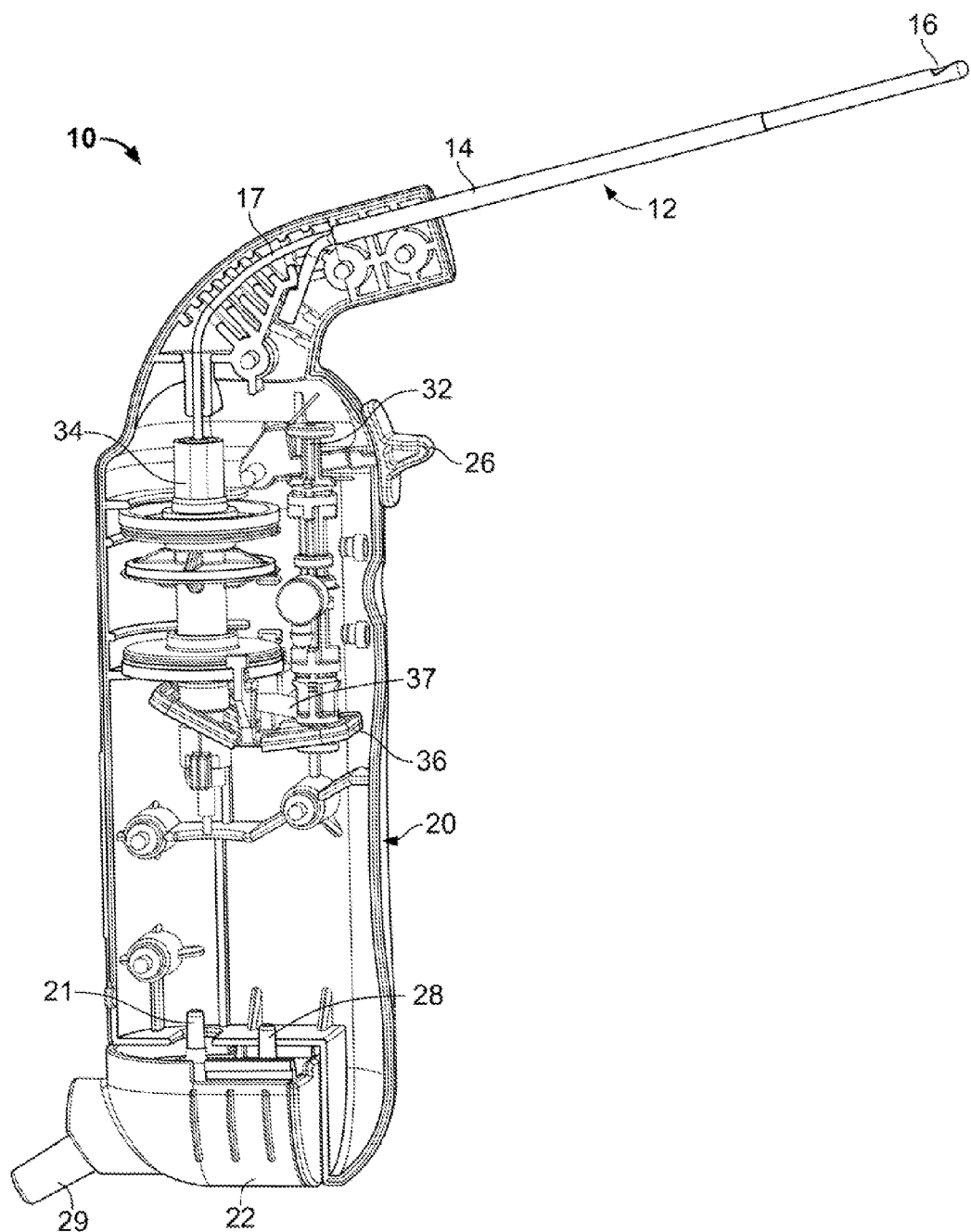
FIG. 1D illustrates a side view of the cutting device of FIG. 1B with the manifold of the vacuum powered mechanism hidden.
Figure 1E:
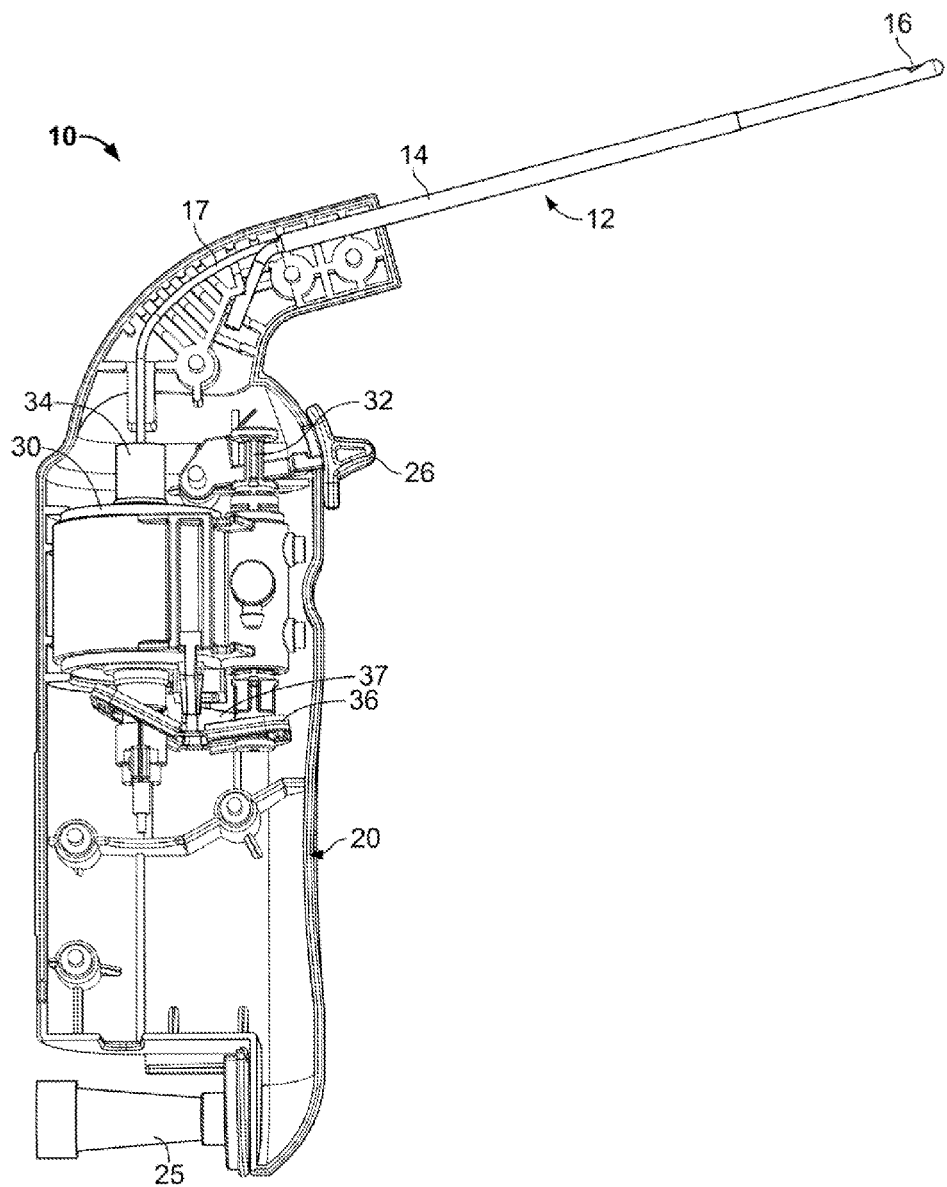
FIG. 1E illustrates a side view of the cutting device of FIG. 1B with the collection chamber hidden to show a filter.

Variations of the devices are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity. The drawings are taken for illustrative purposes only and are not intended to define or limit the scope of the claims to that which is shown.

Various cutting devices and methods for cutting, resecting, incising or excising tissue are described herein. In certain variations a cutting device may include a mechanism or motor driven or powered by a variety of different power sources, e.g., suction from a vacuum source, pneumatic, fluid pressure (e.g. hydraulic), compressed air, battery power or electrical power or gas power or any combination thereof. The mechanism or motor may create a reciprocating or rotational motion output in any direction which causes a cutter on or in the cutting device to actuate, e.g., reciprocate or rotate, to cut tissue. The cutting device may be utilized to cut, resect, incise or excise various types of tissue located in various regions of a patient's body. For example, the cutting device may be utilized to perform a polypectomy in a patient for removal of one or more polyps.

In certain variations, a cutting device powered by suction from a vacuum source (either external or internal) is provided. The cutting device may include an elongate shaft. The elongate shaft may have a proximal end, a distal end and one or more lumens positioned within or along the elongate shaft. The distal end of the elongate shaft may include an opening or window for receiving tissue. The device may include a cutter for cutting tissue. A cutter may be positioned within or on the elongate shaft. The cutter may be actuated, reciprocated, e.g., axially along the longitudinal axis of the elongate shaft, or rotated to cut tissue. A chamber may be coupled to the proximal end of the elongate shaft. The elongate shaft may be coupled to the chamber such that that the elongate shaft or a cannula remains fixed or immovable relative to the chamber, e.g., while the cutter, on or in the elongate shaft or cannula, is being reciprocated or otherwise motivated or during actuation, reciprocation or rotation of the cutter.

A mechanism or motor may be positioned within the chamber. The mechanism may be powered by suction created by a vacuum source, which causes the mechanism to produce a reciprocating motion. In certain variations, the mechanism may be powered solely by suction created by the vacuum source, e.g., without the use of electricity or pressurized air or fluid to power the mechanism. Additional connections for electrical or pneumatic/hydraulic power may not be required. The mechanism may include a piston which is put into reciprocating or reciprocating linear motion by suction from the vacuum source. The reciprocating motion output produced by the mechanism causes the cutter (connected to the mechanism) to actuate, e.g., to reciprocate or to rotate. In certain variations, the cutter may be reciprocated back and forth in a linear motion, e.g., axially, or along the longitudinal axis of the elongate shaft. In other variations, linear reciprocating motion from the mechanism may be translated into rotational motion of the cutter. The cutting device may include a port or valve for connecting the vacuum source to the cutting device to provide suction to the cutting device.

The suction from a vacuum source may draw tissue into the opening in the elongate shaft. The cutter may be reciprocated or rotated past the opening in the elongate shaft, thereby cutting the tissue which is drawn into the opening of the elongate shaft. The cutting device may include an evacuation lumen for evacuating cut tissue using suction created by the vacuum source. In certain variations, the tissue may be otherwise removed without using evacuation to remove the tissue.

In certain variations, a lumen for delivering irrigant or fluid may be provided. For example, the elongate shaft may include a lumen for delivering irrigant to the distal end of an evacuation lumen in the elongate shaft or to an opening of the elongate shaft or to a cutter. The irrigant may flow constantly through the lumen, or it may flow through the lumen only when suction from the vacuum source is present to draw the irrigant through the irrigant lumen. The cutting device may include a reservoir filled with water or other irrigant positioned with the cutting device or the irrigant may be provided from an external supply. For example, a syringe filled with irrigant, e.g., water, may be connected to the cutting device or an elevated container or bag may supply irrigant to the cutting device or to the site of treatment. The irrigant may begin to flow through the cutting device when suction is present in a lumen within the elongate shaft, at an irrigant port, which may be located within the shaft lumen near the opening of the elongate shaft. The irrigant may be drawn to the distal end of an evacuation lumen in the elongate shaft or to the opening of the elongate shaft, where it lubricates tissue and a lumen within the shaft, e.g., a tissue evacuation lumen, to facilitate evacuation of the cut tissue.

The cutting device may include a handle, such that the cutting device may be handheld. For example, the chamber of the cutting device may be in the form of a handle. The handle may be positioned or set at an angle relative to the elongate shaft. This arrangement of the handle or chamber relative to the elongate shaft may provide a clear or substantially clear line of site above and/or to the sides of the elongate shaft. The angled arrangement may reduce interference with other medical devices or instruments that a user may utilize during a tissue cutting procedure, e.g. an endoscope and associated cables. This angled arrangement may also provide optimal user comfort. The handle may have an ergonomic design to provide comfort and ease of use. A curved or angled neck portion may extend from the chamber or handle, for receiving or holding the elongate shaft.

A tissue collection chamber may be provided. For example, a tissue collection chamber may be integrated in the chamber or handle of the cutting device or may be otherwise connected or attached to the cutting device. The tissue collection chamber may be removable from the cutting device. The removable tissue collection chamber may allow tissue collected therein to be biopsied, studied or a diagnosis of pathology may be performed on the collected tissue. Removal of the tissue collection chamber and/or filter may result in the device being disabled, e.g., where the tissue collection chamber may not be reassembled to the device. This may prevent the device from being reused or used on more than one patient to minimize or prevent the associated risks of transmitting pathogens from one patient to another or infecting another patient. For example, the device may be disabled where the internal vacuum lines are sheered when the tissue collection chamber is removed from the handle. As a result, the tissue collection chamber cannot be reassembled to the device thereby rendering the device useless. The device may be fully or partially disposable.

In other variations, a tissue collection chamber may be reusable, where the tissue collection chamber may be removed, sterilized and then reassembled or reattached to the cutting device for continued use.

Various configurations of the elongate shaft are contemplated. In certain variations, at least a portion of the elongate shaft or the entire elongate shaft may be malleable or otherwise adjustable. For example, the distal end of the elongate shaft or the section of the elongate shaft where tissue cutting is performed may be malleable or flexible such that portion of the elongate shaft may be adjusted or manipulated by the user, e.g., hand adjustable. The malleable portion of the elongate shaft may be manipulated into a variety of shapes or curves such that the cutting device, e.g., the cutter or cutter opening, may access or be positioned in a variety of anatomical locations to cut and/or remove tissue. The malleable portion of the elongate shaft may be adjusted or manipulated before or during operation by the user into various positions or configurations, ranging from, straight to angled or curved. The shaft may be manually, automatically or robotically adjusted. The shaft may be adjusted without the need for additional tools or attachments to change or affect the shape or position of the shaft, such that the positioning for cutting and cutting may be performed using a single device. In other variations, a tool or attachment may optionally be utilized to adjust or manipulate an elongate shaft for cutting.

A cutter may have various shapes and configuration, e.g., the cutter may be in the form of a cutting blade or pipe or tube positioned within the elongate shaft. A cutter may be positioned in the cutting device such that the cutter can reciprocate past an opening or cutting window in the elongate shaft. In certain variations, the cutter may be positioned within or on the elongate shaft such that the cutting blade is not exposed on an outside of the opening or window in the elongate shaft or beyond the distal tip of the elongate shaft. This arrangement may provide safety to patients and minimize or prevent the risk of inadvertently cutting or puncturing tissue in a patient during the tissue cutting procedure or during advancement of the cutting device to the target site in a patient for treatment.

In certain variations, the anvil may protect a cutter such that it is not exposed, thereby providing safety to patients.

A sufficient vacuum source for operating or powering any of the cutting devices described herein may be the vacuum source provided in most standard operating rooms, physician's offices, clinics or outpatient surgery centers. For example, many physicians' offices have vacuum pumps capable of generating vacuum in the ranges of 10 to 25 inches of mercury (in HG), e.g., about 22 inches of mercury (in Hg) and/or at about 28 to about 40 liters per minute (LPM) flow rate. The various cutting devices described herein may utilize vacuum sources or vacuum pumps operating in the above performance ranges to effectively operate and cut tissue without additional power inputs or supply requirements needed. For example, suction provided by such vacuum sources may move, actuate, reciprocate or otherwise operate the mechanism of a cutting device and/or the cutter at a speed or rate ranging from about 250 to about 2500 cycles/min or about 500 to 1200 cycles per minute or less than about 1200 cycles per minute. These rates are slower than the rates that would be provided by a typical electrically powered motor, yet provide the control and power to effectively and safely operate and reciprocate the cutter of the cutting devices described herein to cut, resect, and/or excise tissue in various regions in a patient, e.g., to cut and remove polyps positioned in the nasal or sinus cavity of a patient in a safe, controlled and effective manner.

In certain variations, a cutting device may be connected solely to a vacuum source, and optionally, to an irrigant source. The vacuum source may be connected to the cutting device such that suction supplied by the vacuum source drives or powers the mechanism of the cutting device, draws tissue into the opening in the elongate shaft or otherwise into the path of a cutter, draws irrigant from a reservoir or other source through the cutting device or through a lumen in or on the cutting device, or to the cutting device and/or evacuates cut tissue for removal from a patient.

Various vacuum powered mechanism for use in the various cutting devices described herein, to drive or actuate a cutter, are also described herein. In certain variations, a vacuum powered or vacuum driven mechanism may include one or more pistons, wherein suction is applied to both sides of the piston in an alternating manner to cause the piston to reciprocate. The piston is coupled or connected (directly or indirectly) to the cutter, thereby causing the cutter to reciprocate. In another variation, suction may be applied to one side of the piston and a spring force in a vacuum powered mechanism may be applied to the other side of the piston, to cause the piston to reciprocate. The reciprocating piston causes the cutter to reciprocate.

In certain variations, a hand-held, fully disposable powered medical device capable of resecting tissue in the human body is provided. The device is powered by an internal mechanism that is powered by suction from an external vacuum source. The mechanism produces reciprocating motion that may be used to move a cutter back-and-forth past an opening in a shaft. A portion of the suction from the external vacuum source is routed through the shaft and draws tissue into the window where it is excised by the cutter. The tissue is then evacuated through the shaft and into a tissue collection chamber on the handle of the device. The suction in the shaft also draws irrigant into the lumen of the shaft, where it lubricates the tissue and shaft lumen to facilitate evacuation of the tissue.

In certain variations, the cutting devices or mechanisms described herein may be powered by a vacuum source where the devices have an efficient use of supplied vacuum suction to the device, e.g., with none of the supplied suction going unused. In certain variations, a cutting device may be powered by constant delivery of vacuum or suction. In certain variations, a cutting device may be manufactured of all or substantially all mechanical components reducing costs for manufacturing.

In certain variations, a cutter may be positioned at or near the distal end of a flexible shaft that has a preformed or predetermined curvature. The shaft may be adapted for insertion into a cannula where the distal end of the shaft may advance from the cannula toward a target site and where the shaft allows its predetermined curvature to position the distal end of the shaft near the target site.

Exemplary Cutting Devices

FIG. 1A shows one variation of a vacuum powered cutting device. Referring to FIGS. 1B-1E, the cutting device 10 includes an elongate shaft 12. The elongate shaft 12 may include a rigid sleeve 14 that provides rigidity to the elongate shaft. The elongate shaft may include a window or cutting window or opening 16 positioned at or near a distal end of the elongate shaft. An evacuation shaft 17 may be positioned within the elongate shaft 12. A cutter 18 may be positioned within the elongate shaft 12 such that it may be reciprocated past the opening 16. In this particular variation, the cutter 18 is formed at the distal end of the evacuation shaft 17, but other types of cutters are contemplated, e.g., the cutter 18 may extend from a wire or blade positioned in the elongate shaft 12.

Figure 1F:
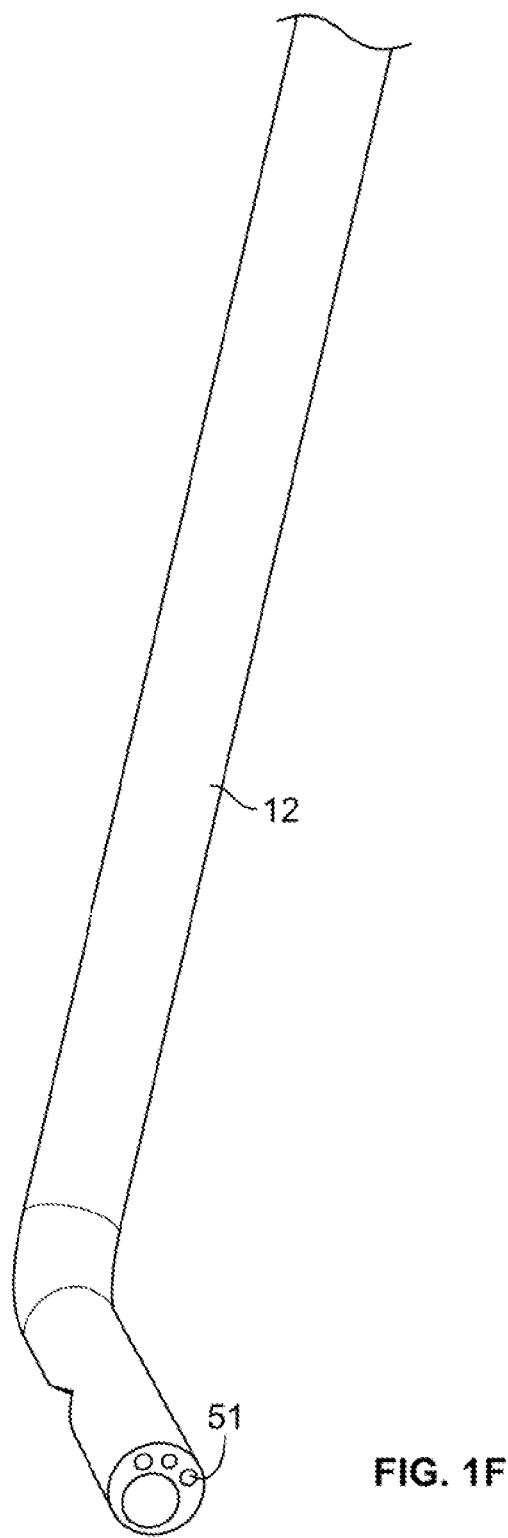
FIG. 1F illustrates a magnified view the elongate shaft of the cutting device of FIG. 1B having multiple lumens.

One or more lumens may be positioned within the elongate shaft 12 (See FIG. 1F). Elongate shaft 12 may include an irrigant lumen. An irrigant line (not shown) may connect to the proximal end 13 of the elongate shaft 12, to supply irrigant from an internal or external reservoir or irrigant source, through an irrigant lumen in the elongate shaft 12, to the distal end of an evacuation lumen in the elongate shaft or to the opening 16 of the elongate shaft 12. For example, the irrigant may be drawn to the opening 16 of the elongate shaft 12, where it lubricates tissue and the evacuation lumen, to facilitate evacuation of the cut tissue. Optionally, the elongate shaft 12 may include a malleable portion, for example at its distal end, which can be manipulated or adjusted to provide various shapes and configurations to the elongate shaft 12 to position a cutter in various regions of the body. Optionally, one or more wires 15 may positioned in the elongate shaft 12, which may serve to hold the malleable portion of the shaft in a desired position. A rigid sleeve 14 may be placed over other portions of the elongate shaft 12 to provide rigidity.

The elongate shaft 12 may extend from a chamber 20. The chamber 20 may provide a handle or grip for a user. The chamber 20 may include a tissue collection chamber 22. The evacuation shaft 17 may extend into the chamber 20, such that one or more lumens of the evacuation shaft 17 empties into the tissue collection chamber 22 either directly or indirectly, e.g., via another tube or pipe (not shown), connecting the evacuation shaft 12 to a first vacuum chamber port 21. The tissue collection chamber 22 may include a filter 25 for filtering tissue collected therein. The tissue collection chamber 22 may be integrated into the chamber 20 such that removal of the tissue collection chamber 22 disables the cutting device 10. In certain variations, the elongate shaft 12 may be coupled or connected to the chamber 20 such that the elongate shaft 12 remains fixed relative to the chamber 20. For example, the elongate shaft 12 may be fixed such that it is not motivated or reciprocated by the mechanism 30 or motor described below.

A vacuum powered mechanism 30 is positioned within the chamber 20. FIGS. 2A-2I show various views of the vacuum powered mechanism 30. The mechanism 30 includes a shuttle piston 32 and a drive piston 34. The pistons may be arranged in various configuration, e.g., in parallel to one another. A bi-stable switch 36 may be connected to the shuttle piston 32 and the drive piston 34. The bi-stable switch 36 having a switch spring 37 may be connected to the drive piston 34 and the shuttle piston 32 either directly or via a piston clamp 35 connected to the switch spring 37 or bi-stable switch 36. Actuation of the bi-stable switch 36 by the drive piston 34, which is motivated or reciprocated by suction created by the vacuum source, may reverse or move the shuttle piston 32 in either the proximal or distal directions (i.e., toward the distal end of the cutting device or toward the proximal end of the cutting device.) When the shuttle piston 32 moves from one end of its' travel extremity to the opposite end of its' travel extremity, the evacuated side of a drive piston chamber 42 is vented to allow atmospheric air to flow into the drive piston chamber 42 while the opposite side of the drive piston chamber 42 is shut off from atmospheric air and evacuated. As a result, the drive piston 34 is motivated to move in the opposite direction until the bi-stable switch 36 is actuated and the shuttle piston 32 reverses. The shuttle piston 32 and the drive piston 34 are positioned in a manifold 38. The manifold 38 includes a drive piston chamber 44 and a shuttle piston chamber 42. The bi-stable switch 36 may ensure a reliable transition of the shuttle piston 32 or valve on the shuttle piston past or completely past a shuttle chamber vacuum supply port 47 to prevent unstable flutter of the shuttle piston 32 and possible mechanism 30 or motor stall.

As shown in the various cross sectional views of FIG. 2B and FIGS. 2F-2I, at least a portion of the drive piston 34 is positioned in the drive piston chamber 44 and at least a portion of the shuttle piston 32 is positioned in shuttle piston chamber 42. The drive piston chamber 44 and the shuttle piston chamber 42 are in fluid communication with each other via first and second vacuum slots 45 and 46.

Figure 1G:
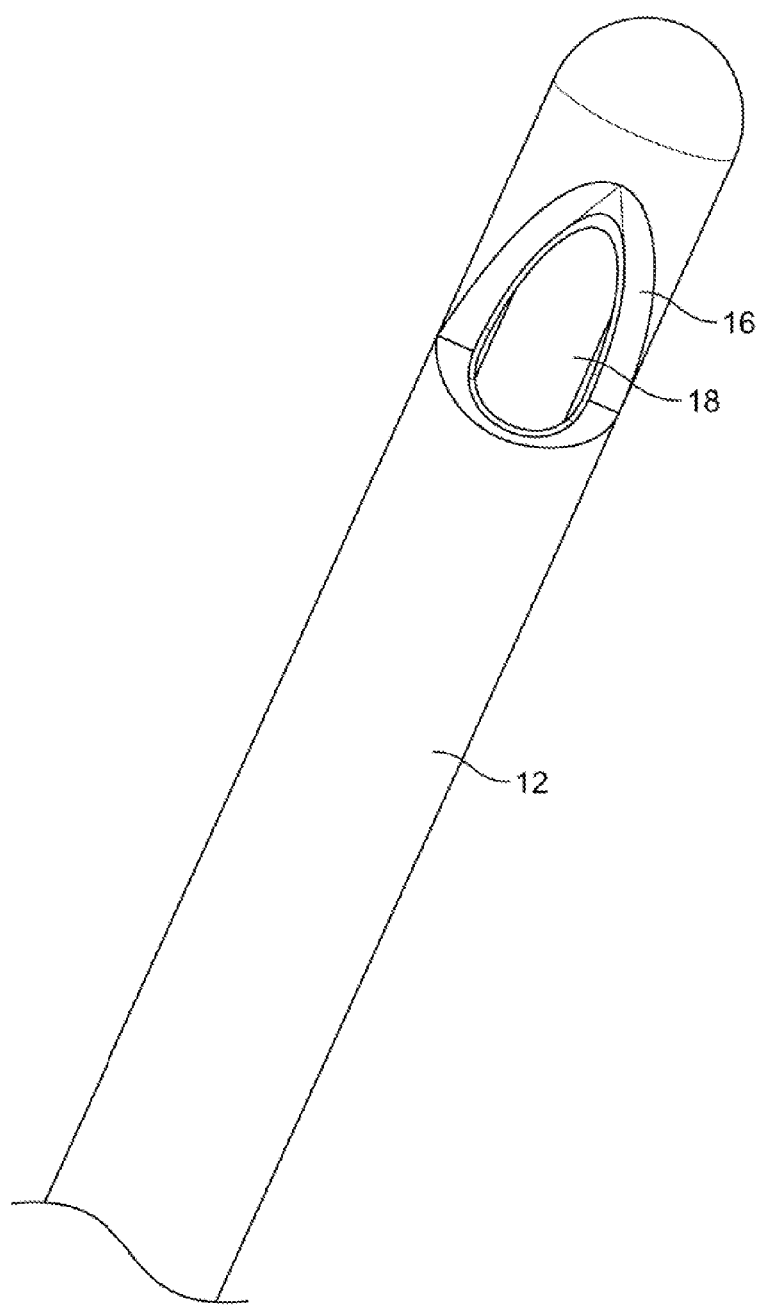
FIG. 1G illustrates a magnified view of the cutter of the cutting device of FIG. 1B.
Figure 1H:
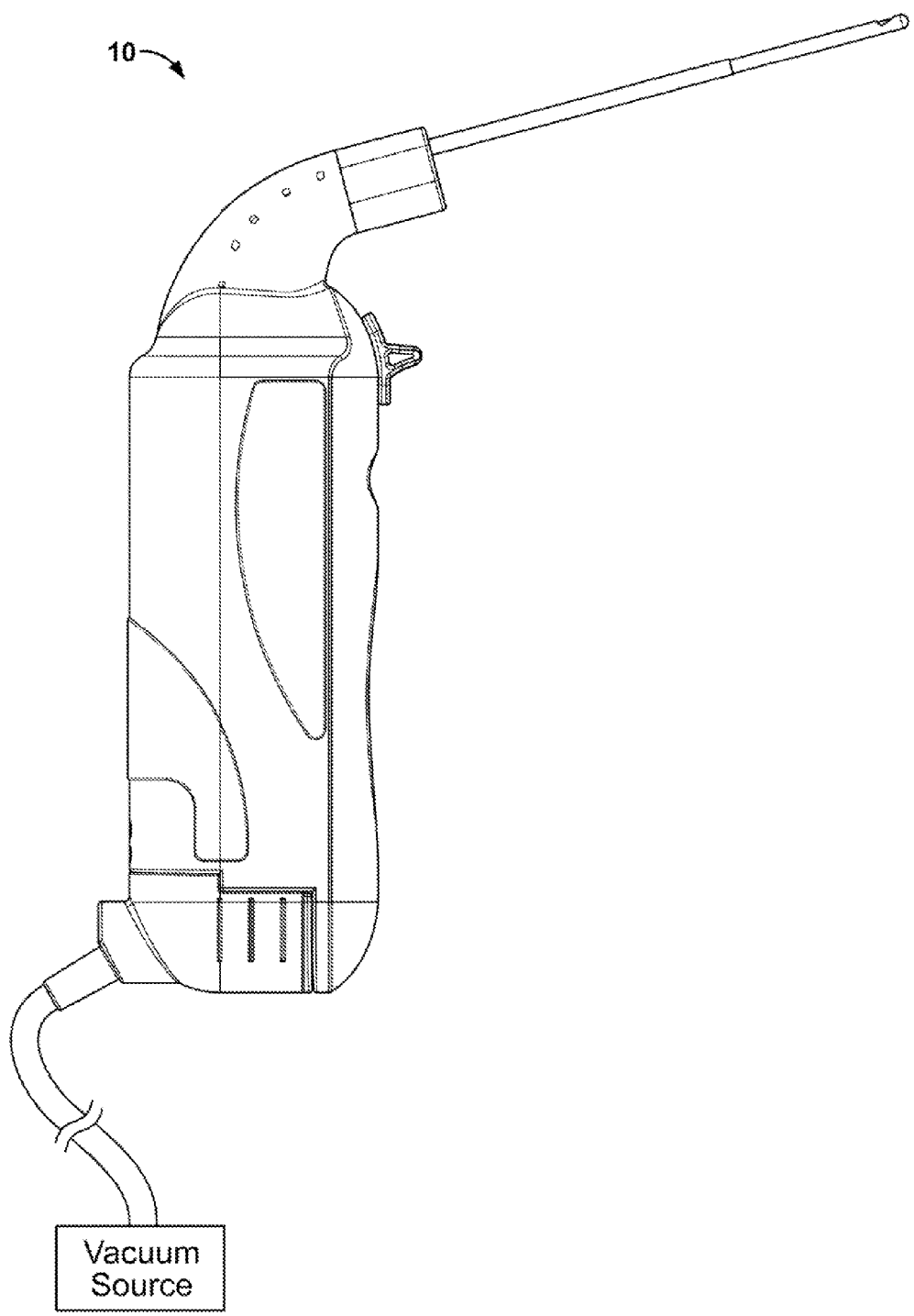
FIG. 1H illustrates a vacuum source coupled to a variation of the cutting device.
Figure 2A:
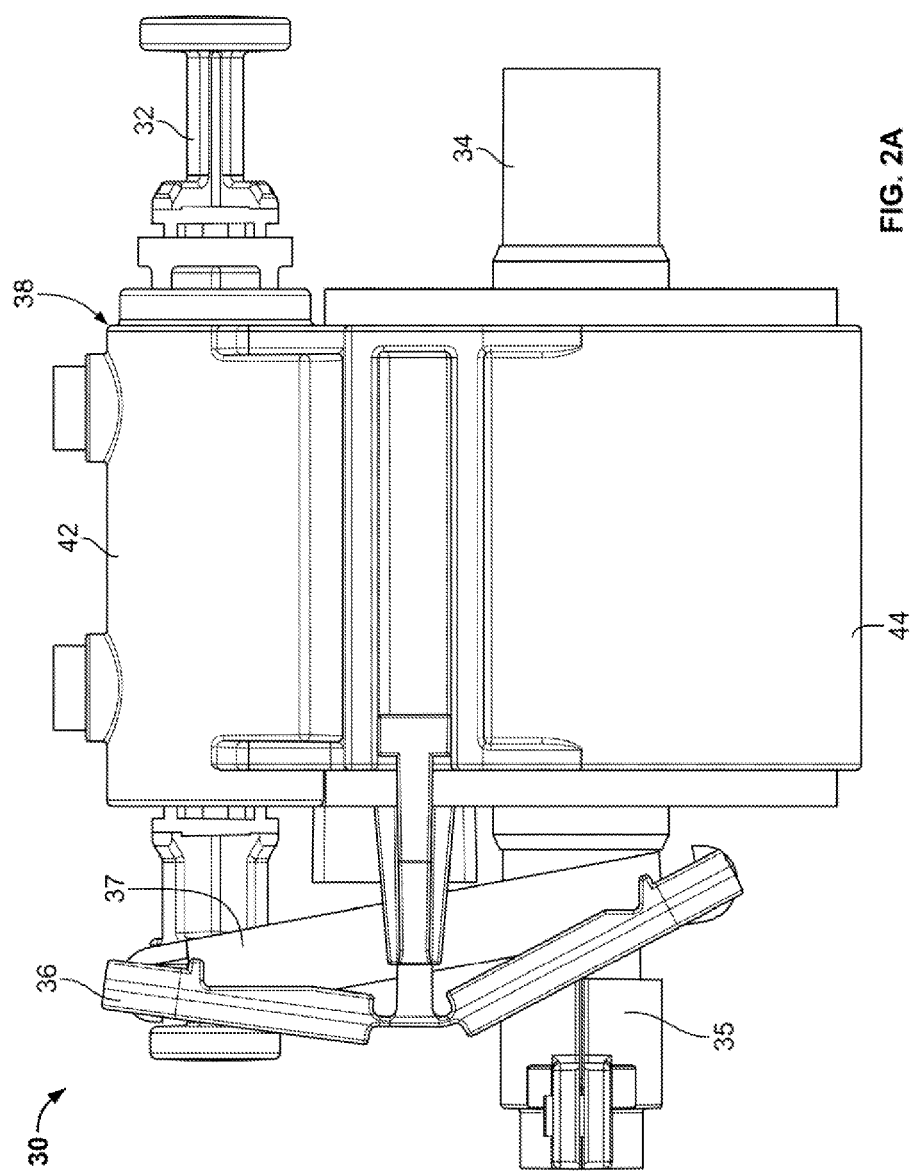
FIG. 2A illustrates a side view of a variation of a vacuum powered mechanism.
Figure 2D:
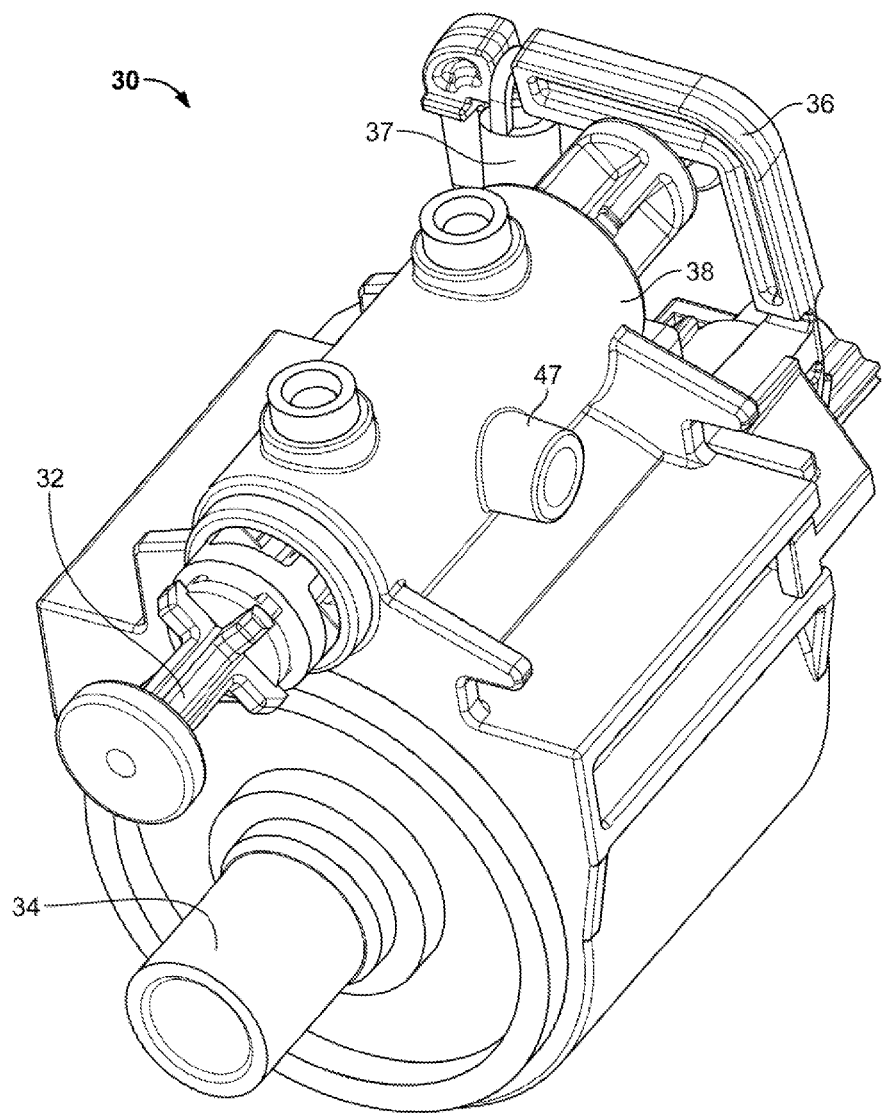
FIG. 2D illustrates a front view of the vacuum powered mechanism of FIG. 2A.
Figure 2E:
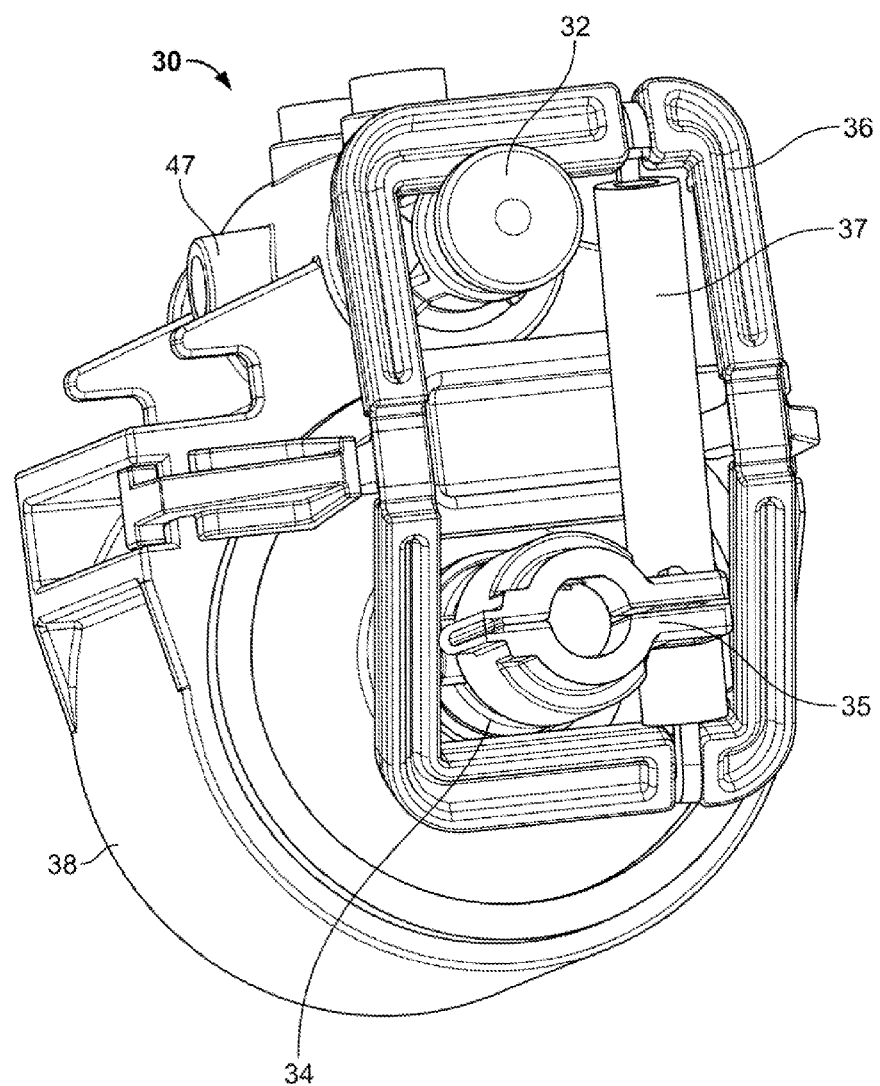
FIG. 2E illustrates a rear view of the vacuum powered mechanism of FIG.
Figure 2H:
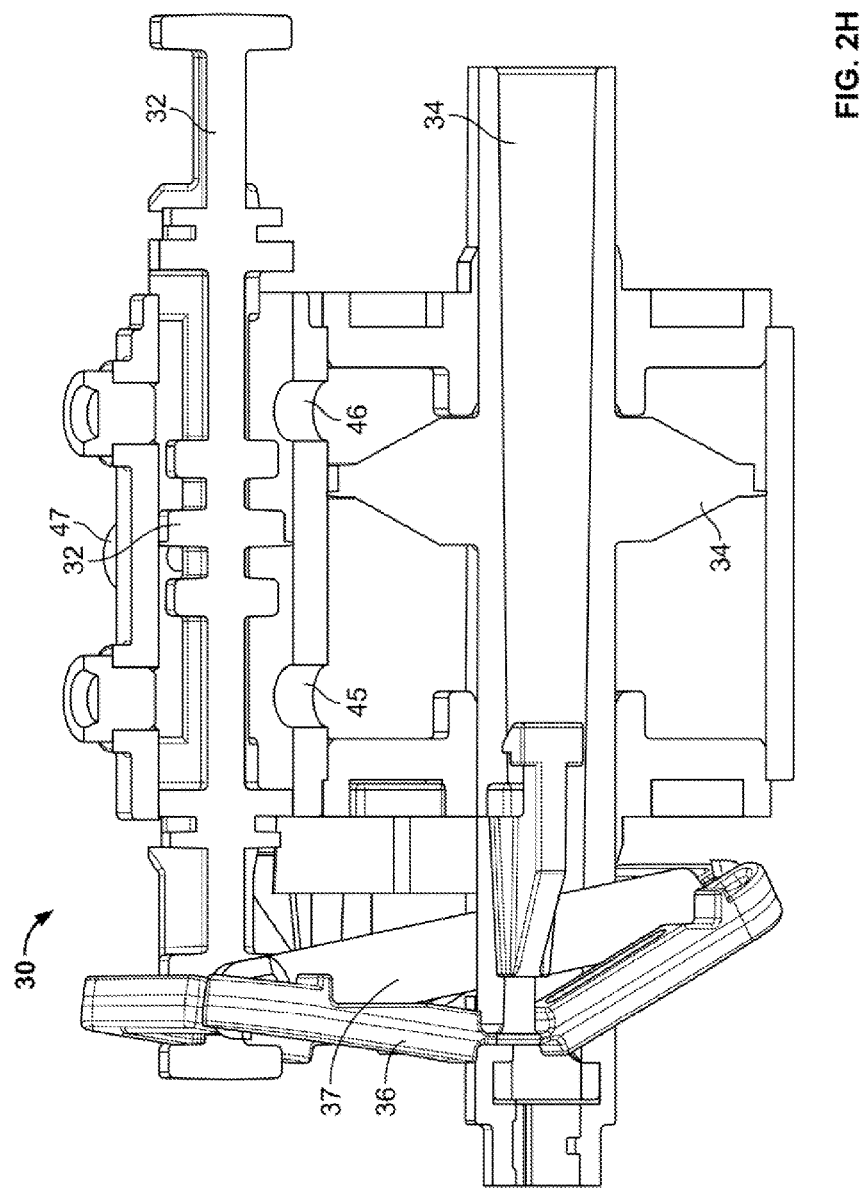
FIGS. 2H-2I illustrate side and prospective cross sectional views of the vacuum powered mechanism of FIG. 2A in a second position.
Figure 2I:
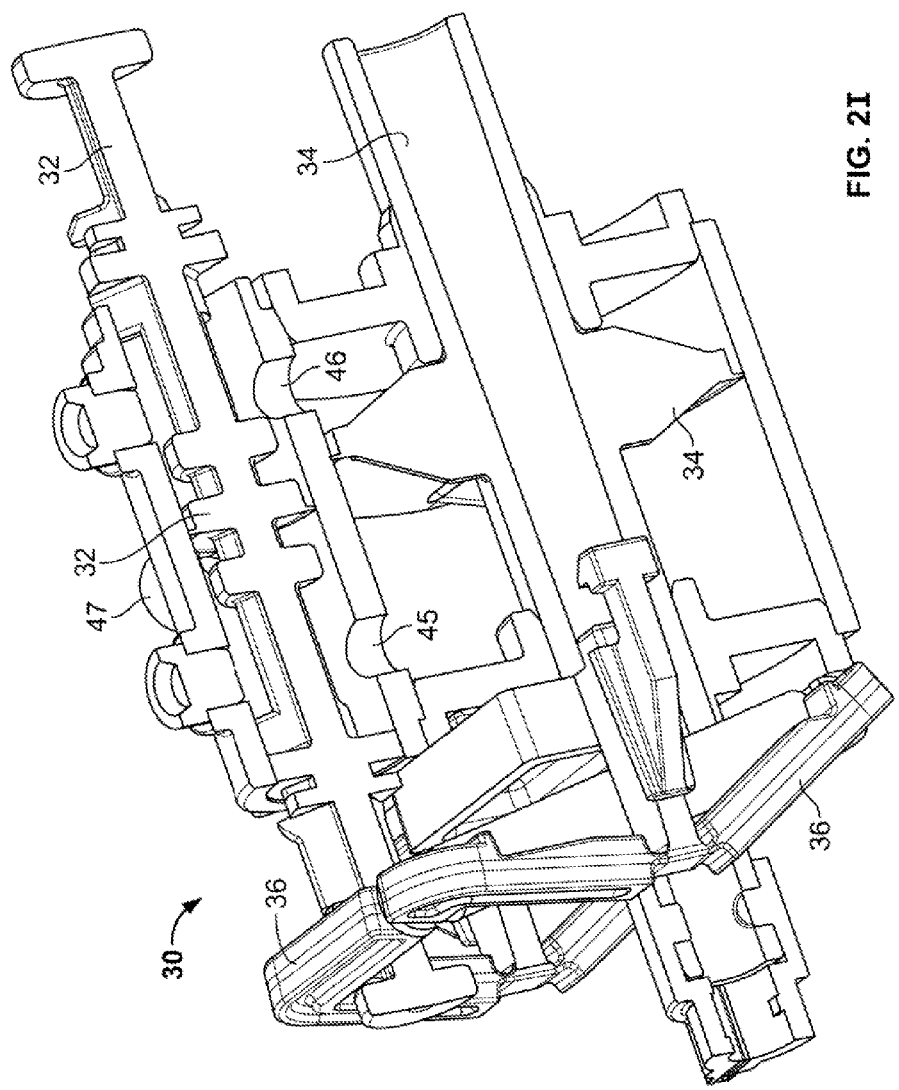

A shuttle chamber vacuum supply port 47 is provided to connect a vacuum source, via a tube or line (not shown), to the mechanism 30 to provide suction to the mechanism 30. FIG. 1H shows a vacuum source coupled to a variation of the cutting device 10. The tube or line may be connected to a second vacuum chamber port 28 (shown in FIGS. 1B-1D) and/or the shuttle chamber vacuum supply port 47. The shuttle chamber vacuum supply port 47 provides entry into the shuttle piston chamber 42, such that the vacuum source can be in fluid communication with the shuttle piston chamber 42 and evacuate the shuttle piston chamber 42 and/or the drive piston chamber 44, to power and motivate the drive piston 34 and/or the shuttle piston 32, as described in further detail herein. Details of a vacuum powered mechanism are also provided below with reference to FIGS. 3A-3B.

The mechanism 30 may be activated and the drive piston 34 reciprocated by suction from the vacuum source as soon as the vacuum source is connected to the cutting device 10 and the vacuum source is activated. Referring back to FIGS. 1A-1E, the cutting device 10 may also include a trigger 26 positioned on the chamber 20 in a location such that the trigger 26 can be conveniently or ergonomically actuated by a user's finger as the user holds the cutting device 10. When the trigger 26 is in the "on" position, the trigger 26 is disengaged from the shuttle piston 32, allowing the shuttle piston 32 to reciprocate due to motivation of the bi-stable switch 36 which is in turn motivated by the movement of the drive piston 34. When the trigger 26 is actuated into an "off" position, the trigger 26 may interact with or engage the shuttle piston 32, which causes the shuttle piston 32 and drive piston 34 to stall or stop such that the cutter 18 is stopped in a position proximal to the opening 16 thereby leaving the opening 16 open. This allows the device 10 to be used for suction or evacuation through opening 16, even when the mechanism 30 and cutter 18 are not activated, as the vacuum source may remain activated and connected to the cutting device 10, supplying suction through a lumen of the evacuation shaft 17. In certain variations, suction may not be supplied through the lumen of the evacuation shaft during cutting.

The vacuum source may be connected to the cutting device 10 at the external vacuum port 29. The external vacuum port 29 is in fluid communication with the tissue collection chamber 22 and the first vacuum chamber port 21, supplying suction to the lumen of the evacuation shaft. The external vacuum port 29 is in fluid communication with the second vacuum chamber port 28, supplying suction through the shuttle chamber vacuum supply port 47 to the shuttle piston chamber 42 and the drive piston chamber 44, to motivate, reciprocate and/or power drive piston 34, which motivates or reciprocates the bi-stable switch 36 and cutter 18, which is connected to the vacuum powered mechanism 30 either directly or indirectly.

In use, the elongate shaft 12 of the cutting device 10 may be inserted into the desired location or area in a patient. The vacuum source is connected to the cutting device 10, supplying suction to the mechanism 30, causing the drive piston 34 to reciprocate. The drive piston 34 causes one side of the bi-stable switch 36 to move either proximally or distally which increases the tension on the extension spring 37. The increased tension on the extension spring 37 causes the adjacent side of the bi-stable switch 36 and the shuttle piston to move proximally or distally to decrease the length of the extension spring 37. When the seal on the shuttle piston or shuttle piston 32 moves past the suction port 47, the vacuum or suction in the shuttle chamber 42 reverses to the opposite side of the drive piston 34 while atmospheric air is allowed to flow into the side of the shuttle chamber 42 that is not evacuated, thereby motivating the drive piston 34 to move toward the evacuated side. (As shown for example in FIG. 2B). The evacuation shaft 17 is connected to the drive piston 34. The evacuation shaft 17 may be connected directly to the drive piston 34 or the evacuation shaft 17 may be connected to sleeves, tubes or other shafts that are connected to the drive piston 34. For example, the piston clamp 35 may connect the evacuation shaft 17 to the drive piston 34.

As stated supra, the cutter 18 is formed at the distal tip of the evacuation shaft 17. Once the vacuum source is connected to the cutting device 10 and the trigger 26 is positioned in the "on" position such that it is disengaged from the shuttle piston 32, suction applied to the mechanism 30 causes the drive piston 34 (and consequently the shuttle piston 32 as described above) to reciprocate, which causes the evacuation shaft 17 and the cutter 18 to reciprocate, driving the cutter 18 back and forth, e.g., in a linear or axial motion along the longitudinal axis of the elongate shaft, past the opening 16 in the elongate shaft 12. A close up of a variation of a cutting window is shown in FIG. 1G. At the same time, suction may be supplied from the vacuum source through a lumen of the evacuation shaft 17, to draw tissue into the opening 16, where the tissue is then cut by the reciprocating cutter 18. Optionally, the suction in the evacuation lumen, may also evacuate the cut tissue and deliver it to the tissue collection chamber 22.

While the reciprocating motion of the drive piston 34 of the mechanism 30 is translated to the cutter 18 via the evacuation shaft 17 in the variation described above, other components for translating such reciprocating motion are also contemplated. For example a cutter may extend from a wire or blade or any other extension or member which is connected to the mechanism 30, e.g., via the drive piston 34 or piston claim 35. In certain variations, the cutter 18 may be directly or indirectly connected to the mechanism 30 or the drive piston 34 or the shuttle piston 32 or the bi-stable switch 36.

In certain variations, a loop or extension may be provided in the evacuation shaft 17 or in a tube or pipe connecting the evacuation shaft 17 to the first vacuum chamber port 21, providing extra length that may move or change shape such that at least a portion of the evacuation shaft 17 or tube or pipe that is connected to the first vacuum chamber port 21 does not move or reciprocate or become dislodged when the evacuation shaft 17 is being reciprocated or motivated by the mechanism 30.

In certain variations, a method of cutting and removing tissue from a subject may include advancing a cutting device at, next to, in or near a target tissue in the subject. The cutting device may include an elongate shaft and a cutter positioned within or on the elongate shaft. The elongate shaft may be advanced into the subject to access the target tissue and to position the cutter at, next to, in or near the target tissue to cut and/or remove the tissue. The cutting device includes a mechanism or motor which is powered or driven by suction created by a vacuum source. The suction from the vacuum source powers the mechanism causing it to produce a reciprocating or rotating motion which causes the cutter to reciprocate or rotate to cut tissue. The tissue may optionally be evacuated using suction created by the vacuum source. The cut tissue may optionally be gathered or collected with the cutting device. In certain variations, suction or vacuum may be turned off or not supplied to the opening and the tissue may be otherwise removed. In certain variations, the suction from the vacuum source may draw tissue into an opening on the elongate shaft. The cutter may be reciprocated or rotated past the opening to cut the tissue drawn into the opening on the elongate shaft. In certain variations suction from the vacuum source may draw an irrigant to the distal end of an evacuation lumen in the elongate shaft or to the opening of the elongate shaft, where it lubricates tissue and/or the evacuation lumen, to facilitate evacuation of the cut tissue. In certain variations, the cutting device may include a chamber in which the mechanism is positioned. The elongate shaft may be attached to the chamber such that it remains in a fixed position relative to the chamber while the mechanism is producing a reciprocating motion and reciprocating a cutter shaft or evacuation shaft positioned within the elongate shaft.

In certain variations, a method of cutting, resecting or excising tissue in a patient may include attaching the cutting device to a vacuum source (internal or external) and optionally to a source of irrigant. The vacuum source supplies suction that may power or motivate the mechanism or motor of the cutting device, draw tissue into the path of a cutter or cutting blade, draw irrigant from an irrigant source to the site of cutting or excision or near the cutter, and/or evacuate cut tissue from the patient.

In certain variations, a method for performing a polypectomy in a subject may include advancing a cutting device at, to, next to, in or near a target polyp. Polyps may be located in various regions of a patient. For example, nasal or sinus polyps may be cut and/or removed by advancing the cutting device into the nasal cavity and positioning a cutter at, next to, in or near the polyp. The cutting device may include an elongate shaft and a cutter positioned within or on the elongate shaft. The elongate shaft of the cutting device may be advanced into the nasal or sinus cavity to access the polyp and position the cutter near the polyp. The cutting device includes a mechanism or motor which is powered by suction created by a vacuum source. The suction from the vacuum source powers the mechanism causing it to produce a reciprocating or rotating motion which causes the cutter to reciprocate or rotate to cut tissue. The tissue may optionally be evacuated using suction created by the vacuum source. The cut tissue may optionally be gathered or collected with the cutting device. In certain variations, suction or vacuum may be turned off or not supplied to the opening and the tissue may be otherwise removed. In certain variations, the suction from the vacuum source may draw tissue into an opening on the elongate shaft. The cutter may be reciprocated past the opening to cut the polyp tissue drawn into the opening on the elongate shaft. In certain variations, the mechanism may be powered solely by suction from a vacuum source, without requiring the use of compressed or pressurized air or electric power to supply power.

In certain variations, a method for performing a discectomy in a subject may include advancing a cutting device at, to, next to, in or near a disc in a spine. For example, a disc annulus or nucleus may be cut by advancing the cutting device into or next to the disc and positioning a cutter at, next to, in or near the disc. The cutting device may include an elongate shaft and a cutter positioned within or on the elongate shaft. The elongate shaft of the cutting device may be advanced into or next to the disc to position the cutter. The cutting device includes a mechanism or motor which is powered by suction created by a vacuum source. The suction from the vacuum source powers the mechanism causing it to produce a reciprocating or rotating motion which causes the cutter to reciprocate or rotate to cut tissue. The tissue may optionally be evacuated using suction created by the vacuum source. The cut tissue may optionally be gathered or collected with the cutting device. In certain variations, suction or vacuum may be turned off or not supplied to the opening and the tissue may be otherwise removed. In certain variations, the suction from the vacuum source may draw tissue into an opening on the elongate shaft. The cutter may be reciprocated past the opening to cut the disc tissue drawn into the opening on the elongate shaft. In certain variations, the mechanism may be powered solely by suction from a vacuum source, without requiring the use of compressed or pressurized air or electric power to supply power.

In certain variations, a user may cut tissue by positioning a cutting window on an elongate shaft against the tissue to be resected and actuate a switch or trigger to allow the mechanism to reciprocate. This causes a cutting blade to move back-and-forth past the cutting window. As tissue is drawn into the cutting window by suction, the blade shaves the portion of tissue that is in the path of the cutting blade. The tissue is then evacuated through the lumen of the shaft that is connected to the blade and is deposited in a tissue collection chamber.

The cutting devices described herein may be utilizing for a variety of procedures as described supra. The cutting device may be advanced or inserted into or through existing orifices, cavities or passages, e.g., a nasal cavity, airway, respiratory passage, reproductive pathways, intestinal pathways or other pathways. The cutting devices may be advanced or inserted into a patient percutaneously, intraluminally or in any minimally invasive manner to perform a procedure in or on a subject. Optionally, a cutting device may be utilized through a surgical incision or site.

The various cutting devices described herein, e.g., a handheld and/or portable cutting device, allow for cutting and/or removal of tissue, e.g., a nasal polyp, by providing a low cost, disposable device that allows the tissue cutting procedure to take place in a manner that is safe, quick, and inexpensive.

The cutting device does not require significant setup time, or the inconvenience and expense associated with capital equipment. In-office tissue removal using a cutting device may be performed using local anesthetic as compared to general anesthetic which is used in ambulatory surgery centers. For example, a cutting device may be utilized to perform nasal and sinus polyp removal in a doctor's office setting. While the cutting devices described herein may be used to perform a polypectomy, they can also be used for tissue resection procedures in other locations of the body, e.g., including for ear, nose, and throat surgery, gynecological surgery, spinal surgery, general surgery and ophthalmic surgery.

A cutting device that uses a vacuum source, e.g., an external vacuum source, to power an actuating or reciprocating mechanism or motor that is connected to a cutter, thereby translating the reciprocating motion to the cutter to cause the cutter to reciprocate provides a number of advantages and efficiencies. The cutting device does not require an investment in capital equipment, such as electric powered consoles, thus providing a user with a substantial cost savings. Capital equipment requires valuable storage space when not in use as well as service and maintenance in the facilities where it is used. The cutting device also allows a manufacturer to make continuous improvements without being constrained by installed capital equipment.

The cutting devices described herein may be manufactured using low cost components and assembly techniques, making the cost of the device much lower than a cutting device which utilizes an electric motor. The elongate shaft may be constructed from a variety of materials. For example, a combination of metal and plastic components that are not susceptible to heat buildup resulting from friction between moving components may be utilized.

Using a vacuum source as the power source to provide both tissue evacuation and mechanical motion to cut tissue eliminates or reduces the number of additional or separate connections, wires or tubes that would otherwise be required to provide electrical or other pneumatic power, such as pressurized or compressed air, and evacuation. A standalone console to transfer the electrical or other pneumatic power may not be required to operate the cutting device.

In certain variations, a single tube connects the vacuum source to the cutting device to serve the functions of tissue cutting, evacuation, and to power the mechanism which actuates the reciprocating cutter. A single tube simplifies connections required for device operation and reduces the number of tubes attached to the device thereby reducing the "clutter" and unwieldiness caused by multiple tubes and wire connections extending from a device.

In certain variations, a splitting connection within the handle may be provided which connects the vacuum to both a tissue evacuation tube and the vacuum powered mechanism. The splitting connection may come in multiple forms such as multiple connections to the tissue collection chamber where a single connection to a source of vacuum creates a vacuum within a Filter Chamber. Another form of a splitting connection may be a "Y" or "T" shaped junction that joins two fluid paths into a single path. As a result of sharing the vacuum source between the mechanism and the evacuation tube and cutting window or opening, the vacuum perform several functions within the device: powers the mechanism which causes the cutter to reciprocate, draws tissue into an opening or cutting window such that it may be excised, evacuates the excised tissue through the tissue evacuation shaft to a filter or tissue collection chamber.

Where an external vacuum source is connected to the device to provide suction to facilitate tissue cutting and evacuation, an additional power source such as electricity, compressed air, or mechanical input by the operator may not be required.

Using vacuum power to actuate the cutter reduces operator fatigue compared to a system requiring the operator to manually actuate the reciprocating mechanism. The rate at which the cutter actuates, relative to manual actuation, may be significantly increased, thereby reducing the time required to complete a tissue resection or excision procedure. Also, the control for the rate of actuation of the mechanism or motor may be moved from a "primary" position, such as a trigger or button, to a "secondary" position, e.g., on the device handle. As a result, the "primary control" may be utilized to control other parameters, e.g., the rate at which the cutter actuates, the radius of curvature of the elongate shaft, or to control an electrocautery system that may be included in or on the device. A knob, trigger, roller clamp, or other control interfaces may be used to control the rate at which the vacuum driven mechanism or motor actuates or reciprocates. These options allow the device to be designed in a variety of configurations to suit various surgical specialties or personal preferences.

The cutting devices described herein may have a relatively low mass, providing ease of use and comfort during short or long procedures. The cutting devices may be easily sterilized using commonly used sterilization techniques such as electron beam radiation, gamma radiation, or Ethylene Oxide gas.

In certain variations, a pneumatic logic sequence that maintains high vacuum throughout the mechanism, motor or engine cycle by never venting the vacuum source to the atmosphere may be provided. As a result, the vacuum suction or pressure that facilitates cutting and evacuation does not decrease while the mechanism or motor reciprocates.

In certain variations, the cutting device may include cautery, e.g., an electrocautery system or wires heated via monopolar or bipolar radiofrequency, or by resistive heating. The cautery may be located at or near the distal extremity of the device to cauterize tissue to control bleeding at the site where tissue has been cut or excised. Having a cautery obviates the need to remove the device from an operative site and replace it with a separate electrocautery device, thereby improving speed and ease-of-use for the operator while reducing blood loss for the patient. The electrocautery system may be powered by wires that run the length of the elongate shaft through an internal lumen within the elongate shaft. The wires may be connected to a power console or optionally the power source may be located in the handle or chamber of the cutting device.

In certain variations, a resistive heating electrocautery system may be provided on the distal tip of an elongate shaft. The power source for the electrocautery system may be located in the handle of the cutting device and may be connected to the distal tip of the shaft by wires that run the length of the shaft. The power source may include one or more batteries that provide electrical energy to the distal end of the device. The electrical energy may be converted to heat energy when passed through a heating element such as a tungsten wire.

As described supra, in certain variations, a cutting device may include a malleable elongate shaft or at least a partially malleable elongate shaft that may be hand adjustable. A flexible or malleable shaft provides access to multiple anatomical locations using a single device, thereby improving cost efficiency and convenience for the operator. One or more annealed wires may be positioned in an elongate shaft or flexible shaft to allow the shaft to be manually shaped by the user intra-operatively. Alternatively, malleable tubing may be used to construct the elongate shaft to allow manual shaping of the shaft. Additionally, when the distal end of the elongate shaft is curved toward the cutting window, visibility of the cutting window location is improved.

In certain variations, the elongate shaft may be flexible and a semi-rigid or rigid outer cannula or sheath may be provided on the shaft to change the radius of curvature on the shaft in a range from substantially straight to curved, in an arc of about 180 degrees. The cannula allows the operator to optimize the curvature of the shaft based on the patient anatomy. The operator may also increase or decrease the force between the elongate shaft or cutter and the target tissue being cut by extending or retracting the cannula to increase or decrease the natural radius of curvature of the elongate shaft.

In certain variations, a semi-rigid or rigid outer sheath or cannula positioned over a flexible curved elongate shaft may be used to change the radius of curvature of the curved shaft. The radius of curvature may increase when the straight and rigid sheath is extended over the curved portion of the shaft, whereas the radius of curvature returns to its precurved or predetermined shape when retracted from the curved portion of the shaft.

The radius of curvature of a flexible curved elongate shaft may be altered in-vivo by utilizing or advancing or retracting a cannula over the elongate shaft. This allows the operator to change the radius of curvature of the elongate shaft in situ to gain access to a variety of anatomical locations without removing the device or elongate shaft from the operative site to change the radius of curvature.

In certain variations, the distal tip of the elongate shaft may be rounded and less likely to perforate sensitive structures or other tissue during advancement to a target tissue or while cutting is being performed. This reduces susceptibility to inadvertent contact with tissues that may result in unintended injury to the patient.

Reciprocating a cutter in a back-and-forth motion may shave and cut tissue by scissoring it rather than grabbing and ripping tissue as may be the case with certain rotary cutters or rotary mechanisms or motors. Back-and-forth cutting action may shave tissue with less movement of the tissue, which reduces the tension on the tissue and consequent trauma to the tissue thereby reducing the likelihood of bleeding. The excised tissue may then be evacuated through an evacuation shaft and into a tissue collection chamber.

An elongate shaft that includes a cutter shaft or an evacuation shaft with a cutter at its distal end, which may be reciprocated in a back and forth motion along the longitudinal axis of the elongate shaft, may be positioned in line or at an angle relative to the vacuum driven mechanism or motor and the handle or chamber in which the mechanism or motor is positioned. Positioning at an angle allows the device handle to be positioned away from the control surfaces, light cord, and any power cables for an endoscope and/or camera that may also be used during the tissue cutting procedure. The operator's ease-of-use is improved because the endoscope and the cutting device are not interfering with one another.

A cutting device having a handle or hand piece that may be positioned in line with an elongate shaft or at an angle to the longitudinal axis of the elongate shaft may provide improved ergonomic features for the operator. For example, when the operator is using a second device, (e.g., an endoscope as described supra) through the same orifice or port that the elongate shaft of the cutting device has entered, the two devices may interfere with one another. However, by positioning the handle or hand piece at an angle to the longitudinal axis of the shaft, the top and sides of the cutting device around the shaft and the connection between the handle and the shaft are at a very low profile. Thus, the likelihood of interference is reduced. In certain variations, the elongate shaft may be actuatable, such that the elongate shaft may be moved between a position in line with a handle or at an angle to a handle.

The back and forth reciprocating motion of a cutter shaft or an evacuation shaft with a cutter blade at its distal end may be translated along a nonlinear path. Therefore, it is possible to position the vacuum driven mechanism or motor at an angle relative to elongate shaft of the device. Furthermore, the back and forth reciprocating motion of the cutter shaft or an evacuation shaft allows the elongate shaft of the cutting device to be bent at the distal portion of the shaft (e.g., where the shaft is malleable) to allow it to be shaped to access a variety of locations in the anatomy.

In certain variations, separate conduits may be provided between the mechanism and evacuation lumen such that vacuum for evacuating tissue is not interrupted by the mechanism function.

An anvil component may be located at the distal end of the elongate shaft. An extension (e.g., a "tail") of the anvil may be provided proximal to the cutting window. The extension may improve flexibility of the shaft allowing the shaft to be malleable closer to the distal end of the shaft. The anvil and/or extension may maintain or provide a guide for the evacuation shaft or the cutter shaft as it translates or reciprocates axially. In the absence of an extension, a longer anvil component that may be rigid over its entire length or a portion of its length may be provided.

In certain variations, a cutting opening or window may be positioned on the side of the elongate shaft. The side positioning allows the operator to maintain visual contact or visualization on the position of the opening or window and tissue that comes into contact with the opening or window. This visual contact reduces the likelihood of unintentionally causing injury to tissue.

A cutting window may be shaped to prevent the cutter from exiting the lumen of the elongate shaft or the anvil component, through the cutting window. The cutting window in combination with the cutter may provide a tissue scissoring cutting action, as compared to a guillotine cutting action on a straight sided cutting window.

In certain variations, the distal portion of an elongate shaft may be plastic, an indwelling anvil component may be metal, a cutter may be metal and the evacuation tube may be plastic. This arrangement may reduce the likelihood of heat build up from friction between moving and/or stationary components of the cutting device. This arrangement may create a scissoring cutting action, and/or allow the distal end of the elongate shaft to be flexible and malleable. Additionally, the use of plastic components reduces or eliminates the possibility that electrical energy may be unintentionally transmitted through the shaft thereby injuring the patient.

Optionally, the elongate shaft may be rotatable about the axis of the shaft relative to the device handle or chamber, which allows the operator to rotate the shaft without rotating the device handle.

In certain variations, one or more lumens 51, e.g., nonconcentric lumens may be positioned in the elongate shaft (As shown in FIG. 1F). Nonconcentric lumens may provide advantages compared to single lumen shafts and shafts having concentric lumens. For example, one or more of the lumens may be used for the following purposes: to provide a fluid conduit for irrigant; to hold or contain one or more malleable wire(s) to maintain the shaft curvature when shaped by the operator; to contain the evacuation shaft or cutter shaft and evacuation lumen; and/or to transmit fluid to treat bleeding.

In certain variations, an evacuation lumen may be non contiguous around its circumference down a portion or the entire length of the evacuation shaft to improve flexibility while reducing the likelihood of kinking the evacuation lumen.

A small gap or a sealing O-ring between the evacuation shaft and the inside of the main lumen of the elongate shaft, may reduce the likelihood of leakage of suction through the proximal end of the elongate shaft, which would reduce the suction present at the window.

Optionally, a ring of material may be provided between the outside diameter of a noncontiguous evacuation lumen and the inside diameter of a multi-lumen evacuation shaft or tubing that seals the air gap between the two structures and thereby reduces leakage of air flow in the distal direction from the device handle to the opening in the evacuation shaft or lumen, located proximal to the cutting window or opening.

Optionally, various fluids may be applied or delivered to the distal end of the elongate shaft where the cutter and window are positioned. A fluid may be emitted, via a lumen in the elongate shaft, from the distal end of an elongate shaft at a temperature that is low enough such that the fluid can be used as a bleeding therapy. A collagen foam may be emitted from the distal end of the elongate shaft as a bleeding therapy. These are inexpensive, quick, and easy ways to apply a bleeding therapy or anticoagulant to a bleeding site where tissue is being cut. Anti-coagulant substances emitted from the distal end of the elongate shaft as a bleeding therapy may be applied directly and conveniently to the tissue, e.g., without exchanging or removing the cutting device to replace it with a separate device intended for applying anticoagulation therapy.

In certain variations, separate fluid conduit paths to the vacuum source may be provided to allow the vacuum powered mechanism and cutter to be operated independently from the tissue evacuation. The independent fluid paths and operation capability of the vacuum powered mechanism and evacuation may allow the opening in the distal end of the elongate shaft of the cutting device to operate as a suction port to evacuate tissue and blood even when the vacuum powered mechanism is not in operation or is stalled or halted, e.g., when the trigger is actuated to engage and hold the shuttle piston to prevent its reciprocation.

Optionally, a single fluid conduit path between a cutting window and the vacuum source that includes an evacuation shaft and vacuum mechanism may be utilized to reduce the air flow requirements of the device by using air flow created by the vacuum to power both the vacuum mechanism and the evacuation of tissue.

Set forth below are additional features or functions that may be utilized or included with various cutting devices described herein:

A clear tissue collection chamber may be utilized to allow the operator to intraoperatively visualize resected tissue in real time. Additionally, the operator and patient are able to see whether the device has been previously used by inspecting the tissue collection chamber.

A dual chamber tissue collection system may be provided to separate tissue resected from different locations in the event it is desired to biopsy the tissue from two different locations in the body A bi-stable switch fabricated from plastic, metal or other material and an elastic spring may be utilized in a mechanism to ensure reliable transition of a Shuttle piston past a vacuum supply port to prevent unstable flutter of the Shuttle piston and consequent mechanism or motor stall. Optionally, a bi-stable switch fabricated using sheet metal with two legs that are connected at one end but separated at the opposite end in their natural state may be provided. The separate sheet metal legs are then riveted or otherwise connected to create a bowed sheet metal component that is stressed and bi-stable. Optionally, the separated end may be folded and joined to result in a three dimensional curve that is stable in two positions. These variations may not require a separate elastic spring to be bi-stable.

Optionally, back-and-forth reciprocating motion from a vacuum powered mechanism may be mechanically converted to rotational motion or rotary oscillation to provide rotational or rotary oscillation mechanical output by the mechanism.

A tissue evacuation shaft may be routed through the center of the drive Piston to provide an efficient method of transferring the mechanical output of the mechanism to the cutter at the window.

To prevent vacuum leakage in the motor, a thin plastic seal may be molded integral to a component and plastically deformed by squeezing the thin plastic seal in a die to increase its flexibility and conformability. This may reduce the cost of components and assembly labor, and it may improve the overall reliability of the mechanism. Optionally, flash formed at a parting line of a mold may be used as a seal because it is very thin and flexible and conforms to the geometry of mating components while maintaining minimal friction between components. An O-ring may optionally be used to create a seal between molded components.

In certain variations, a mechanism may include a Shuttle piston positioned or arranged adjacent to and/or parallel to the drive Piston such that overall mechanism and or device size is reduced, the transfer of mechanical motion between the pistons is easier and more efficient and the flow of air through the device is more efficient. This arrangement may allow for a smaller, easy to hold and use device. The shuttle and drive piston's may be coupled by a bi-stable switch.

A spring-loaded Trigger may directly or indirectly interact with the Shuttle piston or valve to turn the mechanism "ON" and "OFF." This reliably and consistently controls the mechanism function. The trigger may be designed to always stop the motor with the Cutter shaft proximal to the opening or cutting window thereby leaving the cutting window open such that the device may be used in "suction only" mode through the window. Additionally, a device cleaning tool, such as a declogger, may be threaded through the cutting window and proximally advanced through and/or along the tissue evacuation path to clear or remove obstructions in the tissue evacuation path.

A loop of flexible tubing that connects the evacuation shaft to a stationary connection on the device, such as a vacuum port, provides a low cost way to allow back-and-forth motion of the evacuation shaft and the mechanism without causing shaking, vibration or external motion of other tubing or components in a chamber or handle, and without dislodging the evacuation path connection to the tissue collection chamber. The loop of tubing may change shape to accommodate the back-and-forth motion of the evacuation shaft.

The cutting device may be designed such that irrigant does not flow unless suction is present at the opening or cutting window to draw the irrigant, e.g., to provide a self regulating supply of irrigant. This may be possible by supplying a reservoir of irrigant that is not pressurized relative to atmospheric air, however, when suction is applied to the reservoir, irrigant flows from the reservoir and toward the source of vacuum. An example of this is a syringe filled with irrigant that is connected to tubing; when suction is applied to the tubing, irrigant flows from the syringe and through the tubing toward the source of vacuum. This will ensure the irrigant does not unintentionally flow out of the device and leak into the patient where it may be problematic such as when aspirated by the patient (e.g., when the device is used in the respiratory passages), e.g., where a patient is under general anesthesia and can't communicate. An irrigant reservoir may be located within the handle of the device such that it may be filled by the operator as needed, thereby reducing the number of tubes and connections that are tethered to the cutting device.

A cutting device or microdebrider having a reciprocating or back-and-forth cutting motion may optionally be powered by an integrated supply of compressed air such as a CO2 cartridge or by a battery, e.g., one that supplies electricity to a DC motor that actuates a cutter. This would allow the vacuum supply to be used entirely to draw tissue into the cutting window and to evacuate excised tissue thereby increasing or improving a resection rate. A separate power console is not necessary to provide power to the device.

Exemplary Vacuum Powered Mechanisms Or Motors

A vacuum powered or driven mechanism or motor used in various of the cutting devices described herein may be so called because it uses suction from an internal or external vacuum source to produce movement. The vacuum mechanism or motor does not create suction and is not to be confused with a vacuum pump. The Vacuum is used to power a mechanism to power a medical device which cuts and evacuates tissue. A vacuum-powered mechanism generates the reciprocating or rotating motion of the cutter in the device. The mechanism may be powered by the difference in ambient atmospheric air pressure on one side of a piston and a vacuum (or partial vacuum) on the opposite side of the piston in the chamber or cylinder in which the piston is positioned.

One vacuum mechanism or motor described herein may be referred to as a double action vacuum powered mechanism or double action mechanism because it uses suction to move the piston in both directions. Vacuum or suction is alternately applied to either sides of a piston to cause the piston to alternately move back and forth in the direction of the vacuum (or partial vacuum). Vacuum mechanisms or motors that use a spring to return them to their starting position may be referred to as a spring action or spring return mechanism. A single action mechanism or motor may use a vacuum to drive the piston in a single direction until the vacuum is vented and the piston is returned to its starting position by a spring.

One advantage of using vacuum to move the piston in both directions, as compared to using a spring to return the piston to its starting position, is that the efficiency of the motor is nearly doubled. A spring return mechanism must have a piston size and cylinder volume that is large enough to generate adequate force both to perform the work output required of the motor as well as to compress the return spring. The smaller piston size of a double action mechanism allows the mechanism to be incorporated into a handheld device. The spring on a spring-return motor must be adequately sized to reliably return the piston to its starting position with an adequate safety margin to reliably overcome friction and external forces on the mechanism.

Exemplary variations of vacuum driven mechanisms are described herein. FIGS. 3A-5B show various mechanisms in distal and proximal positions. The distal position refers to a piston in the mechanism being motivated in a direction toward the distal end of the cutting device in which the mechanism would be situated. Regarding the figures described below, from a viewer's perspective, the left side of the figures is the proximal side and the right side of the figures is the distal side. The proximal position refers to a piston in the mechanism being motivated in a direction toward the proximal end of the cutting device in which the mechanism would be situated.

Figure 3A:
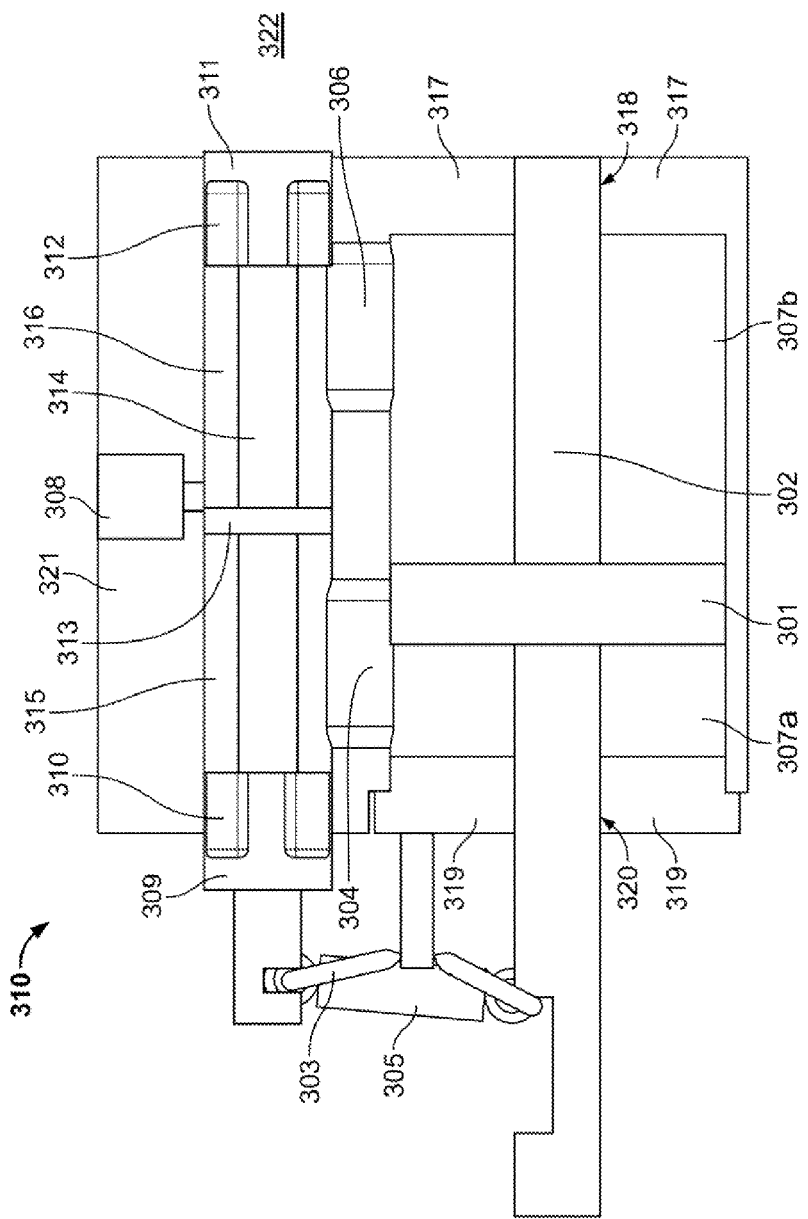
FIG. 3A illustrates a cross sectional view of a variation of a double action vacuum powered mechanism having a bi-stable switch in a proximal position.

FIG. 3A shows a cross sectional view of a variation of a double action vacuum powered mechanism 310 or motor, similar to the mechanism 30, referred to above. The mechanism 310 includes a bi-stable switch. FIG. 3A shows the mechanism 10 in a proximal position, while FIG. 3B shows the double action vacuum powered mechanism in the distal position.

Figure 3B:
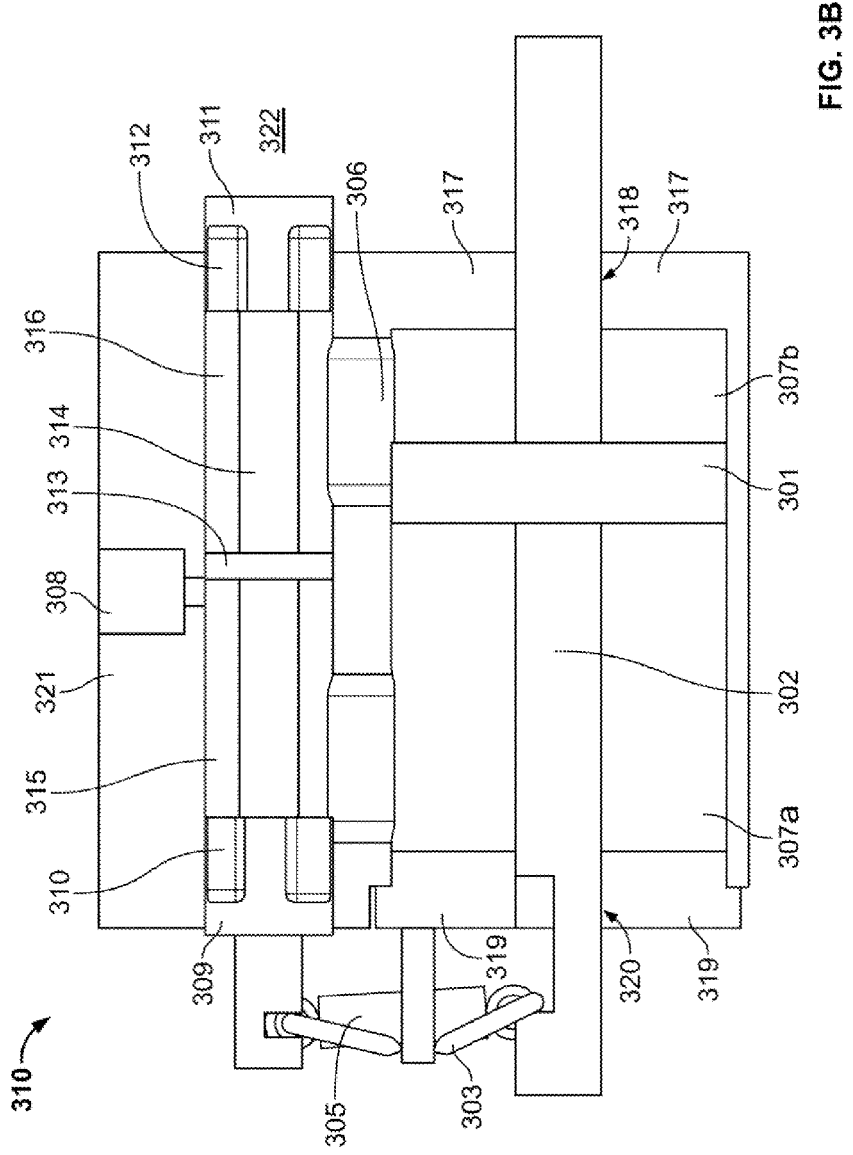
FIG. 3B illustrates a cross sectional view of the double action vacuum powered mechanism having a bi-stable switch of FIG. 3A in a distal position.

Referring to FIGS. 3A-3B, the vacuum powered mechanism 310 includes a drive piston 301 having a piston shaft 302. The drive piston 301 including at least a portion of the piston shaft 302 are positioned within a drive piston chamber 307. The drive piston 301 divides or separates the drive piston chamber into a proximal drive piston chamber 307a and a distal drive piston chamber 307b. The drive piston 301 may reciprocate proximally and distally within the drive piston chamber 307 when vacuum and ambient air are alternately applied to opposite sides of the drive piston 1 in drive piston chambers 307a and/or 307b. The piston shaft 302 may reciprocate along with the drive piston 301, and the reciprocating piston shaft 302 may conduct reciprocating motion output.

A bi-stable switch 303 is connected or coupled to a shuttle piston 314 and a switch spring 305. The switch spring 305 may cause the bi-stable switch 303 to quickly transition from a distal position to a proximal position and vice versa. The bi-stable switch is stable when it is in either a proximal position (FIG. 3A) or a distal position (FIG. 3B), but not when it is in between those two positions and therefore the switch resists residence in an in-between state. As a result, the mechanism does not "flutter" or the mechanism minimizes "flutter" when in transition between states. For example, the shuttle valve 313 may not flutter or not fail to fully transition from a proximal to a distal position or vice versa as the bi-stable switch causes the shuttle piston 314 and a shuttle valve 313 to transition or translate in the proximal or distal direction over and past a shuttle chamber vacuum supply port 308.

The bi-stable switch 303 may be actuated by the drive piston shaft 302 when the drive piston 1, and therefore the piston shaft 302, move in either the proximal or distal directions. Actuation of the bi-stable switch 303 results in movement of the shuttle piston 314 in either the proximal or distal directions. Movement of the drive piston in the proximal direction results in movement of the shuttle piston in the proximal direction via the bi-stable switch, while movement of the drive piston in the distal direction results in movement of the shuttle piston in the distal direction via the bi-stable switch.

The shuttle piston 314 is positioned within a shuttle piston chamber. The shuttle piston 314 includes a shuttle valve 313 or flange which may extend radially therefrom, which separates or divides the shuttle piston chamber into a proximal shuttle piston chamber 315 and a distal shuttle piston chamber 316. Proximal shuttle piston chamber 315 may be in fluid communication with proximal drive piston chamber 307a via proximal vacuum slot 304. Distal shuttle piston chamber 316 may be in fluid communication with distal drive piston chamber 307b via distal vacuum slot 306.

The shuttle piston (314) may also include a proximal ambient air seal (309), a proximal cruciform (310), a distal ambient air seal (311), a distal cruciform (312), and a central shaft connecting the above components.

A shuttle piston chamber vacuum supply port (308) may be connected to an external or internal vacuum source or supply to evacuate the proximal shuttle piston chamber 315 and/or the distal shuttle piston chamber 316. The vacuum port 308 may allow for evacuation by vacuum of the proximal drive piston chamber 307a via the proximal vacuum slot 304 and the proximal shuttle piston chamber 315. The vacuum port 308 may allow for evacuation by vacuum of the distal drive piston chamber 307b via the distal vacuum slot 306 and the distal shuttle piston chamber 316.

For example, Proximal drive piston Chamber (307a) may be evacuated by vacuum when in fluid communication with the external vacuum source via the Vacuum Port (308), Proximal Shuttle piston Chamber (315), and proximal vacuum slot 304. Distal drive piston Chamber (307b) may be evacuated by vacuum when in communication with the external vacuum source via the Vacuum Port (308), Distal Shuttle piston Chamber (316), and distal vacuum slot 306. Presence of vacuum in Proximal drive piston Chamber 307a results in differential pressure between the proximal and distal sides of the Piston (301) that results in working force to move the Piston (301) proximally when ambient air is in the distal drive piston Chamber (307b). Alternately, ambient air (322) in proximal drive piston Chamber 307a applies working force to move the Piston (301) distally when the Distal drive piston Chamber (307b) is evacuated.

The shuttle piston 314 may be translated or positioned in a shuttle piston chamber such that Shuttle piston valve 313 can seal against the shuttle block (321) to the distal side of the vacuum port (308) to allow the proximal shuttle piston chamber (315) and/or proximal drive piston chamber (307a) to be evacuated by communicating with an external vacuum supply. Alternatively, the shuttle piston 314 may be translated or positioned in a shuttle piston chamber such that the shuttle piston valve 313 may seal against the shuttle block (321) to the proximal side of the vacuum port (308) to allow the distal shuttle piston chamber (316) and/or distal drive piston chamber (307b) to be evacuated by communicating with the external vacuum supply.

The proximal shuttle piston chamber (315) may allow for fluid communication between the Vacuum Port (308) and the Proximal drive piston Chamber (307a) through the Proximal Vacuum Slot (304). The proximal shuttle piston chamber (3315) may also allow for fluid communication between the Proximal drive piston Chamber 307a and ambient air when the Proximal Shuttle Seal (309) is in the proximal position, i.e., an open or unsealed position.

The Distal Shuttle piston Chamber (316) may allow for fluid communication between the Vacuum Port (308) and the Distal drive piston Chamber (307b) through the Distal Vacuum Slot (306). The Distal Shuttle piston Chamber (316) may allow for fluid communication between the Distal drive piston Chamber 307b and ambient air when the Distal Shuttle Seal 311 is in the distal position, i.e., an open or unsealed position.

The proximal ambient air seal (309) of the shuttle piston 314 may seal against shuttle block (321) to prevent ambient air leakage into proximal shuttle piston chamber 315 when the proximal shuttle piston chamber (315) is evacuated. Also, the proximal cruciform (310) can maintain shuttle piston (314) position concentricity relative to proximal shuttle piston chamber (315), e.g., when the shuttle piston (314) moves to a proximal position and vents ambient air to the proximal shuttle piston chamber (315).

The distal ambient air seal (311) of the shuttle piston 314 may seal against shuttle block (321) to prevent ambient air leakage into distal shuttle piston chamber 316 when the distal shuttle piston chamber (316) is evacuated. Also, the distal cruciform (312) can maintain shuttle piston (314) position concentricity relative to distal shuttle piston chamber (316), e.g., when the shuttle piston (314) moves to a distal position and vents ambient air to the distal shuttle piston chamber (316).

The vacuum powered mechanism 310 may also include a Distal drive piston chamber Endcap (317), which may prevent or minimize fluid communication between ambient air and the Distal drive piston Chamber (307b) in addition to providing a sealing and bearing surface with the drive Piston Shaft (302). The vacuum powered mechanism 310 may also include a Distal drive piston chamber Endcap Seal (318), which may prevent or minimize ambient air leakage between the Distal drive piston chamber Endcap (317) and the drive piston Shaft (302), e.g., when the Distal drive piston Chamber (307b) is evacuated.

The vacuum powered mechanism 310 may also include a Proximal drive piston Chamber Endcap (319), which may prevent or minimize fluid communication between ambient air and the Proximal drive piston Chamber (37a) in addition to providing a sealing and bearing surface with the drive Piston Shaft (302). The vacuum powered mechanism or motor 310 may also include a Proximal drive piston Chamber Endcap Seal (320), which may prevent or minimize ambient air leakage between the Proximal drive piston Chamber Endcap (319) and the drive Piston Shaft (302), e.g., when the Proximal drive piston Chamber (307a) is evacuated.

The drive piston shaft 302 may seal against the endplates or endcaps 317, 319 or shuttle block 321 to prevent or minimize loss of vacuum to ambient air 322. Also, various seals known to person of skill in the art may be utilized to seal the piston shaft against the endplates or endcaps 317, 319 or shuttle block 321.

A shuttle block 321 or other frame, structure, or casing may provide an outer structure for the vacuum powered mechanism 310. Ambient air 322 refers to air at atmospheric pressure which is located outside of the vacuum mechanism. Ambient air 322 may also be allowed to flow inside various chambers of the vacuum powered mechanism during use of the mechanism as described herein.

In use or in operation, the vacuum powered mechanism 310 operates by a pneumatic mechanism, method or logic that utilizes an external or internal vacuum source to provide the force to cause reciprocating motion of the drive piston 301 in both proximal and distal directions. A bi-stable switch may be utilized to transition the mechanism as it reverses or changes direction.

For example, the vacuum port 308 may be opened to the distal drive piston chamber 307b to evacuate the distal drive piston chamber 307b and ambient air is closed to the distal drive piston chamber 307b, while ambient air is opened to the proximal drive piston chamber 307a and the vacuum port is closed to the proximal drive piston chamber 307b. The drive Piston advances toward a distal position due to the vacuum inside the distal drive piston chamber 307b, on the distal side of the drive piston 301 and the ambient air pressure in the proximal cylinder chamber, on the proximal side of the drive piston 301.

As a result of the differential pressure created on opposite sides of the drive piston 301, the drive piston Rod or shaft 302 moves through its dwell until it contacts the bi-stable switch 303, causing the bi-stable switch 303 to rapidly change states from a proximal position to distal position, moving in the distal direction. The bi-stable switch is attached to the shuttle piston 314 and rapidly causes the shuttle 314 to move from a proximal position to distal position in the shuttle chamber. As a result, the vacuum seal 313 on the shuttle piston 314 moves from the proximal side of vacuum port 308 to the distal side of the vacuum port 308, opening the vacuum port 308 to the proximal drive piston chamber 307a to evacuate the proximal drive piston chamber 307a, and closing the vacuum port 308 to the distal drive piston chamber 307b. Also, the distal seal 311 on the shuttle piston 314 opens the ambient air 322 to vent the distal drive piston chamber 307b to ambient pressure, and the proximal seal 309 on the shuttle piston 314 closes the ambient air vent to the proximal drive piston chamber 307a.

The drive piston 301 then reverses direction and moves in the proximal direction, due to the vacuum inside the proximal drive piston chamber 307a, on the proximal side of the drive piston and the ambient air pressure in the distal drive piston chamber, on the distal side of the drive piston 301.

As a result of the differential pressure created on opposite sides of the drive piston 301, drive piston Rod or shaft 302 moves through its dwell until it contacts the bi-stable Switch, causing the bi-stable switch to rapidly change states from a distal position to a proximal position. The bi-stable switch is attached to the Shuttle 314 and rapidly causes the Shuttle 314 to move from its distal position to a proximal position in the shuttle chamber. As a result, the vacuum seal 313 on the shuttle piston 314 moves from the distal side of the Vacuum Port 308 to the proximal side of the vacuum port 308, opening the vacuum port 308 to the distal drive piston chamber 307b to evacuate the distal drive piston chamber 307b, and closing the vacuum port 308 to the proximal drive piston chamber 307a. Also, the Proximal Seal 309 on the Shuttle piston 314 opens the ambient air 322 to vent the proximal drive piston chamber 307a to ambient pressure, and the Distal Seal 311 on the Shuttle piston 314 closes the ambient air vent to the distal drive piston chamber 307b.

Consequently, the mechanism has completed one cycle and is free to continue reciprocating as described above by alternating suction or air pressure on opposite sides of the piston, as long as adequate vacuum is available to the mechanism. Indeed, the above Steps may repeat as necessary such that the vacuum powered mechanism creates a reciprocating motion until the vacuum source is disconnected, turned off, or if the vacuum is inadequate to overcome the force required to move the drive piston 301 or if the mechanism 310 is stalled or stopped.

The reciprocating motion of the mechanism may be utilized to actuate a cutting device or to operate or actuate another device, e.g., another medical device. In certain variations, cutting device may be positioned by maneuvering a flexible or malleable shaft of the device e.g., manually or automatically. The shaft may be maneuvered or positioned around sensitive tissues or structures in the human body by changing the shape of the shaft. For example, extending or retracting an outer sheath or cannula on the shaft or advancing or retracting the shaft relative to the outer sheath, thereby allowing improved maneuverability of the shaft around structures or within confined spaces may be performed, e.g., allowing a shaft's predetermined curvature to position the distal end of the shaft near a target site. Such mechanisms, techniques and devices include those described in U.S. patent application Ser. Nos. 11/848,565, 11/848,564, and 11/848,562, each of which is incorporated herein by reference in their entirety for all purposes.

Figure 4A:
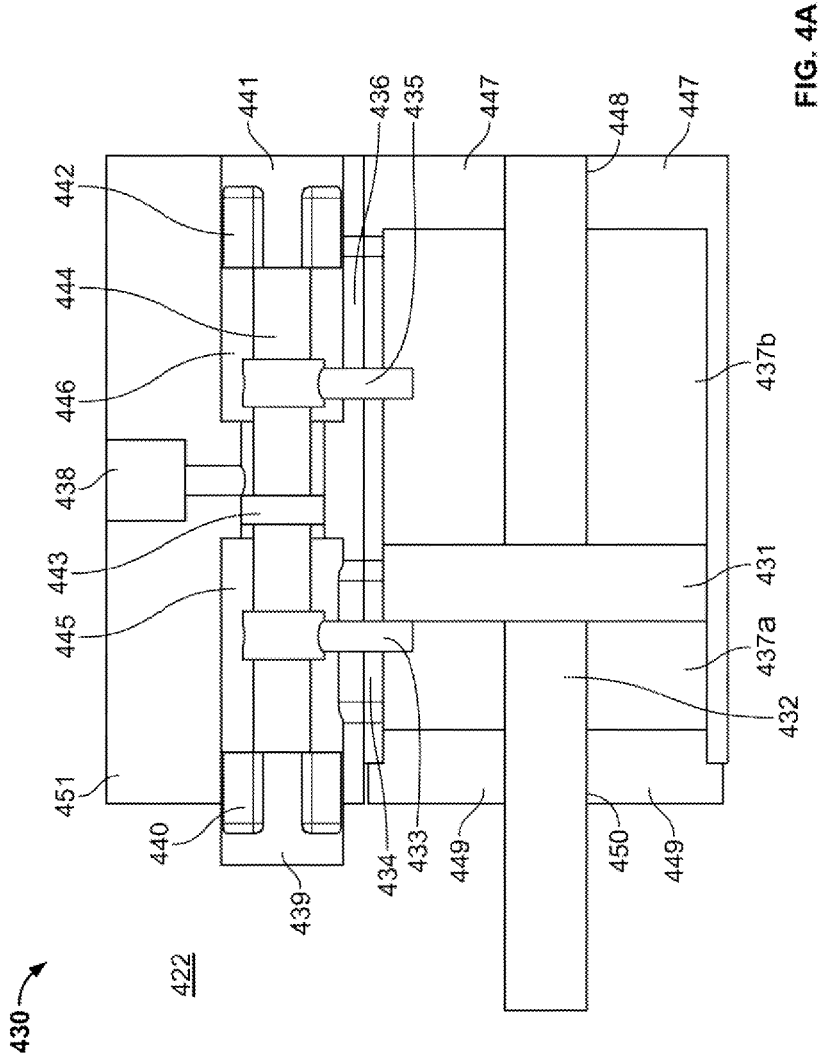
FIG. 4A illustrates the cross sectional view of a variation of a double action vacuum powered mechanism in a proximal position.
Figure 4B:
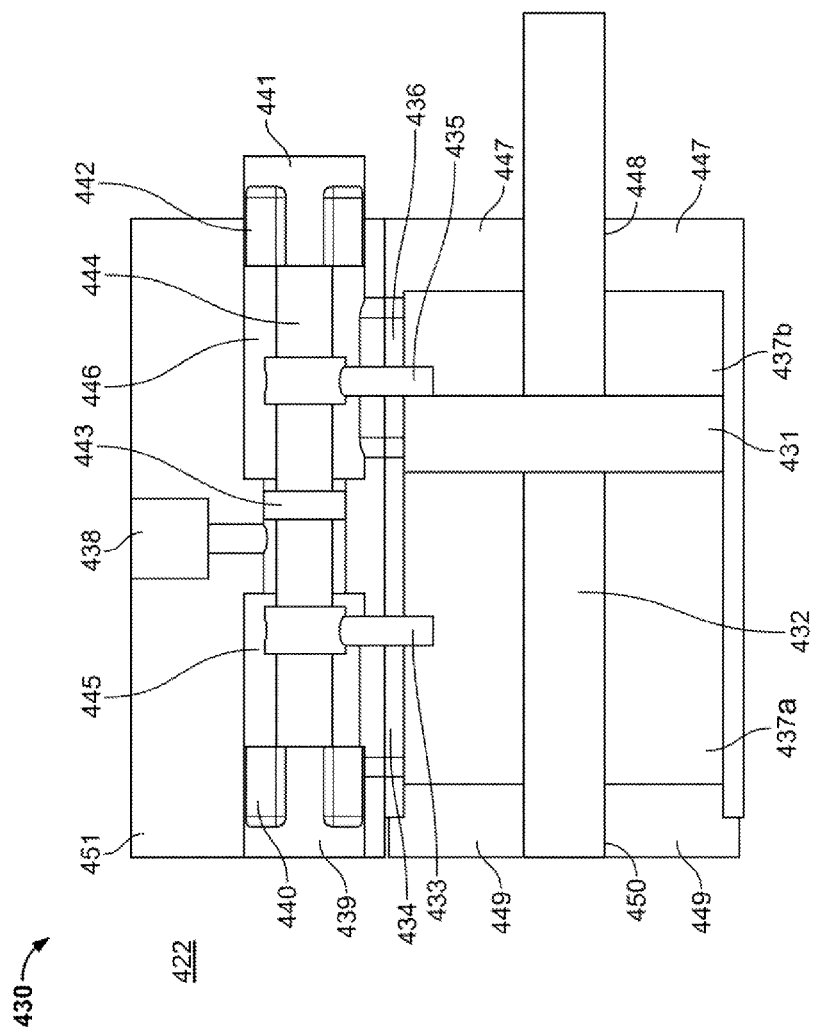
FIG. 4B illustrates a cross sectional view of the double action vacuum powered mechanism of FIG. 4A in a distal position.

FIG. 4A shows a cross sectional view of another variation of a double action vacuum powered mechanism or motor in a proximal position, while FIG. 4B shows the double action vacuum powered mechanism or motor in a distal position.

Referring to FIG. 4A-4B, the vacuum powered mechanism 430 includes a piston 431 having a piston shaft 432. The piston 431 including at least a portion of the piston shaft 432 are positioned within a cylinder chamber 437. The piston 431 divides or separates the cylinder chamber 437 into a proximal cylinder chamber 437a and a distal cylinder chamber 437b.

The piston 431 may reciprocate proximally and distally within the cylinder chamber 437 when vacuum and ambient air are alternately applied to opposite sides of the piston 431 in cylinder chambers 437a and/or 437b. The piston 431 and piston shaft 432 may reciprocate, and the reciprocating piston shaft 432 may conduct reciprocating motion output.

A proximal shuttle pin 433 is connected to a shuttle 444. The shuttle pin 433 may be actuated by the piston 431 when the piston 431 moves in the proximal direction and contacts the proximal shuttle pin 433. Actuation of the proximal shuttle pin 433 by the piston results in movement of the shuttle 444 in the proximal direction.

A distal shuttle pin 435 is also connected to the shuttle 444. The distal shuttle pin 435 may be actuated by the piston 431 when the piston 431 moves in the distal direction and contacts the distal shuttle pin 435. Actuation of the distal shuttle pin 435 by the piston results in movement of the shuttle 444 in the distal direction. Indeed, movement of the piston in the proximal direction results in movement of the shuttle in the proximal direction via contact with the proximal shuttle pin 433, while movement of the piston in the distal direction results in movement of the shuttle in the distal direction via contact with the distal shuttle pin 435.

The shuttle 444 is positioned within a shuttle chamber. The shuttle 444 includes a shuttle valve 443 or flange which may extend radially therefrom, which separates or divides the shuttle chamber into a proximal shuttle chamber 445 and a distal shuttle chamber 446.

Proximal shuttle chamber 445 may be in fluid communication with proximal cylinder chamber 437a via proximal shuttle pin slot 434. Proximal shuttle pin slot 434 also provides an opening in which the proximal shuttle pin 433 may translate between proximal and distal positions. Distal shuttle chamber 446 may be in fluid communication with distal cylinder chamber 437b via distal shuttle pin slot 436. Distal shuttle pin slot 436 also provides an opening in which the distal shuttle pin 435 may translate between proximal and distal positions.

The shuttle (444) may also include a proximal ambient air seal (439), a proximal cruciform (440), a distal ambient air seal (441), a distal cruciform (442), and a central shaft connecting the above components.

A vacuum port (438) may be connected to an external or internal vacuum source or supply to evacuate the proximal shuttle chamber 445 and the distal shuttle chamber 446. The vacuum port 438 may allow for evacuation by vacuum of the proximal cylinder chamber 437a via the proximal shuttle pin slot 434 and the proximal shuttle chamber 445. The vacuum port may allow for evacuation by vacuum of the distal cylinder chamber 437b via the distal shuttle pin slot 436 and the distal shuttle chamber 446.

For example, Proximal Cylinder Chamber (437a) may be evacuated by vacuum when in fluid communication with the external vacuum source via the Vacuum Port (438), Proximal Shuttle Chamber (445), and Proximal Shuttle Pin Slot 434. Distal Cylinder Chamber (437b) may be evacuated by vacuum when in communication with the external vacuum source via the Vacuum Port (438), Distal Shuttle Chamber (446), and Distal Shuttle Pin Slot (436). Presence of vacuum in Proximal Cylinder Chamber 437a results in differential pressure between the proximal and distal sides of the Piston (431) that results in working force to move the Piston (431) proximally when ambient air is in the distal Cylinder Chamber (437b). Alternately, ambient air (422) in proximal Cylinder Chamber 437a applies working force to move the Piston (431) distally when the Distal Cylinder Chamber (437b) is evacuated.

The shuttle 44 may be translated or positioned in a shuttle chamber such that Shuttle valve 443 can seal against the shuttle block (451) to the distal side of the vacuum port (438) to allow the proximal shuttle chamber (445) and proximal cylinder chamber (437a) to be evacuated by communicating with an external vacuum supply. Alternatively, the shuttle 444 may be translated or positioned in a shuttle chamber such that the shuttle valve 443 may seal against the shuttle block (451) to the proximal side of the vacuum port (438) to allow the distal shuttle chamber (446) and distal cylinder chamber (437b) to be evacuated by communicating with the external vacuum supply.

The proximal shuttle chamber (445) may allow for fluid communication between the Vacuum Port (438) and the Proximal Cylinder Chamber (437a) through the Proximal shuttle pin Slot (434). The proximal shuttle chamber (445) may also allow for fluid communication between the Proximal Cylinder Chamber 437a and ambient air when the Proximal Shuttle Seal (439) is in the proximal position, i.e., an open or unsealed position.

The Distal Shuttle Chamber (446) may allow for fluid communication between the Vacuum Port (438) and the Distal Cylinder Chamber (437b) through the Distal shuttle pin Slot (436). The Distal Shuttle Chamber (446) may allow for fluid communication between the Distal Cylinder Chamber 437b and ambient air when the Distal Shuttle Seal 41 is in the distal position, i.e., an open or unsealed position.

The proximal ambient air seal (439) of the shuttle 44 may seal against shuttle block (421) to prevent ambient air leakage into proximal shuttle chamber 445 when the proximal shuttle chamber (445) is evacuated. Also, the proximal cruciform (440) can maintain shuttle (444) position concentricity relative to proximal shuttle chamber (445), e.g., when the shuttle (444) moves to a proximal position and vents ambient air to the proximal shuttle chamber (445).

The distal ambient air seal (441) of the shuttle 444 may seal against shuttle block (51) to prevent ambient air leakage into distal shuttle chamber 446 when the distal shuttle chamber (446) is evacuated. Also, the distal cruciform (442) can maintain shuttle (444) position concentricity relative to distal shuttle chamber (446), e.g., when the shuttle (444) moves to a distal position and vents ambient air to the distal shuttle chamber (446).

The vacuum powered mechanism 430 may also include a Distal Cylinder Endcap (447), which may prevent or minimize fluid communication between ambient air and the Distal Cylinder Chamber (437b) in addition to providing a sealing and bearing surface with the Piston Shaft (432). The vacuum powered mechanism 430 may also include a Distal Cylinder Endcap Seal (448), which may prevent or minimize ambient air leakage between the Distal Cylinder Endcap (447) and the Piston Shaft (432), e.g., when the Distal Cylinder Chamber (437b) is evacuated.

The vacuum powered mechanism 430 may also include a Proximal Cylinder Endcap (449), which may prevent or minimize fluid communication between ambient air and the Proximal Cylinder Chamber (437a) in addition to providing a sealing and bearing surface with the Piston Shaft (432). The vacuum powered mechanism 430 may also include a Proximal Cylinder Endcap Seal (450), which may prevent or minimize ambient air leakage between the Proximal Cylinder Endcap (449) and the Piston Shaft (432), e.g., when the Proximal Cylinder Chamber (437a) is evacuated.

The piston shaft 432 may seal against the endplates or endcaps 447, 449 or shuttle block 451 to prevent or minimize loss of vacuum to ambient air 422. Also, various seals known to person of skill in the art may be utilized to seal the piston shaft against the endplates or endcaps 447, 449 or shuttle block 451.

A shuttle block 451 or other frame, structure, or casing may provide an outer structure for the vacuum powered mechanism 430. Ambient air 422 refers to air at atmospheric pressure which is located outside of the vacuum powered mechanism. Ambient air 422 may also be allowed to flow inside various chambers of the vacuum powered mechanism during use of the mechanism as described herein.

In use or in operation, the vacuum powered mechanism 430 operates by a pneumatic mechanism, method or logic that does not require inertial mass to move the mechanism through transition (such as a flywheel) and that uses an external or internal vacuum source to provide the force to cause reciprocating motion of the piston 31 in both proximal and distal directions.

For example, the vacuum port 438 may be opened to the distal cylinder chamber 437b to evacuate the distal cylinder chamber 437b and ambient air is closed to the distal cylinder chamber 37b, while ambient air is opened to the proximal cylinder chamber 437a and the vacuum port is closed to the proximal cylinder chamber 437b. The Piston advances toward a distal position due to the vacuum inside the distal cylinder chamber 437b, on the distal side of the piston 431 and the ambient air pressure in the proximal cylinder chamber, on the proximal side of the piston 431.

As a result of the differential pressure created on opposite sides of the piston 431, the Piston 431 moves through the chamber and contacts the distal shuttle pin 435, causing the shuttle 444 to move from a proximal position to distal position in the shuttle chamber. As a result, the vacuum seal 443 on the shuttle 444 moves from the proximal side of vacuum port 438 to the distal side of the vacuum port 38, opening the vacuum port 438 to the proximal cylinder chamber 437a to evacuate the proximal cylinder chamber 437a, and closing the vacuum port 438 to the distal cylinder chamber 437b. Also, the distal seal 441 on the shuttle 444 opens the ambient air 422 to vent the distal cylinder chamber 437b to ambient pressure, and the proximal seal 439 on the shuttle 444 closes the ambient air vent to the proximal cylinder chamber 437a.

It may be necessary to have adequate evacuated volume in the distal cylinder chamber 437b to cause the Piston (431) to continue translating distally after the Shuttle Valve (443) shuts off vacuum from vacuum port 438 to the distal cylinder chamber 437b. This may ensure that the shuttle 444 continues to translate in the distal direction as a result of the moving piston contacting the distal shuttle pin and thereby moving the shuttle 444, such that shuttle valve 443 completely passes vacuum port 438, shutting off the vacuum to the distal cylinder chamber 437b, in manner that avoids or minimizes valve flutter or unwanted fluctuation of the valve 443 between proximal and distal positions in the shuttle chamber.

The piston 431 then reverses direction and moves in the proximal direction, due to the vacuum inside the proximal cylinder chamber 437a, on the proximal side of the Piston and the ambient air pressure in the distal cylinder chamber 437b, on the distal side of the piston 431.

As a result of the differential pressure created on opposite sides of the piston 431, the piston 431 moves through its dwell or the cylinder chamber and contacts the proximal shuttle pin 433, causing the Shuttle 444 to move from its distal position to proximal position in the shuttle chamber. As a result, the vacuum seal 443 on the shuttle 444 moves from the distal side of the Vacuum Port 438 to the proximal side of the vacuum port 38, opening the vacuum port 438 to the distal cylinder chamber 37*b* to evacuate the distal cylinder chamber 437*b*, and closing the vacuum port 38 to the proximal cylinder chamber 437*b*. Also, the Proximal Seal 439 on the Shuttle 444 opens the ambient air 422 to vent the proximal Cylinder chamber 437*a* to ambient pressure, and the Distal Seal 441 on the Shuttle 444 closes the ambient air vent to the distal cylinder chamber 437*b*.

Again, it may be necessary to have adequate evacuated volume in the proximal cylinder chamber 437*a* to cause the Piston (431) to continue translating proximally after the Shuttle Valve (443) shuts off vacuum from vacuum port 438 to the proximal cylinder chamber 437*a*. This may ensure that the shuttle 444 continues to translate in the proximal direction as a result of the moving piston contacting the proximal shuttle pin and thereby moving the shuttle 444, such that shuttle valve 443 completely passes vacuum port 438, shutting off the vacuum to the proximal cylinder chamber 437*b*, in manner that avoids or minimizes valve flutter or unwanted fluctuation of the valve 443 between proximal and distal positions in the shuttle chamber.

Consequently, the mechanism has completed one cycle and is free to continue reciprocating as described above by alternating air pressure on opposite sides of the piston, as long as adequate vacuum is available to the mechanism. Indeed, the above Steps may repeat as necessary such that the vacuum powered mechanism creates a reciprocating motion until the vacuum source is disconnected, turned off, or if the vacuum is inadequate to overcome the force required to move the Piston 431.

In certain variations of a vacuum powered mechanism, a vacuum may be created in the "dead space" on the distal or proximal end of the Cylinder that is adequate to cause the Piston to continue moving distally or proximally after the external vacuum source is shut off from the Cylinder. The "dead space" volume in the proximal or distal end of the Cylinder serves as an "accumulator" that encourages the Piston to continue moving distally or proximally thereby eliminating the need for mass to create inertia to move the valve through transitions from one state to another.

In another variation, a method of reducing pneumatic valve instability or flutter caused by the valve or Shuttle attempting to move back and forth between states includes exposing one side of the shuttle valve to the vacuum source and the opposite side of the shuttle valve to ambient air. This may cause the shuttle valve to move in the direction of the vacuum and will more fully open the port connecting the ambient air to the Cylinder.

The reciprocating motion of the mechanism may be utilized to actuate a cutting device or to operate or actuate another device, e.g., another medical device. In certain variations, cutting device may be positioned by maneuvering a flexible or malleable shaft of the device e.g., manually or automatically. The shaft may be maneuvered or positioned around sensitive tissues or structures in the human body by changing the shape of the shaft. For example, extending or retracting an outer sheath or cannula on the shaft or advancing or retracting the shaft relative to the outer sheath, thereby allowing improved maneuverability of the shaft around structures or within confined spaces may be performed, e.g., allowing a shaft's predetermined curvature to position the distal end of the shaft near a target site. Such mechanisms, techniques and devices include those described in U.S. patent application Ser. Nos. 11/848,565, 11/848,564, and 11/848,562, each of which is incorporated herein by reference in their entirety for all purposes.

Further describing operations of a variation of a mechanism as illustrated in FIGS. 4A-4B, the shuttle 444 may start in the proximal or distal positions. In certain variations, a small spring (not shown) may be used to position the piston and/or the shuttle component in a particular starting position.

FIG. 4A shows the shuttle 444 starting in the proximal position. When external vacuum is applied to the mechanism through the Vacuum Port (438), the Shuttle Valve (443) is on the proximal side of the Vacuum Port (448) which results in evacuation of the air in the Distal Cylinder Chamber (437*b*), the Distal Shuttle Pin Slot (436), and the Distal Shuttle Chamber (446). Consequently, the differential pressure on the proximal and distal sides of the Piston (431) causes the piston to move distally.

The vacuum may apply a force greater than the frictional forces acting on the Piston in addition to the forces required by the mechanism to perform work.

As the Piston (431) moves distally, it contacts the Distal Shuttle Pin (435) and moves the Shuttle (444) distally. As a result, the Shuttle Valve (443) closes off the Vacuum Port (438) to the distal side of the mechanism.

It may be necessary to have adequate evacuated volume on the distal side of the chamber or in the distal cylinder chamber 437*b* to cause the Piston (431) to continue translating distally after the Shuttle Valve (443) shuts off vacuum to the distal side of the mechanism or to the distal cylinder chamber 437*b*.

As the Shuttle (444) moves distally, the Distal Ambient Air Seal (441) opens to allow ambient air from outside of the mechanism to flow into the distal side of the mechanism and fill the evacuated volume including the Distal Cylinder Chamber (437*b*), the Distal Shuttle Pin Slot (436), and the Distal Shuttle Chamber (446). Additionally, the Proximal Ambient Air Seal (439) closes and the Shuttle Valve (443) opens the vacuum port 438 to the proximal side of the mechanism and/or to the proximal cylinder chamber 437*a*.

The Shuttle Valve (443) moves to the distal side of the Vacuum Port (438) which results in evacuation of the air in the Proximal Cylinder Chamber (437*a*), the Proximal Shuttle Pin Slot (434), and the Proximal Shuttle Chamber (445). Consequently, the differential pressure on the proximal and distal sides of the Piston (431) causes the piston to move proximally.

As the Piston (431) moves proximally, it contacts the Proximal Shuttle Pin (433), and moves the Shuttle (444) proximally. As a result, the Shuttle Valve (443) closes off the Vacuum Port (438) to the proximal side of the mechanism or to the proximal cylinder chamber 437*a*.

It may be necessary to have adequate evacuated volume on the proximal side of the chamber or in the proximal cylinder chamber 437*a* to cause the Piston (431) to continue translating proximally after the Shuttle Valve (443) shuts off vacuum to the proximal side of the mechanism or to the proximal cylinder chamber 437*a*.

As the Shuttle (444) moves proximally, the Proximal Ambient Air Seal (439) opens to allow ambient air from outside of the mechanism to flow into the proximal side of the mechanism and fill the evacuated volume including the Proximal Cylinder Chamber (437*a*), the Proximal Shuttle Pin Slot (434), and the Proximal Shuttle Chamber (445). Additionally, the Distal Ambient Air Seal (441) closes and the Shuttle Valve (443) opens the vacuum port 8 to the distal side of the mechanism and/or the distal cylinder chamber 437*b*.

The Shuttle Valve (443) is on the proximal side of the Vacuum Port (438) which results in the mechanism being returned to the starting position described above. Consequently, the mechanism has completed one cycle and is free to continue reciprocating as described above as long as adequate vacuum is available to the mechanism.

Figure 5A:
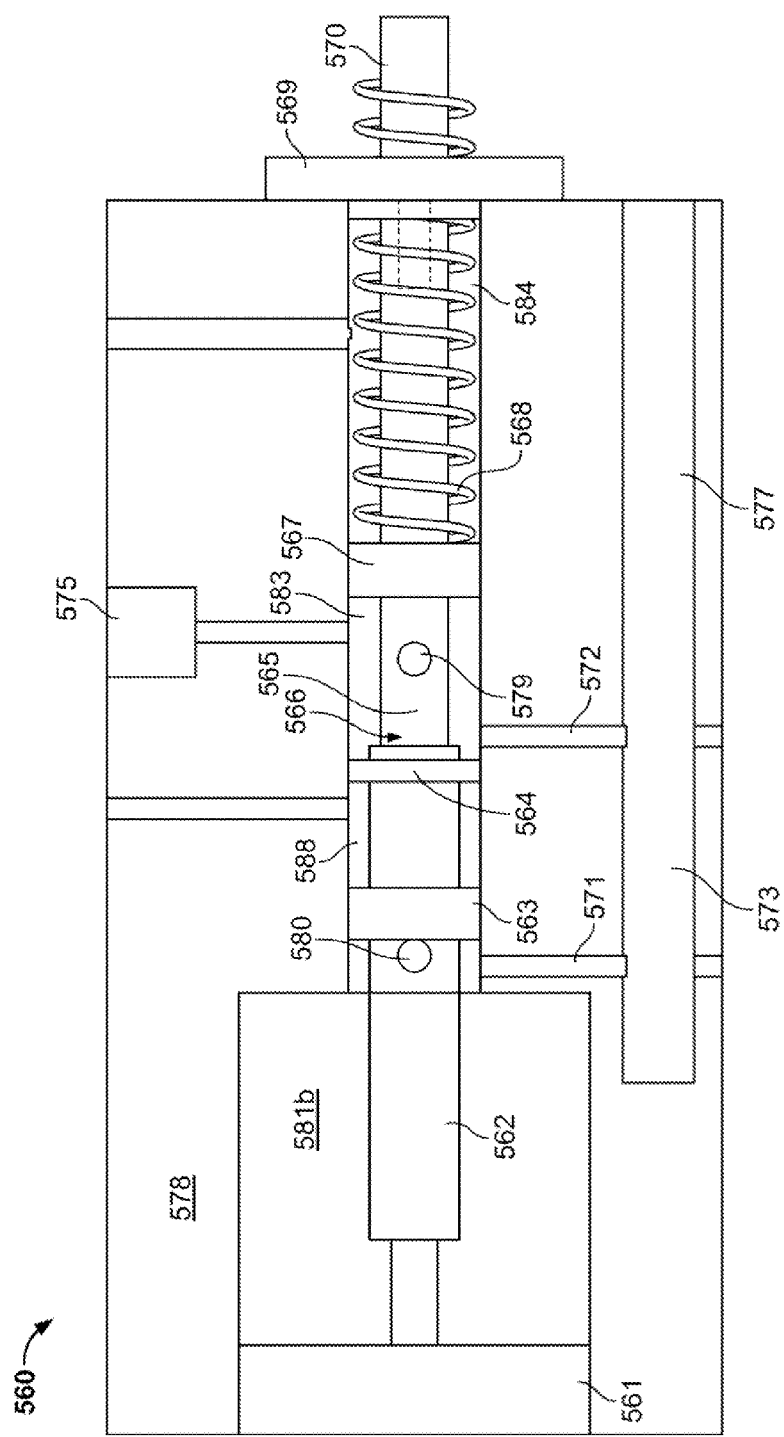
FIG. 5A illustrates a cross sectional view of a variation of a single action vacuum powered mechanism using a spring return system in a proximal position.
Figure 5B:
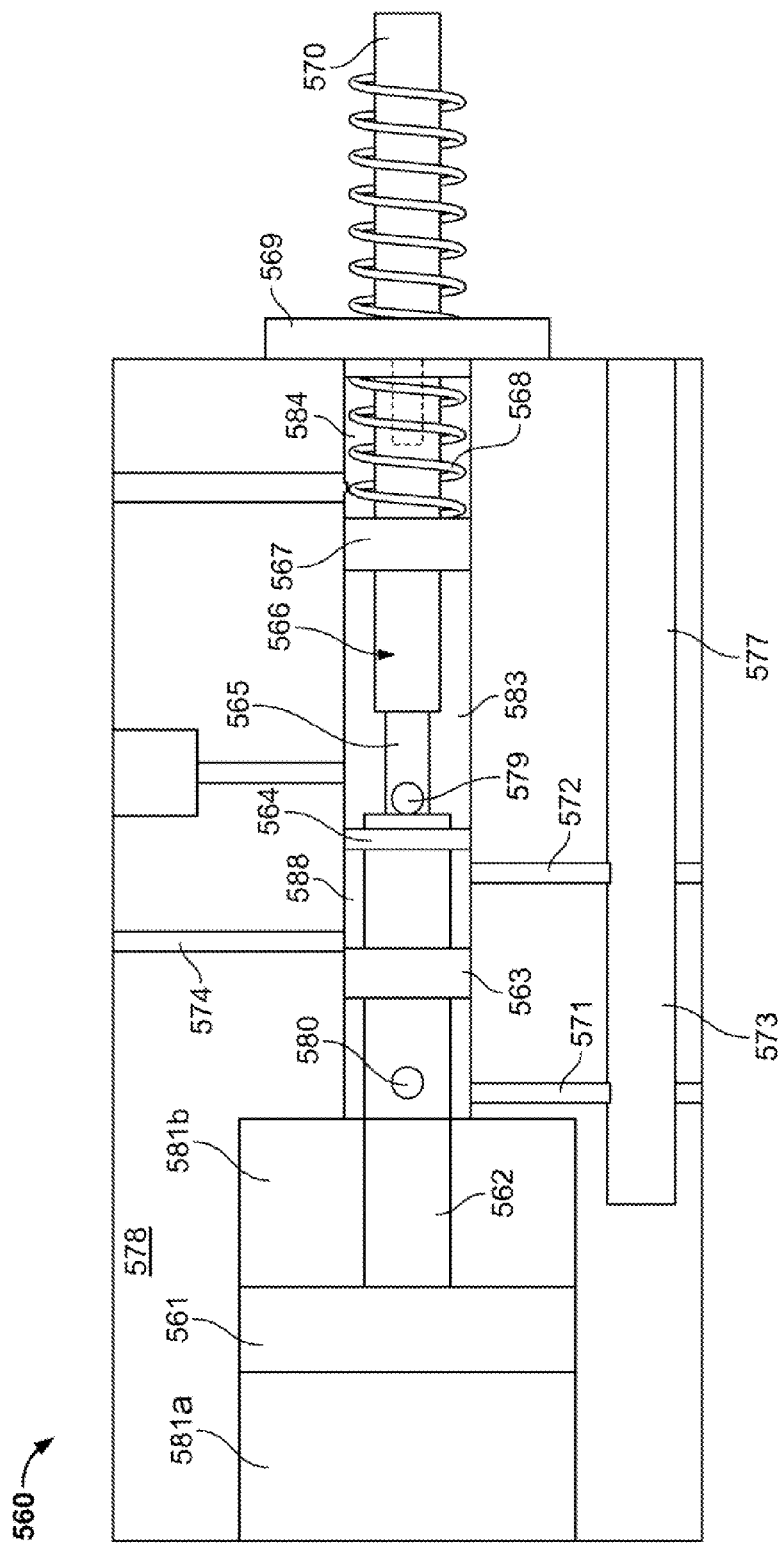
FIG. 5B illustrates a cross sectional view of a single action vacuum powered mechanisms of FIG. 5A in a distal position.

FIGS. 5A-5B show another variation of a vacuum powered mechanism 560 or motor including a spring return mechanism. FIG. 5A shows the mechanism with a Piston 561 in a starting or proximal position, and FIG. 5B shows the mechanism with a Piston 561 in a distal position.

Referring to FIG. 5A-5B, the vacuum powered mechanism 560 includes a piston 561 having a piston shaft 62. The piston 561 including at least a portion of the piston shaft 562 are positioned within a cylinder chamber 581. The piston 561 divides or separates the cylinder chamber 581 into a proximal cylinder chamber 581a and a distal cylinder chamber 581b. The piston 561 may reciprocate distally within the cylinder chamber 581 when the distal side of the piston 561 is evacuated or when distal cylinder chamber 581b is evacuated. Ambient air may be or may always be present on the proximal side of the piston 561 or in the proximal cylinder chamber 581a. Cylinder chamber 581a may be open to ambient air or may always be open to ambient air. The piston shaft 565 may reciprocate along with the piston 561, and the reciprocating piston shaft 565 may conduct reciprocating motion output. The piston shaft may serve to transmit the motion from the piston as the mechanism output.

A shuttle 562 may be connected to the Piston (561) and the shuttle 562 may reciprocate along with the Piston 561. The shuttle 562 may be positioned in a shuttle chamber. The shuttle includes a proximal seal flange 563 which may be integral to the shuttle 562 and/or extend radially therefrom. The seal flange 563 provides a seal between the Ambient Air Conduit (574) and the Distal Cylinder Chamber (581b) when the Distal Cylinder Chamber (581b) is evacuated. Proximal Seal Flange 563 may also contact a Proximal Stop Pin (580) to stop the proximal movement of the Shuttle (562).

The shuttle may also include a shuttle valve 564, which may be integral to the shuttle and/or may extend radially therefrom. The shuttle valve 564 may separate or divide the shuttle chamber into a proximal shuttle chamber 588, on the proximal side of the valve 564, and a vacuum shuttle chamber 583 on the distal side of the valve 564. The Shuttle Valve 564 provides a seal, which may seal, e.g., against the shuttle block 578, to the distal or proximal side of the distal conduit 572. The shuttle valve 564 may provide a seal to the proximal side of the distal conduit 572 to open the distal conduit 572, and the distal cylinder chamber 581b, to a vacuum port 575 to allow the distal cylinder chamber 581b to be evacuated by communicating with an external vacuum supply.

The shuttle valve 564 may also provide a seal to the distal side of the distal conduit 572 to open the distal conduit 572, and the distal cylinder chamber 581b, to an ambient air conduit 574 to allow the distal cylinder chamber 581b to be open to ambient air.

The piston shaft 565 may be integral to the piston 61 on the proximal end of the piston shaft 565 and integral to the distal piston shaft 570 (i.e., the external portion of the piston shaft 565 located at the distal end of the piston shaft 565. A Shuttle Return Surface (566) is Integral to the Piston Shaft (565) and serves to contact the distal end of the Shuttle (562) to motivate it proximally when the Piston 561 and piston shaft 565 are translating in the proximal direction.

The piston shaft 565 may also include a Distal Seal Flange (567), which may extend radially therefrom. The distal seal flange 567 may seal ambient air in the return spring chamber 584, sealing off the return spring chamber 584 from the shuttle vacuum chamber 583. The distal seal flange may also provide a surface for a Return Spring (568) to act upon to motivate or translate the Piston Shaft (565) proximally or in the proximal direction during a return stroke.

A Return Spring (568), is positioned in the return spring chamber 584 and stores mechanical energy by compressing during the distal stroke of the mechanism, i.e., when the piston and piston shaft are moved in the distal direction. The mechanical energy is released when the Return Spring 568 motivates the Piston Shaft 565 proximally during the return stroke of the mechanism.

The mechanism 560 may include a Distal End Plate (569) which serves as a distal stop for the Return Spring (568).

The mechanism 560 may also include various conduits. A Proximal Conduit (571) may provide a connection or conduit for fluid communication between the Distal Cylinder Chamber (581b) and a Parallel Conduit (573). A Distal Conduit (572), as identified above, may provide a connection or conduit for fluid communication between the Proximal Shuttle Chamber (588) and the Parallel Conduit (573). The Parallel Conduit (573) may provide a connection or conduit for fluid communication between the Proximal Conduit (571) and the Distal Conduit (572). The Ambient Air Conduit (574) may provide a conduit to allow ambient air to vent proximal shuttle chamber 588 and Distal Cylinder Chamber (581b) depending on the positioning of shuttle valve 564 relative to the distal conduit 572.

The Vacuum Port (575) connects the mechanism to an external vacuum source and evacuates shuttle vacuum chamber 583 and may evacuate distal cylinder chamber 581b depending on the positioning of shuttle valve 564 relative to the distal conduit 572.

The mechanism 560 may also include a Return Spring Vent (576) which vents the Return Spring Chamber (584) to ambient air to maintain ambient air pressure in the Return Spring Chamber (584) as the chamber changes volume due to compression and extension of the Return Spring (568). The Return spring chamber 84 contains the return spring 68. The return spring chamber 84 may be or may always be at ambient pressure via the return spring vent 76.

A Distal Parallel Conduit (77) may also be provided. The distal parallel conduit 77 may be an Artifact from machining the mechanism Block (78) and the Distal Parallel Conduit 77 may be plugged at the distal end prior to use.

A mechanism block 578 or other frame, structure, or casing may provide an outer structure for the vacuum powered mechanism 560. Ambient air 522 refers to air at atmospheric pressure which is located outside of the vacuum powered mechanism. Ambient air 522 may also be allowed to flow inside various chambers of the vacuum powered mechanism during use of the mechanism as described herein.

A Distal Stop Pin (579) provides a distal stop for the Shuttle (562) by preventing distal translation of the Shuttle (562) beyond the location of the distal stop pin 579.

A Proximal Stop Pin and Ball Plunger (580) may provide a proximal stop for the Shuttle (562) when in contact with the Proximal Seal Flange (563). The Ball Plunger provides normal force on the Shuttle to increase the force required to translate the shuttle laterally thereby reducing or eliminating the likelihood of valve "flutter" or unwanted fluctuation of the valve 564 between proximal and distal positions in the shuttle chamber relative to distal conduit 572.

The Distal Cylinder Chamber (581b) alternates between vacuum and ambient pressure to motivate the Piston (561) distally when the Distal Cylinder Chamber (581b) is in vacuum and to allow the Return Spring (568) to motivate the Piston Shaft (562) and/or piston 61 proximally when the Distal Cylinder Chamber 581b is at ambient pressure.

The Proximal Shuttle Chamber (588) may be at ambient pressure or may always be at ambient pressure. The Shuttle Vacuum Chamber (583) may be evacuated or may always be evacuated when an external vacuum source is connected to the Vacuum Port (575).

In use or in operation, the vacuum powered mechanism 560 operates by a pneumatic mechanism, method or logic whereby a vacuum mechanism valve sequence includes shutting off the vacuum source from the distal cylinder chamber 81b or the mechanism to allow the piston to return to its home position without venting the vacuum source to ambient pressure. As a result, the vacuum pressure remains consistent in the cutting and evacuation system portion of the device. The pneumatic mechanism, method or logic for a piston system that does not require inertial mass to move the mechanism through transition (such as a flywheel) and that uses an external or internal vacuum source to provide the force to cause reciprocating motion in one direction and a return spring to provide the force to cause reciprocating motion in the reverse direction may include the following steps.

For example, a vacuum may be open to the distal Cylinder chamber 581b while ambient air is closed to that chamber. The Piston 561 advances in the distal direction, toward a distal position due to the vacuum inside the distal cylinder chamber 521b and ambient pressure in the proximal cylinder chamber 581a, on the proximal side of the Piston 561. Distal advancement of the Piston 561 compresses the Compression Spring 568, where the vacuum force should or may be great enough to overcome friction in order to compress the Compression Spring 568.

When the piston 561 moves, the piston 561 contacts Shuttle 562 and advances the Shuttle 562 such that the shuttle valve 564 cuts off the vacuum to the distal Cylinder chamber 581b and the Compression Spring 568 continues to compress as the Piston 561 advances in the distal direction. Piston 561 may continue to advance distally (e.g., even after the vacuum is cut off to distal cylinder chamber 581b) due to evacuated volume on the distal side of the Cylinder in the distal cylinder chamber 581b, which should or may be great enough to overcome friction and to continue compressing the Compression Spring 568 and advancing the shuttle 562 to allow ambient air to flow into the distal cylinder chamber 581b by opening distal conduit 572 and distal cylinder chamber 581b to ambient air conduit 574.

The Piston 561 may retract in the proximal direction to a proximal position due to the force of the Compression Spring 568 and a loss of vacuum in the distal cylinder chamber 581b resulting from ambient air flowing into the distal cylinder chamber 581b. The Piston Shaft 562 contacts the Shuttle and moves the shuttle in a proximal direction, thus cutting off ambient air conduit 574 and ambient air flow to the distal Cylinder chamber 581b. The Piston Shaft 562 continues moving the Shuttle 562 proximally, eventually opening the distal conduit 572 and distal cylinder chamber 581b to vacuum port 575 such that the vacuum connection is open to the distal cylinder chamber 581b.

The mechanism is free to continue reciprocating as described above by creating a pressure differential on opposite sides of the piston as long as adequate vacuum is available to the mechanism. The above steps may repeat as necessary such that the vacuum powered motor creates a reciprocating motion unless or until the vacuum source is disconnected, turned off, or if the vacuum is inadequate to overcome the force required to compress the Compression Spring and overcome the internal friction or if the mechanism is stalled or halted.

In certain variations, Pneumatic valve instability or flutter caused by the shuttle or shuttle valve attempting to move back and forth between states, or between proximal and distal positions relative to distal conduit 572, may be reduced or eliminated by exposing one side of the shuttle valve 564 to the vacuum source and the opposite side of the Shuttle valve 564 to ambient air. This will cause the Shuttle or shuttle valve to move in the direction of the vacuum and will more fully open the distal conduit 572 to the ambient air conduit 574, thereby connecting the ambient air to the distal Cylinder chamber 581b.

In certain variations, a small normal force may be imparted on the Shuttle 562 to hold it in place to overcome unintended movement caused by friction against the Piston Shaft 565 or valve flutter caused by valve instability. This small normal force may be imparted in the form of a ball plunger.

In certain variations of a vacuum powered mechanism, an adequate volume is evacuated on the distal end of the Cylinder or from the distal cylinder chamber to cause the Piston to continue moving distally after the external vacuum source is shut off from the distal Cylinder chamber. The evacuated volume in the distal Cylinder chamber serves to encourage the Piston to continue moving distally after the external vacuum source is shut off from the volume of the distal cylinder chamber, thereby eliminating the need for inertial mass to move the valve through transitions from one state to another.

The reciprocating motion of the mechanism may be utilized to actuate a cutting device or to operate or actuate another device, e.g., another medical device. In certain variations, cutting device may be positioned by maneuvering a flexible or malleable shaft of the device e.g., manually or automatically. The shaft may be maneuvered or positioned around sensitive tissues or structures in the human body by changing the shape of the shaft. For example, extending or retracting an outer sheath or cannula on the shaft or advancing or retracting the shaft relative to the outer sheath, thereby allowing improved maneuverability of the shaft around structures or within confined spaces may be performed, e.g., allowing a shaft's predetermined curvature to position the distal end of the shaft near a target site. Such mechanisms, techniques and devices include those described in U.S. patent application Ser. Nos. 11/848,565, 11/848,564, and 11/848,562, each of which is incorporated herein by reference in their entirety for all purposes.

Further describing operations of a variation of a mechanism as illustrated in FIGS. 5A-5B, FIG. 5A shows a starting position for the mechanism with the Piston in a proximal position due to extension of the Return Spring (568).

When external vacuum is applied to the mechanism through the Vacuum Port (575), the Shuttle Valve (564) is on the proximal side of the Vacuum Port (75) and on the proximal side of the Distal Conduit (572). As a result, the vacuum is able to fluidly communicate with the Distal Cylinder Chamber (581b) which results in evacuation of the air in the Distal Cylinder Chamber (581b). Consequently, the differential pressure on the proximal and distal sides of the Piston (561) causes the piston to move distally.

As the Piston (561) moves distally, it compresses the Return Spring (568) thereby storing mechanical energy. The Proximal Shuttle Seal (563) prevents leakage of ambient air into the Distal Cylinder Chamber (581b). The Shuttle (562) "dwells" in position until the Piston (561) contacts the Shuttle (562) and motivates it in the distal direction. The Shuttle Valve (564) then closes off the Vacuum Port (575) to the Distal Conduit (572) thereby shutting off vacuum to the Distal Cylinder Chamber (581b).

It may be necessary to have adequate evacuated volume on the distal side of the chamber in the distal cylinder chamber 581b to cause the Primary Piston (561) to continue translating distally after the Shuttle Valve (564) shuts off vacuum to the distal conduit 572 and the distal cylinder chamber 581b.

As the Distal Cylinder Chamber (581) refills with ambient air, from ambient air conduit 574 via distal conduit 572 (which is now open to ambient air conduit 514 as shown in FIG. 5b), the Return Spring (568) motivates the Piston Shaft (565) proximally. The Shuttle "dwells" in position until the Shuttle Return Surface (566) on the Piston Shaft (565) contacts the Shuttle (562) and motivates the Shuttle (562) in the proximal direction.

The Shuttle Valve (564) moves from the distal side to the proximal side of the Distal Conduit (572) thereby opening the distal conduit 572 to the Vacuum Port (575) to evacuate the Distal Cylinder Chamber 581b).

The Shuttle (562) and the Piston 561 return to their proximal (starting) position and the mechanism has completed one cycle and is free to continue reciprocating as described above as long as adequate vacuum is available to the mechanism.

In any of the variations of vacuum powered mechanisms described herein, O-rings or other sealing components may be used to create a seal between surfaces but are not necessary if leakage around the seals is tolerable. Also, leakage around the seals may be reduced by using a lubricant of sufficient viscosity to fill the gap between the seal and the bore in which it operates.

The Shuttle may be configured in several positions including concentric with the Center Shaft, parallel to the Center Shaft, as a rotary valve, and so forth.

The vacuum powered mechanisms described herein may be utilized with or incorporated into a variety of medical devices. For example, the vacuum powered mechanisms may be utilized to reciprocate a cutter on a distal end of a malleable shaft which may be manipulated or adjusted manually or automatically or a flexible shaft having a predetermined curvature which is manipulated through advancement or retraction through a cannula or other sheath as illustrated and described in U.S. patent application Ser. Nos. 11/848,565, 11/848,564, and 11/848,562, each of which is incorporated herein by reference in their entirety for all purposes. U.S. Patent Application No. 61/360,429 is also incorporated herein by reference in its entirety for all purposes.

In certain variations of a device having a curved flexible shaft, a rigid or semi-rigid straight sheath may be assembled or connected to the device to cause the curved, flexible portion of the shaft to straighten as the sheath is advanced over the curved section or to cause the curved, flexible portion of the shaft to return to its curved shape as the sheath is retracted.

In other variations, a rigid or semi-rigid curved sheath may be assembled or connected to a device or end effector having a shaft with a curved, flexible portion to direct the shaft as it is advanced through the curved sheath.

In other variations, a rigid or semi-rigid curved sheath may be assembled or connected to a device or end effector having a shaft with a straight, flexible portion to direct the shaft as it is advanced through the curved sheath. The rigid or semi-rigid curved or straight sheathes may be assembled, connected, attached to or otherwise utilized with the cutting device. The various sheaths may be detachable from the devices or end effectors or affixed or attached to the devices and or end effectors.

In certain variations, the vacuum powered mechanisms described herein may also be utilized to reciprocate or actuate a reciprocating cutter of a device or end effector or to operate a device having a semi-rigid or rigid, curved end effector or a rigid or stiff shaft. A cutter, end effector and/or device may be operated by vacuum powered mechanisms or other motorized mechanisms or by hand.

FIG. 6 shows one variation of a rigid, curved end effector 4.0 or distal end of a device. The end effector 4.0 may include a scraping edge 4.1, a window 4.6, a reciprocating cutter 4.2., and/or a blunt distal tip 4.5. The end effector 4.0 may also include a rigid shaft 4.7. The rigid shaft 4.7 may have a shaft curvature section 4.3 and/or a shaft straight section 4.4. In certain variations, a fluid line 4.8, e.g., a saline line, may be attached to the end effector 4.0 or extend along or within the end effector 4.0. In certain variations, the end effector, distal end of a device, and/or shaft may be rigid, stiff, substantially rigid, or semi rigid.

The end effector 4.0 may be a component of a device, e.g., a cutting device or medical device. The end effector 4.0 may be positioned at a distal end of a cutting device or designed for use or attachment to a cutting device, medical device, or other device. The end effector 4.0 may be useful for various procedures requiring cutting and/or scraping of a variety of tissues including soft and hard tissues.

The Scraping Edge 4.1 is typically made from a rigid material, e.g., Stainless Steel, which may withstand cutting forces without substantially bending or deflecting the scraping edge 4.1. Other materials may be used as warranted by the desired clinical application. In certain variations, a semi-rigid material may be used. The Scraping Edge 4.1 may be used to cut or scrape various soft and hard tissues, such as intradiscal nucleus tissue, Vertebral End Plates, cartilage, ligament, bone, and other soft and hard tissues. The Scraping Edge 4.1 may be used to cut tissue free and/or to mobilize the tissue for evacuation through the Window 4.6 and through a lumen of the rigid shaft 4.7. The tissue may be evacuated to a Filter or collection receptacle.

The Scraping edge 4.1 may be affixed or attached to the rigid shaft 4.7 at any angle relative to the longitudinal axis of the Rigid Shaft 4.7. For example, the scraping edge 4.1 may be affixed or attached to the Rigid Shaft 4.7 at a an angle ranging from or between 0 to 180 degrees or 0 to 90 degrees relative to an axis of the Rigid Shaft 4.7. As shown in FIG. 6, in certain variations, the Scraping Edge 4.1 may be affixed or otherwise attached to the Rigid Shaft 4.7 in a position that is perpendicular or substantially perpendicular to the axis of the rigid shaft 4.7.

Where the Scraping Edge 4.1 is rigidly affixed to the Rigid Shaft 4.7 as shown in FIG. 6, the cutting and scraping actions of the scraping edge 4.1 may be accomplished by the operator manually moving the Scraping Edge 4.1 through manual movement of the rigid shaft 4.7 or the end effector 4.0 or a component thereof. Optionally, the cutting and scraping actions of the scraping edge 4.1 may be accomplished automatically or by motorized movement or operation of the rigid shaft 4.7 or the end effector 4.0 or a component thereof.

In certain variations, the Scraping Edge 4.1 may be affixed or attached to the Reciprocating Cutter 4.2, e.g., external to the Rigid Shaft 4.7, such that the scraping edge 4.1 can reciprocate in concert with the cutter (not shown). The scraping edge 4.1 may be affixed or attached to the reciprocating cutter 4.2 at any angle relative to the longitudinal axis of the Reciprocating Cutter 4.2. For example, the scraping edge 4.1 may be affixed or attached to the Reciprocating Cutter 4.2 at a an angle ranging from or between 0 to 180 degrees or 0 to 90 degrees relative to an axis of the Reciprocating Cutter 4.2. In certain variations, the Scraping Edge 4.1 may be affixed or otherwise attached to the Reciprocating Cutter 4.2 in a position that is perpendicular or substantially perpendicular to the axis of the Reciprocating Cutter 4.2.

The Scraping Edge 4.1 may be positioned at a location distal to the Window 4.6 and/or the scraping edge 4.1 may be predominately aligned with the Window 4.6 and/or positioned on the same side of the Rigid Shaft 4.7 as the Window 4.6. The Scraping Edge 4.1 may be positioned distal or proximal to the Window 4.6. Optionally, the scraping edge 4.1 may have exposed scraping surfaces at any location around the periphery of the Rigid Shaft 4.7 or reciprocating cutter 4.2.

In certain variations, the end effector 4.0 may be built without a Scraping Edge 4.1. Indeed, an end effector 4.0 may or may not include a scraping edge 4.1 depending on the desired clinical application. In certain variations, one or more scraping edges may be positioned on an end effector, e.g., a plurality of scraping edges may be positioned on an end effector.

Still referring to FIG. 6, the Reciprocating Cutter 4.2 may be positioned on the end effector 4.0 such that the reciprocating cutter 4.2 may advance and/or retract axially past the Window 4.6 to excise and evacuate tissue or mobilized tissue. The Reciprocating Cutter 4.2 may use a "scissor" action against the window 4.5 or against a section of the rigid shaft 4.7 to excise tissue.

The Window 4.6 is an opening in the Rigid Shaft 4.7 that permits the passage of tissue into the window 4.6 and into the path of the Reciprocating Cutter 4.2 such that the tissue can be cut and/or evacuated. The Window 4.6 or at least a portion of the perimeter or an edge of the window 4.6 may serve as a cutting edge to "plane" tissue and excise the tissue. Additionally, an edge of the Window 4.6 may provide a surface with which the Reciprocating Cutter 4.2 may scissor tissue as the reciprocating cutter 4.2 passes by the Window 4.6.

The Reciprocating Cutter 4.2 may be powered or actuated by any of the vacuum powered mechanisms described herein. Alternatively, the reciprocating cutter 4.2 or end effector may be actuated through a mechanism that is powered by hand or by other motorized mechanisms. In certain variations, a rotating cutter may be utilized and powered by any of the vacuum powered mechanisms described herein, by hand or by other motorized mechanisms.

The Rigid Shaft 4.7 may serve as the primary structure and/or outer envelope of the shaft of a device or cutting device to which the end effector is attached. The Rigid Shaft 4.7 may be curved or straight or the rigid shaft 4.7 may include curved and/or straight sections or portions. In certain variations, the rigid shaft 4.7 may be malleable to allow an operator or user to adjust or revise the curvature of the shaft 4.7 depending on the application or use. For example, the rigid shaft 4.7 may be bendable or the rigid shaft 4.7 may be annealed or softened in order to alter the shape or curve of the rigid shaft 4.7 by hand or machine. The rigid shaft may be annealed over the bendable portion of its length and hard near the distal extremity to reduce the likelihood of bending or damaging the shaft near the cutting window.

As shown in FIG. 6, a Shaft Curvature section 4.3 may be provided in the rigid shaft 4.7. The rigid shaft may include one or more shaft curvature sections. The shaft curvature section 4.3 allows the operator to position the end effector 4.0 or the distal end of the end effector 4.0 or the distal end of the cutting device or other device in an area of anatomy outside of the line-of-sight of the user. For example, the shaft curvature section 4.3 may allow the end effector 4.0 to be positioned within an intradiscal space. The radius of curvature of the rigid shaft 4.7 or the shaft curvature section 4.3 may be determined during manufacturing or it may be operator-adjustable.

The rigid shaft 4.7 may also include a Shaft Straight Section 4.4 which may be located proximal to the Shaft Curvature section 4.3. The rigid shaft may include one or more shaft straight sections.

A Blunt Distal Tip 4.5 may be provided on the end effector 4.0. The blunt distal tip 4.5 may significantly reduce, minimize or eliminate the likelihood of the end effector 4.0 or distal end of a device accidentally being advanced through or into tissue which is not the intended target. For example, the blunt distal tip 4.5 may reduce the likelihood or minimize the risk of the end effector 4.0 or distal end of the device being advanced through an annulus when the end effector 4.0 of a device is being used to cut intra-discal nucleus or for scraping and/or evacuating vertebral endplate material. The blunt distal tip 4.5 may cover all or a portion of the distal surface of the Scraping Edge 4.1. In variations where the entire distal surface or substantially the entire surface of the Scraping Edge 4.1 is covered with the Blunt Distal Tip 4.5, the Scraping Edge 4.1 may cut and/or scrape only when moved in the proximal direction or a lateral direction and not when moved in the distal direction. In other variations where the entire distal surface or substantially all of the distal surface of the Scraping Edge 4.1 is covered with the Blunt Distal Tip 4.5, the Scraping Edge 4.1 may cut and/or scrape in the distal direction or it may cut and/or scrape in the distal direction in a limited manner.

In certain variations, a fluid line 4.8 may be affixed or attached to the external or outside surface of the Rigid Shaft 4.7 as shown in FIG. 6. Optionally, the fluid line 4.8 may be contained inside the Rigid Shaft 4.7 by a separate lumen within the rigid shaft 4.7 or by allowing fluid to flow through the main shaft lumen. The fluid Line 4.8 allows fluids, e.g., saline, water, air, etc., to flow from a source of fluid external or internal to a device to the distal end of the end effector or the distal end of a device or cutting device.

A scraping edge 4.1 may be provided or located on an end effector 4.0 having a rigid shaft 4.7, where the rigid shaft 4.7 and scraping edge 4.1 allow side or axial forces to be applied to the rigid shaft, scraping edge, end effector and/or to a device attached to the end effector to effect scraping or cutting of tissue in a vertebral disc or tissue in another area of the anatomy, while minimizing or preventing deflection or bending of the end effector, shaft or scraping edge. A rigid end effector having a rigid shaft and/or scraping edge may permit or provide effective scraping and/or cutting of a target tissue. Optionally, a scraping edge may be positioned on the distal end of a flexible, semi-rigid or less rigid shaft or end effector and side forces may be applied to the scraping edge and shaft to effect scraping. In any of the above variations, axial advancement and retraction of the scraping device and/or end effector may result in the scraping or breaking up of tissue, such as vertebral disc tissue. Optionally, one or more scraping edges may be positioned adjacent to the cutting window to position the scraping edge nearly perpendicular to the direction of motion when a curved shaft is used.

In certain variations, an apparatus for scraping tissue in a subject is provided. The apparatus includes an end elector. The end effector includes a scraping edge positioned on a distal end of the end effector and one or more scraping wings, edges or protrusions positioned at an angle relative to the scraping edge such that the end effector may be actuated in a back and forth motion approximately perpendicular to the scraping edge to scrape or gather tissue, and/or actuated in a back and forth motion approximately perpendicular to the scraping wings to scrape or gather tissue. The scraping wings may serve to collect tissue at the cutting window opening to improve resection.

In certain variations, the end effector may include a scraping edge positioned on a distal end of the end effector and one or more scraping wings positioned at an angle relative to the scraping edge such that the scraping edge and scraping wings can provide a scraping motion in different directions.

Figure 7:
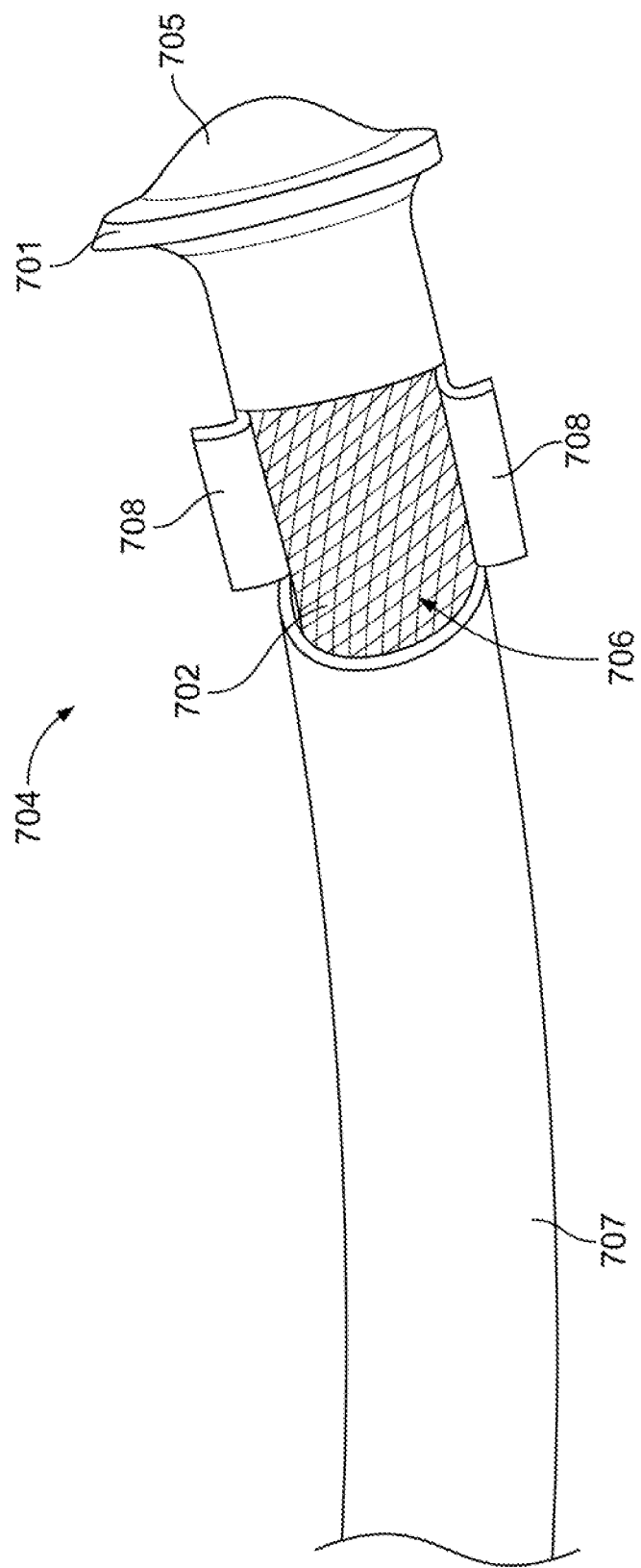
FIG. 7 illustrates a side view of a variation of an end effector.
Figure 9:
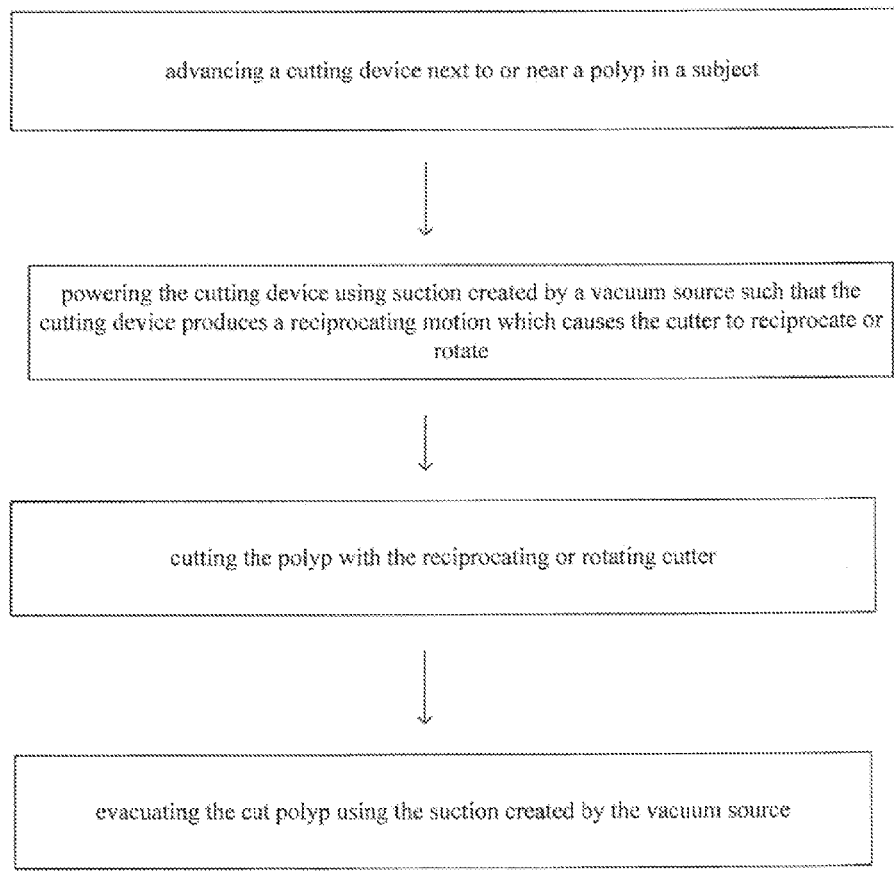
FIG. 9 illustrates a flow chart of a variation of a method for performing a polypectomy using a vacuum powered cutting device.
Figure 10:
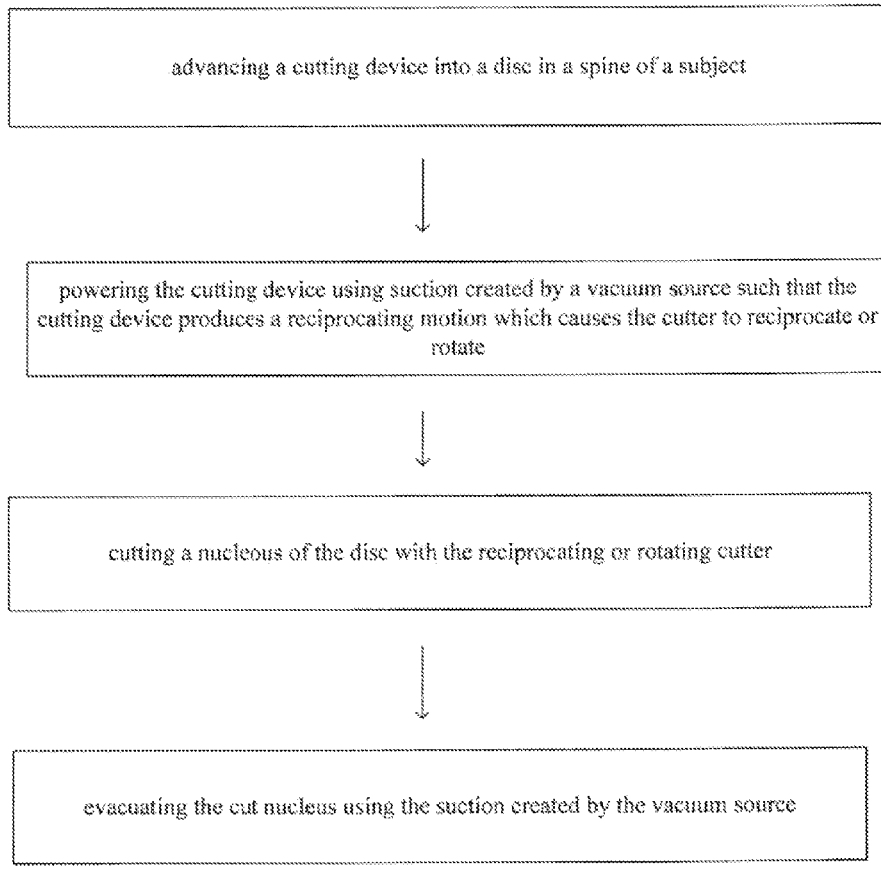
FIG. 10 illustrates a flow chart of a variation of a method for performing a discectomy using a vacuum powered cutting device.

FIG. 7 shows another variation of an end effector 704 or distal end of a cutting or scraping device. The end effector 704 may include a scraping edge 701, a window 706, a reciprocating cutter 702, and/or a blunt distal tip 705. The reciprocating cutter may be positioned within the end effector. The end effector 704 may include a rigid or flexible shaft 707. The end effector may include one or more wings 708 positioned at an angle to the scraping edge 701, e.g., such as but not necessarily next to the window 706. The wings 708 may be used to scrape, gather and/or cut tissue.

Wings 708 may be positioned on the end effector at an angle relative to the scraping edge 701. For example, the wings 708 may be positioned at an angle ranging from 0 to 90 degrees, e.g. at about 90 degrees, relative to the scraping edge 701. The wings 708 are positioned at an angle relative to the scraping edge 701 such that in use, the scraping edge 701 and wings 708 may work or scrape tissue in different directions. The end effector 704 may be used to cut or scrape a variety of tissues in various regions of the body. For example, the end effector may be utilized to cut, scrape and/or gather tissue in a spine or spinal disc, e.g., to perform a discectomy.

In the variations described herein, the dimensions of the end effectors, shafts, devices, and/or the various components of the end effectors, shafts or devices are merely exemplary in nature and are not intended to be limiting. It is also contemplated that in certain variations, one or more of the various components of the end effectors or the devices, or one or more of the end effectors or the devices may be provided or utilized.

In certain variations, the various sheaths described herein for guiding a shaft or end effector may be used with a device or end effector having a curved or straight flexible or rigid shaft.

The cutting devices or scrapers described herein may be utilized to perform a discectomy or other spinal procedures. Additionally, the devices described herein may be utilized or provide methods for resecting, excising and/or removing tissue or soft tissue from various regions in a patient's or subject's body. For example, the devices described herein may be utilized to excise and/or remove or evacuate various tissues or cells including, but not limited to: nasal tissue, for example, nasal polyps; eye tissue; tissue in various gynecological procedures; tumors, e.g., cancerous tumors in the lungs, liver, and in other vital organs; and tissues or cells from other areas in a patient or subject.

An end effector with a reciprocating or "fixed" Scraper edge 4.1, a Reciprocating Cutter 4.2, and/or a Rigid Shaft 4.7 (as shown in FIG. 6) or an end effector of FIG. 7 may be useful for excising and/or evacuating various tissues. Such tissues include tissues within the full spectrum of consistency ranging from soft tissues, such as intradiscal nucleus pulposis, to tough tissues, such as End Plate cartilage and ligament, to hard tissues, such as bone. For example, the end effector may be used to prepare the intradiscal space for vertebral fusion procedures where, e.g., it may be desirable to remove the intradiscal nucleus pulposis and End Plate cartilage and scrape the underlying bone to cause bleeding of the bone to promote healing and fusion between the vertebral bodies and implant.

In certain variations, an end effector having a Rigid Shaft, a Reciprocating Cutter 4.2, and/or with or without a Scraping Edge, may be useful for excising and/or evacuating tissues in procedures such as a foramenotomy, where it is desirable to decompress an emanating nerve that passes through a stenosed foramen. The end effector having a curved, rigid shaft with or without a Scraping Edge (4.1) may be capable of reaching into the foramen and exposing the Window (4.6) to the inside surface of the foramen such that the reciprocating cutter 4.2 and/or the scraping edge 4.1 may excise tissue. The end effector may be utilized in both "open" and percutaneous surgical procedures.

Optionally, an end effector or device having a flexible shaft may be used in the tissue excising, scraping or evacuating procedures described above.

In certain variations, a device may include or a method may utilize a cutter positioned at the distal end of a flexible shaft that has a preformed or predetermined curvature. The shaft may be adapted for insertion into a cannula or sheath where the distal end of the shaft may advance from the cannula (by advancing or retracting the cannula and/or the shaft relative to each other) toward a target site and the shaft may be configured to allow its predetermined curvature to position the distal end of the shaft near the target site, for example, by reverting or beginning to revert to its predetermined curvature upon exiting the cannula or sheath.

The devices described herein include a mechanism powered by a vacuum source. The devices may be used for applications where a source of vacuum is present. For example, a source of vacuum is frequently available when medical procedures are performed. Many medical devices utilize a reciprocating mechanism to perform their function. The devices described herein may be useful in procedures where evacuation or aspiration is necessary and the device may include evacuation or aspiration features in combination with a vacuum powered reciprocating mechanism.

In certain variations, a device using an external or internal vacuum source to power a reciprocating mechanism that is connected to a cutter thereby causing the cutter to reciprocate may include a "Y" connection within a handle that connects the vacuum source to both the cutter evacuation tube and the vacuum powered mechanism. As a result, the vacuum performs several functions within the device, such as: powers the mechanism which causes the cutter to reciprocate, draws tissue into a cutting window such that it may be excised, and/or evacuates the excised tissue to a location external to the device, while maintaining a consistent vacuum pressure even when the vacuum source is shut off to the mechanism during reciprocation.

In certain variations, a cutting device implements a pneumatic logic or a method utilizes a pneumatic logic to operate a cutting or other reciprocating device whereby a vacuum mechanism valve sequence shuts off the vacuum source from the mechanism to allow a piston to return to its home position without venting the vacuum source to ambient pressure. As a result, the vacuum pressure remains consistent in the cutting and evacuation system portion of the device.

In certain variations, a method includes maneuvering a flexible shaft around sensitive tissues or structures in the human body by changing the shape of the shaft by extending or retracting an outer sheath on the shaft thereby allowing improved maneuverability of the shaft around structures or within confined spaces. Such a shaft and sheath may be incorporated in any of the devices or vacuum powered devices describe herein.

In certain variations, a semi-rigid or rigid outer sheath positioned over the flexible curved shaft that is used to change the radius of curvature of the curved shaft may be provided. The radius of curvature of the shaft increases when the straight and rigid sheath is extended over the curved portion of the shaft, whereas the radius of curvature of the shaft returns to its precured shape when the sheath is retracted from the curved portion of the shaft.

In certain variations, an electrically resistive, or bipolar or monopolar electrocautery system is included on the distal tip of the shaft that allows the physician to cauterize tissue to control bleeding at the operative site. The electrocautery system may be powered by wires that run the length of the shaft through an internal lumen within the shaft.

In certain variations, a cutting device utilizing any of the variations of vacuum powered mechanisms described herein results in automatic actuation of a cutter positioned on a flexible or rigid shaft, thereby providing a vacuum powered cutter. The vacuum mechanism for actuating the cutter may enable-controls to be utilized for other functions or functions other than operating the mechanism, thereby reducing the number of levers or control buttons on the device. For, example, other controls positioned on the device may be utilized for straightening or curving the shaft or for operating or controlling bipolar systems for cauterizing.

In one variation, the device may include a handle having a trigger. Actuation of the trigger may cause a cannula or sheath positioned over a flexible shaft extending from the handle to either extend or retract, depending on whether the trigger is pressed or released. The extension or retraction of the cannula may cause the flexible shaft to straighten or curve. The device may include a roller ball, knob or other control mechanism for adjusting or for turning on/off vacuum flow or ambient flow to thereby regulate cutting speed. For example, such a knob or roller ball may be positioned on the cutting device such that the knob or roller ball may be manipulated by a thumb or other finger on the hand holding the handle of the device or on a free hand of the user. Thus, the cutting device can by used with one hand, freeing up the other hand of the user or physician for other uses. A single vacuum line may attach to the device, which both evacuates excised tissue and powers the mechanism. For example, a "Y" connection within the handle of the device may connect the vacuum source to both the cutter evacuation tube and the vacuum powered mechanism, where the device maintains a consistent vacuum pressure or force at the cutting window for evacuating excised tissue during operation of the mechanism.

The mechanism according to the variations described herein may actuate a cutter automatically by using a mechanism powered by an external vacuum source. The external vacuum source may be connected to the device to provide suction to facilitate tissue cutting and evacuation, therefore, the use of the external vacuum source to power the cutter is completed without requiring an additional power source such as electricity, compressed air, or mechanical input by the operator.

Because vacuum power is used to actuate the cutter, operator fatigue may be reduced as compared to a system requiring the operator to manually actuate the reciprocating mechanism such as via button or trigger mechanism. Also, the use of vacuum to power the cutter actuation may significantly increase the rate at which the cutter actuates, thereby reducing the time required to complete tissue resection.

The use of vacuum power to actuate the cutter may allow the control for the rate of actuation to be moved from a "primary" position such as a trigger or button to a "secondary" position on the device handle. As a result, the primary control may be utilized to control the rate at which the cutter mechanism actuates or as a control for the radius of curvature of the shaft, or as a control for an electrocautery system.

A knob, trigger, roller clamp, or other control interfaces may be used to control the rate at which the vacuum mechanism reciprocates. These options allow the device to be designed in a variety of configurations to suit various surgical specialties or personal preferences.

The various pneumatic logic sequences utilized by the systems described herein may optionally maintain high vacuum throughout the engine cycle by never venting the vacuum source to the atmosphere. As a result, the vacuum pressure that facilitates cutting and evacuation may not decrease while the mechanism reciprocates.

A single tube from the vacuum source to the device to serve the functions of tissue cutting, evacuation and to power the mechanism which actuates the reciprocating cutter may be utilized. The single tube from the vacuum source simplifies connections required for device operation and reduces the number of tubes attached to the device thereby reducing the "clutter" and unwieldiness caused by multiple tubes and wire connections to the device.

In certain variations, a second source of vacuum may be provided such that separate vacuum sources power the mechanism and provide suction to the distal end of the cutting device or end effector for excising and/or evacuating tissue. In certain variations, one or more vacuum sources and/or one or more tubes or conduits connecting a vacuum source to a device to supply suction to the device and/or to power the device may be utilized or provided.

A cannula may be used on the flexible shaft to change the radius of curvature on the shaft in a range from nearly straight to curved in an arc of 180 degrees. This allows the operator to optimize the curvature of the shaft based on the patient anatomy. The operator can increase or decrease the force between the shaft and the target tissue being excised by extending or retracting the cannula to increase or decrease the natural radius of curvature of the shaft.

Optionally, an electrically resistive, or monopolor or bipolar cautery may be used on the distal tip of the devices described herein to allow the operator to cauterize tissue to control bleeding at the site where tissue has been excised. This feature obviates the need to remove the device from the operative site to replace it with an electrocautery device. This improves speed and ease-of-use for the operator while reducing blood loss for the patient.

The devices described herein may be manufactured using low cost components and assembly techniques; as a result, the cost of the device is much lower than a similar device which utilizes an electric motor.

The devices described herein may have a relatively low mass and may be easily sterilized using commonly used sterilization techniques such as, e.g., electron beam radiation, gamma radiation, or Ethylene Oxide gas.

Other variations of vacuum powered devices and methods are provided below. For example, a medical device may utilize a mechanism powered by an external source of vacuum to perform one or more function(s) through reciprocating motion output by the mechanism. The device may excise and evacuate tissue. The device may have a single attachment to an external vacuum source wherein said vacuum provides power to the mechanism and assists in excising tissue. The device may have a single attachment to an external vacuum source wherein said vacuum provides power to the mechanism and assists in evacuating tissue. The device may utilize a mechanism that does not utilize inertia of mass to transition past valves to change state. The device may not vent the external vacuum source to ambient air at any time during its cycle thereby causing a drop in vacuum within the device. The device may include a flexible shaft that has a preformed curvature on the distal portion and a straight rigid or semi-rigid cannula around the outer diameter of the shaft; the radius of curvature of the shaft may be changed by sliding the cannula over the distal curvature whereby the radius of curvature is increased when the cannula is extended over the distal curvature and the distal curvature returns to its' preformed curvature when the cannula is retracted from the distal curvature. The device may include a monopolar electrode or bipolar electrodes on or near the distal extremity. The device may have a single connection to an external vacuum source that powers a vacuum powered mechanism and evacuates excised tissue. The single connection to an external vacuum source may also use vacuum to draw tissue into a cutting window to present tissue for the purpose of excising said tissue.

A medical device may include a mechanism powered by an external vacuum source wherein said mechanism is comprised of a piston that is set into motion by creating differential pressure on either side of the piston wherein one side of the piston has ambient air and the air on the other side of the piston is at least partially evacuated. The mechanism may include a valve component that opens the volume next to the Piston alternately to ambient air or vacuum. The valve component may be actuated as a result of translation of the Piston wherein the Piston acts upon the valve to cause it to open or close the fluid connections to ambient air or to the external vacuum source.

A method for causing a reciprocating mechanism powered by vacuum to transition past valves to change states wherein an adequate volume of air has been evacuated prior to closing the valve to the external vacuum source such that the mechanism continues to move into the evacuated volume such that the valve fully transitions to open the source of vacuum to a different volume may also be provided.

The method may include the following logic sequence: Vacuum open to the distal side of the Cylinder, ambient is closed to distal; ambient open to proximal side of Cylinder, vacuum is closed to proximal; Piston advances toward distal position due to the vacuum inside the distal side of the cylinder and ambient pressure on the proximal side of the Piston; Piston contacts Shuttle and advances it toward the distal position; Vacuum Seal on Shuttle moves from proximal side of Vacuum Port to the distal side of the Vacuum Port while the Distal Seal on the Shuttle opens the ambient air to vent the distal side of the Cylinder to ambient pressure and the Proximal Seal on the Shuttle closes the ambient air vent to the proximal side of the Cylinder; Piston reverses direction and moves in the proximal direction due to the vacuum inside the Cylinder proximal to the Piston and ambient air on the distal side of the Piston; Piston contacts Shuttle and advances toward the proximal position; Vacuum Seal on Shuttle moves from distal side of Vacuum Port to the proximal side of the Vacuum Port while the Proximal Seal on the Shuttle opens the ambient air to vent the proximal end of the Cylinder to ambient pressure and the Distal Seal on the Shuttle closes the ambient air vent to the Distal side of the Cylinder. The above steps may repeat unless the vacuum source is disconnected, turned off, or if the vacuum is inadequate to overcome the force required to move the Piston.

Optionally, the method may include the following logic sequence: Vacuum open to the distal side of the Cylinder, ambient is closed to distal; ambient open to proximal side of Cylinder; Piston advances toward distal position due to the vacuum inside the distal side of the cylinder and ambient pressure on the proximal side of the Piston; Piston contacts Shuttle and advances it toward the distal position; Vacuum Seal on Shuttle shuts off vacuum to the distal side of the Piston and continues to move distally thereby opening the ambient air supply to the distal side of the Piston; Return Spring motivates the Piston in the proximal direction due to the equalization of air pressure on both sides of the Piston; Piston Shaft contacts Shuttle and motivates it in the proximal direction; Shuttle Seal on the Shuttle shuts off ambient air supply to the distal side of the Piston and opens the vacuum to the distal side of the Piston. The above steps may repeat unless the vacuum source is disconnected, turned off, or if the vacuum is inadequate to overcome the force required to move the Piston.

In another variation, a medical device includes a reciprocating cutting blade such as is used to excise and evacuate tissue that uses a reciprocating mechanism powered by an external vacuum source that may be used for medical procedures where a source of vacuum is present.

The above arrangements, materials, and dimensions for the vacuum powered mechanisms described herein are exemplary and are not intended to be limiting.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A vacuum powered tissue cutting device comprising:
an elongate shaft having a proximal end, a distal end and a lumen defined therein, wherein the distal end has an opening for receiving tissue;
a cutter positioned within the elongate shaft, wherein the cutter is configured to be reciprocated to cut tissue;
a chamber coupled to the proximal end of the elongate shaft such that the elongate shaft remains fixed relative to the chamber, the chamber having a mechanism positioned therein, wherein the mechanism is powered by suction created by a vacuum source such that the mechanism produces a reciprocating motion which causes the cutter to reciprocate; and wherein the mechanism comprises a piston and a valve, wherein the suction is applied to both sides of the piston in an alternating manner to cause the piston to reciprocate which causes the cutter to reciprocate, wherein the piston is coupled to the valve by a linkage mechanism that translates motion from the piston to the valve.

2. The device of claim 1, wherein the mechanism is powered solely by suction created by the vacuum source.

3. The device of claim 1, wherein suction from the vacuum source draws tissue into the opening 4. The device of claim 1, wherein the cutter is configured to reciprocate past the opening in the elongate shaft to cut the tissue in the opening.

5. The device of claim 1, wherein the device is configured such that cut tissue is evacuated through an evacuation lumen in the elongate shaft by suction created by the vacuum source.

6. The device of claim 1, wherein the device is configured to receive suction from a single vacuum source which supplies suction for evacuation and for powering the mechanism.

7. The device of claim 1, wherein the elongate shaft has a lumen for delivering irrigant to the distal end of an evacuation lumen in the elongate shaft, wherein the irrigant does not flow through the lumen unless suction from the vacuum source is present to draw the irrigant through the lumen.

8. The device of claim 1, wherein the chamber is in the form of an ergonomic handle.

9. The device of claim 8, wherein the handle is positioned at an angle relative to the elongate shaft thereby providing a clear line of site above and/or to the side of the elongate shaft.

10. The device of claim 1, wherein the chamber and mechanism are positioned at an angle relative to the elongate shaft, wherein the mechanism is connected to the cutter and the mechanism reciprocates the cutter in a rectilinear motion.

11. The device of claim 1, wherein a tissue collection chamber is integrated in the device such that removal of the chamber disables the device 12. The device of claim 1, wherein the distal end of the shaft includes a malleable portion, wherein the cutter is reciprocated within the malleable portion.

13. The device of claim 1, wherein the mechanism is powered by vacuum available in a physician's office.

14. The device of claim 1, wherein the cutter is a cutting blade and the cutting blade is not exposed on an outside of the opening to provide safety to patients.

15. The device of claim 1, wherein the vacuum powered mechanism reciprocates at a rate of less than about 1200 cycles/min.

16. The device of claim 1, wherein the speed of the cutter ranges from 250-2500 cycles/min.

17. The device of claim 1, wherein the linkage mechanism comprises a bi-stable switch.

18. The device of claim 1, further comprising an electrocautery wire positioned at the distal end of the elongate shaft.

19. The device of claim 1, further comprising a lumen in the elongate shaft for delivering an anticoagulation therapy.

20. The device of claim 1, wherein the device is fully disposable.

21. A vacuum powered tissue cutting device comprising:
an elongate shaft having a proximal end, a distal end and a lumen defined therein, wherein the distal end has an opening for receiving tissue;
a cutter positioned within the elongate shaft, wherein the cutter is configured to be reciprocated past the opening in the elongate shaft to cut tissue in the opening;
a chamber coupled to the proximal end of the elongate shaft, the chamber having a cutter driver assembly positioned therein, wherein the cutter driver assembly comprises a piston and a valve and is powered by suction created by a vacuum source such that the cutter driver assembly produces a reciprocating motion which causes the cutter to reciprocate, wherein the suction is applied to both sides of the piston in an alternating manner to cause the piston to produce the reciprocating motion, wherein the piston is coupled to the valve by a linkage mechanism that translates motion from the piston to the valve.

22. A method of cutting and removing tissue from a subject comprising:
advancing a cutting device next to a target tissue in the subject, the cutting device having an elongate shaft and a cutter positioned within the elongate shaft;
powering the cutting device using suction created by a vacuum source such that the cutting device produces a reciprocating motion which causes the cutter to reciprocate;
cutting tissue with the reciprocating cutter; and
evacuating the cut tissue using the suction created by the vacuum source; and wherein the vacuum powered cutting device comprises a piston and a valve, wherein the suction is applied to both sides of the piston in an alternating manner to cause reciprocating motion and wherein the piston is coupled to the valve by a linkage mechanism that translates motion from the piston to the valve.

23. The method of claim 22, further comprising drawing target tissue into an opening in the elongate shaft using suction from the vacuum source, wherein the cutter is configured to be reciprocated past the opening in the elongate shaft to cut tissue in the opening.

24. The method of claim 22, wherein the proximal end of the elongate shaft is coupled to a handle such that the elongate shaft remains fixed relative to the handle while the cutter is being reciprocated.

25. The method of claim 22, wherein the cutting device is powered solely by suction created by the vacuum source.

26. The method of claim 22, wherein the cut tissue is evacuated through an evacuation lumen in the elongate shaft by suction created by the vacuum source.

27. The method of claim 22, wherein suction is received from a single vacuum source which supplies suction for evacuation and for reciprocating the cutter.

28. The method of claim 22, further comprising delivering irrigant to the distal end of an evacuation lumen in the elongate shaft, wherein the irrigant does not flow through the lumen unless suction from the vacuum source is present to draw the irrigant through the lumen.

29. The method of claim 22, wherein the cutting device comprises a handle positioned at an angle relative to the elongate shaft thereby providing a clear line of site above and/or to the side of the elongate shaft.

30. The method of claim 22, wherein a cutting device comprises a tissue collection chamber and removal of the chamber disables the device.

31. The method of claim 22, wherein the elongate shaft includes a malleable portion and the cutter is reciprocated within the malleable portion.

32. The method of claim 22, wherein the cutting device is powered by vacuum available in a physician's office.

33. The method of claim 22, wherein the vacuum powered cutting device comprises a mechanism that reciprocates at a rate of less than about 1200 rpm.

34. The method of claim 22, wherein the speed of the cutter ranges from 250-2500 cycles/min).

35. The method of claim 22, wherein the linkage mechanism comprises a bi-stable switch.

36. The method of claim 22, further comprising treating bleeding with an electrocautery wire positioned at the distal end of the elongate shaft.

37. The method of claim 22, further comprising delivering an anticoagulation therapy to a tissue site via the elongate shaft.

38. The method of claim 22, wherein the cutting device is fully disposable.

39. The method of claim 22, wherein the tissue is a polyp.

40. The method of claim 22, wherein the tissue is intradiscal nucleus.

41. A method for performing a polypectomy comprising:
advancing a cutting device next to a polyp in a subject;
powering the cutting device using suction created by a vacuum source such that the cutting device produces a reciprocating motion which causes the cutter to reciprocate or rotate; and
cutting the polyp with the reciprocating or rotating cutter; and wherein the vacuum powered cutting device comprises a piston and a valve, wherein the suction is applied to both sides of the piston in an alternating manner to cause the reciprocating motion and wherein the piston is coupled to the valve by a linkage mechanism that translates motion from the piston to the valve.

42. The method of claim 41, further comprising evacuating the cut polyp using the suction created by the vacuum source.

43. The method of claim 41, wherein the cutting device is powered solely by suction created by the vacuum source.

44. A method for performing a discectomy comprising:
advancing a cutting device into a disc in a spine of a subject;
powering the cutting device using suction created by a vacuum source such that the cutting device produces a reciprocating motion which causes the cutter to reciprocate or rotate; and
cutting a nucleus of the disc with the reciprocating or rotating cutter; and wherein the vacuum powered cutting device comprises a piston and a valve, wherein the suction is applied to both sides of the piston in an alternating manner to cause the reciprocating motion and wherein the piston is coupled to the valve by a linkage mechanism that translates motion from the piston to the valve.

45. The method of claim 44, further comprising evacuating the cut disc or nucleus using the suction created by the vacuum source.

46. The method of claim 44, wherein the cutting device is powered solely by suction created by the vacuum source.

* * * * *